United States Patent
Chng et al.

(10) Patent No.: US 10,995,329 B2
(45) Date of Patent: *May 4, 2021

(54) ENGINEERED PHENYLALANINE AMMONIA LYASE POLYPEPTIDES

(71) Applicant: Codexis, Inc., Redwood City, CA (US)

(72) Inventors: Chinping Chng, Menlo Park, CA (US); William Casey Hallows, San Francisco, CA (US); Nicholas J. Agard, San Francisco, CA (US); Oscar Alvizo, Fremont, CA (US); Nikki Dellas, Mountain View, CA (US); Gjalt W. Huisman, Redwood City, CA (US); John Joseph Nicols, Redwood City, CA (US)

(73) Assignee: Codexis, Inc., Redwood City, CA (US)

( * ) Notice: Subject to any disclaimer, the term of this patent is extended or adjusted under 35 U.S.C. 154(b) by 478 days.

This patent is subject to a terminal disclaimer.

(21) Appl. No.: 15/894,446

(22) Filed: Feb. 12, 2018

(65) Prior Publication Data

US 2018/0230448 A1    Aug. 16, 2018

Related U.S. Application Data

(60) Provisional application No. 62/458,232, filed on Feb. 13, 2017, provisional application No. 62/565,555, filed on Sep. 29, 2017.

(51) Int. Cl.
| | | |
|---|---|---|
| *C12N 9/88* | (2006.01) | |
| *C12N 15/00* | (2006.01) | |
| *A61K 48/00* | (2006.01) | |
| *A61K 38/00* | (2006.01) | |
| *A61K 9/00* | (2006.01) | |

(52) U.S. Cl.
CPC ............... *C12N 9/88* (2013.01); *C12N 15/00* (2013.01); *C12Y 403/01024* (2013.01); *A61K 9/0019* (2013.01); *A61K 9/0053* (2013.01); *A61K 38/00* (2013.01); *A61K 48/00* (2013.01)

(58) Field of Classification Search
CPC ...................................................... C12N 9/88
See application file for complete search history.

(56) References Cited

U.S. PATENT DOCUMENTS

| | | |
|---|---|---|
| 5,605,793 A | 2/1997 | Stemmer |
| 5,753,487 A | 5/1998 | Eigtved et al. |
| 5,811,238 A | 9/1998 | Stemmer et al. |
| 5,830,721 A | 11/1998 | Stemmer et al. |
| 5,834,252 A | 11/1998 | Stemmer et al. |
| 5,837,458 A | 11/1998 | Minshull et al. |
| 5,928,905 A | 7/1999 | Stemmer et al. |
| 6,096,548 A | 8/2000 | Stemmer |
| 6,117,679 A | 9/2000 | Stemmer |
| 6,132,970 A | 10/2000 | Stemmer |
| 6,165,793 A | 12/2000 | Stemmer |
| 6,180,406 B1 | 1/2001 | Stemmer |
| 6,251,674 B1 | 6/2001 | Tobin et al. |
| 6,265,201 B1 | 7/2001 | Wackett et al. |
| 6,277,638 B1 | 8/2001 | Stemmer |
| 6,287,861 B1 | 9/2001 | Stemmer et al. |
| 6,287,862 B1 | 9/2001 | delCardayre et al. |
| 6,291,242 B1 | 9/2001 | Stemmer |
| 6,297,053 B1 | 10/2001 | Stemmer |
| 6,303,344 B1 | 10/2001 | Patten et al. |
| 6,309,883 B1 | 10/2001 | Minshull et al. |
| 6,319,713 B1 | 11/2001 | Patten et al. |
| 6,319,714 B1 | 11/2001 | Crameri et al. |
| 6,323,030 B1 | 11/2001 | Stemmer |
| 6,326,204 B1 | 12/2001 | delCardayre et al. |
| 6,335,160 B1 | 1/2002 | Patten et al. |
| 6,335,198 B1 | 1/2002 | delCardayre et al. |
| 6,337,186 B1 | 1/2002 | Krebber |
| 6,344,356 B1 | 2/2002 | Stemmer |
| 6,352,859 B1 | 3/2002 | delCardayre et al. |
| 6,355,484 B1 | 3/2002 | Patten et al. |
| 6,358,740 B1 | 3/2002 | Patten et al. |

(Continued)

FOREIGN PATENT DOCUMENTS

| | | |
|---|---|---|
| WO | 95/22625 A1 | 8/1995 |
| WO | 95/33836 A1 | 12/1995 |

(Continued)

OTHER PUBLICATIONS

Studer. Residue mutations and their impact on protein structure and function: detecting beneficial and pathogenic changes. Biochem. J. (2013) 449, 581-594.*
PAL_NOSP7. UnitProtKB Database. 2015.*
Moffitt. Discovery of two cyanobacterial phenylalanine ammonia lyases: kinetic and structural characterization. Biochemistry 46: 1004-1012(2007).*
Altschul, S.F., et al., "Gapped BLAST and PSI-BLAST: a new generation of protein database search programs," Nucleic Acids Res., 25(17):3389-3402 (1997).
Altschul, S., et al., "Basic local alignment search tool," J. Mol. Biol., 215: 403-410 (1990).

(Continued)

*Primary Examiner* — Yong D Pak
(74) *Attorney, Agent, or Firm* — Codexis, Inc.

(57) ABSTRACT

The present invention provides engineered phenylalanine ammonia lyase (PAL) polypeptides and compositions thereof, as well as polynucleotides encoding the engineered phenylalanine ammonia lyase (PAL) polypeptides. In some embodiments, the engineered PAL polypeptides are optimized to provide enhanced catalytic activity, as well as reduced sensitivity to proteolysis and increased tolerance to storage at elevated temperatures. In some embodiments, the engineered PAL polypeptides contain fewer phenylalanine residues than wild-type PAL polypeptides. The present invention also provides methods for the use of the compositions comprising the engineered PAL polypeptides for therapeutic and industrial purposes.

28 Claims, 6 Drawing Sheets

Specification includes a Sequence Listing.

(56) References Cited

U.S. PATENT DOCUMENTS

| | | |
|---|---|---|
| 6,358,742 B1 | 3/2002 | Stemmer |
| 6,365,377 B1 | 4/2002 | Patten et al. |
| 6,365,408 B1 | 4/2002 | Stemmer |
| 6,368,861 B1 | 4/2002 | Crameri et al. |
| 6,372,497 B1 | 4/2002 | Stemmer |
| 6,376,246 B1 | 4/2002 | Crameri et al. |
| 6,379,964 B1 | 4/2002 | delCardayre et al. |
| 6,387,702 B1 | 5/2002 | Stemmer |
| 6,391,552 B2 | 5/2002 | Stemmer |
| 6,391,640 B1 | 5/2002 | Minshull et al. |
| 6,395,547 B1 | 5/2002 | Stemmer |
| 6,406,855 B1 | 6/2002 | Patten et al. |
| 6,406,910 B1 | 6/2002 | Patten et al. |
| 6,413,745 B1 | 7/2002 | Patten et al. |
| 6,413,774 B1 | 7/2002 | Stemmer |
| 6,420,175 B1 | 7/2002 | Stemmer |
| 6,423,542 B1 | 7/2002 | Crameri et al. |
| 6,426,224 B1 | 7/2002 | Crameri et al. |
| 6,436,675 B1 | 8/2002 | Welch et al. |
| 6,444,468 B1 | 9/2002 | Stemmer et al. |
| 6,455,253 B1 | 9/2002 | Patten et al. |
| 6,479,652 B1 | 11/2002 | Crameri et al. |
| 6,482,647 B1 | 11/2002 | Stemmer |
| 6,483,011 B1 | 11/2002 | Stemmer et al. |
| 6,484,105 B2 | 11/2002 | Zhang |
| 6,489,146 B2 | 12/2002 | Stemmer et al. |
| 6,500,617 B1 | 12/2002 | Stemmer et al. |
| 6,500,639 B2 | 12/2002 | Subramanian |
| 6,506,602 B1 | 1/2003 | Stemmer |
| 6,506,603 B1 | 1/2003 | Stemmer |
| 6,518,065 B1 | 2/2003 | Stemmer |
| 6,519,065 B1 | 2/2003 | Colbourne et al. |
| 6,521,453 B1 | 2/2003 | Crameri et al. |
| 6,528,311 B1 | 3/2003 | delCardayre et al. |
| 6,537,746 B2 | 3/2003 | Arnold et al. |
| 6,573,098 B1 | 6/2003 | Stemmer |
| 6,576,467 B1 | 6/2003 | Stemmer |
| 6,579,678 B1 | 6/2003 | Patten et al. |
| 6,586,182 B1 | 7/2003 | Patten et al. |
| 6,602,986 B1 | 8/2003 | Stemmer et al. |
| 6,605,430 B1 | 8/2003 | Affholter et al. |
| 6,613,514 B2 | 9/2003 | Patten et al. |
| 6,653,072 B1 | 11/2003 | Patten et al. |
| 6,686,515 B1 | 2/2004 | Lassner et al. |
| 6,703,240 B1 | 3/2004 | Stemmer et al. |
| 6,716,631 B1 | 4/2004 | delCardayre et al. |
| 6,825,001 B2 | 11/2004 | Wackett et al. |
| 6,902,922 B2 | 6/2005 | Ness |
| 6,917,882 B2 | 7/2005 | Selfinov et al. |
| 6,946,296 B2 | 9/2005 | Patten et al. |
| 6,961,664 B2 | 11/2005 | Selfinov et al. |
| 6,995,017 B1 | 2/2006 | Stemmer |
| 7,024,312 B1 | 4/2006 | Selfinov et al. |
| 7,058,515 B1 | 6/2006 | Selfinov et al. |
| 7,105,297 B2 | 9/2006 | Minshull et al. |
| 7,148,054 B2 | 12/2006 | delCardayre et al. |
| 7,220,566 B2 | 5/2007 | Ness |
| 7,288,375 B2 | 10/2007 | Stemmer et al. |
| 7,384,387 B2 | 6/2008 | Raillard et al. |
| 7,421,347 B2 | 9/2008 | Selfinov et al. |
| 7,430,477 B2 | 9/2008 | Selfinov et al. |
| 7,462,469 B2 | 12/2008 | Bass et al. |
| 7,531,341 B1 | 5/2009 | Vellard et al. |
| 7,534,564 B2 | 5/2009 | Patten et al. |
| 7,534,595 B2 | 5/2009 | Vellard et al. |
| 7,537,923 B2 | 5/2009 | Kakkis et al. |
| 7,560,263 B2 | 7/2009 | Kakkis et al. |
| 7,620,500 B2 | 11/2009 | Mundorff et al. |
| 7,620,502 B2 | 11/2009 | Selfinov et al. |
| 7,629,170 B2 | 12/2009 | delCardayre et al. |
| 7,702,464 B1 | 4/2010 | Emig et al. |
| 7,747,391 B2 | 6/2010 | Gustafsson et al. |
| 7,747,393 B2 | 6/2010 | Fox |
| 7,751,986 B2 | 7/2010 | Gustafsson et al. |
| 7,776,598 B2 | 8/2010 | Patten et al. |
| 7,783,428 B2 | 8/2010 | Gustafsson et al. |
| 7,790,433 B2 | 9/2010 | Kakkis et al. |
| 7,795,030 B2 | 9/2010 | Minshull et al. |
| 7,853,410 B2 | 12/2010 | Selfinov et al. |
| 7,868,138 B2 | 1/2011 | Stemmer et al. |
| 7,873,477 B1 | 1/2011 | Gustafsson et al. |
| 7,873,499 B2 | 1/2011 | Selfinov et al. |
| 7,904,249 B2 | 3/2011 | Selfinov et al. |
| 7,957,912 B2 | 6/2011 | Selfinov et al. |
| 7,981,614 B2 | 7/2011 | Stemmer et al. |
| 8,014,961 B2 | 9/2011 | Bass et al. |
| 8,029,988 B2 | 10/2011 | Crameri et al. |
| 8,048,674 B2 | 11/2011 | Minshull et al. |
| 8,058,001 B2 | 11/2011 | Crameri et al. |
| 8,076,138 B2 | 12/2011 | delCardayre et al. |
| 8,108,150 B2 | 1/2012 | Mundorff et al. |
| 8,170,806 B2 | 5/2012 | Selfinov et al. |
| 8,224,580 B2 | 7/2012 | Mundorff et al. |
| 8,377,681 B2 | 2/2013 | delCardayre et al. |
| 8,383,346 B2 | 2/2013 | Colbeck et al. |
| 8,457,903 B1 | 6/2013 | Emig et al. |
| 8,504,498 B2 | 8/2013 | Fox |
| 8,589,085 B2 | 11/2013 | Selfinov et al. |
| 8,762,066 B2 | 6/2014 | Fox |
| 8,768,871 B2 | 7/2014 | Fox |
| 9,593,326 B2 | 3/2017 | Clark et al. |
| 9,611,468 B2 | 4/2017 | Huisman et al. |
| 2005/0260724 A1 | 11/2005 | Ben-Bassat et al. |
| 2008/0220990 A1 | 9/2008 | Fox |
| 2009/0312196 A1 | 12/2009 | Colbeck et al. |
| 2012/0177722 A1 | 7/2012 | Weiner et al. |
| 2013/0005012 A1 | 1/2013 | Yu |
| 2013/0039898 A1 | 2/2013 | Okhamafe et al. |
| 2013/0340119 A1 | 12/2013 | Plesch et al. |
| 2014/0005057 A1 | 1/2014 | Clark et al. |
| 2014/0214391 A1 | 7/2014 | Cope |
| 2014/0221216 A1 | 8/2014 | Cope et al. |
| 2014/0314843 A1 | 10/2014 | Huisman et al. |
| 2015/0050658 A1 | 2/2015 | Cho |
| 2015/0133307 A1 | 5/2015 | Zhang et al. |
| 2015/0134315 A1 | 5/2015 | Sarmiento et al. |
| 2016/0257932 A1 | 9/2016 | Kahvejian et al. |

FOREIGN PATENT DOCUMENTS

| | | |
|---|---|---|
| WO | 96/00787 A1 | 1/1996 |
| WO | 97/0078 A1 | 1/1997 |
| WO | 97/20078 A1 | 6/1997 |
| WO | 97/35966 A1 | 10/1997 |
| WO | 98/27230 A1 | 6/1998 |
| WO | 00/42651 A1 | 7/2000 |
| WO | 01/75767 A2 | 10/2001 |
| WO | 2008/153776 A1 | 12/2008 |
| WO | 2009/152336 A1 | 12/2009 |
| WO | 2010/144103 A1 | 12/2010 |
| WO | 2011/097335 A2 | 8/2011 |
| WO | 2012/122333 A1 | 9/2012 |

OTHER PUBLICATIONS

Ambrus, C_M_, et al., "Phenylalanine depletion for the management of phenylketonuria: use of enzyme reactors with immobilized enzymes," Science, 201:837-839 [1978].

Bartsch, S., et al., "Mutational analysis of phenylalanine ammonia lyase to improve reactions rates for various substrates," Prot. Eng. Des. Sel., 23:929-933 [2010].

Bate, N.J., et al., "Quantitative relationship between phenylalanine ammonia-lyase levels and phenylpropanoid accumulation in transgenic tobacco identifies a rate-determining step in natural product synthesis," Proc. Natl. Acad. Sci. USA, 91:7608-7612 [1994].

Beaucage, S.L., et al., "Deoxynucleoside phosphoamidites—A new class of key intermediates for deoxypolynucleotide synthesis," Tetrahedron Letters, 22(20):1859-62 (1981).

Black, M.E., et al., "Creation of drug-specific herpes simplex virus type 1 thymidine kinase mutants for gene therapy," Proc Natl Acad Sci USA, 93:3525-3529 (1996).

(56) References Cited

OTHER PUBLICATIONS

Botstein, D., et al., "Strategies and applications of in vitro mutagenesis," Science, 229(4719):1193-1201, 1985.
Bourget, L., et al., "Artificial cell-microencapsulated phenylalanine ammonia-lyase," Appl. Biochem. Biotechnol., 10:57-59 [1984].
Caldwell, R.C., et al., "Mutagenic PCR," PCR Methods Appl., 3:S136-S140 [1994].
Carter, P., "Site-directed mutagenesis," Biochem. J., 237:1-7 (1986).
Christians, F.C., et al., "Directed evolution of thymidine kinase for AZT phosphorylation using DNA family shuffling," Nat. Biotechnol., 17:259-264 (1999).
Crameri, A., et al., "DNA shuffling of a family of genes from diverse species accelerates directed evolution", Nature, 391:288-291 (1998).
Crameri, A., et al., "Improved green fluorescent protein by molecular evolution using DNA shuffling," Nat. Biotechnol., 14(3):315-319 (1996).
Crameri, A., et al., "Molecular evolution of an arsenate detoxification pathway by DNA shuffling," Nat. Biotechnol., 15(5):436-438 (1997).
Dale, S.J., et al., "Oligonucleotide-directed random mutagenesis using the phosphorothioate method," Methods Mol. Biol., 57:369-74 (1996).
De Boer, H.A., et al., "The tac promoter: A functional hybrid derived from the trp and lac promoters," Proc. Natl Acad. Sci. USA, 80: 21-25 (1983).
Gloge, A., et al., "Phenylalanine ammonia-lyase: the use of its broad substrate specificity for mechanistic investigations and biocatalysis—synthesis of L-arylalanines," Chem., 6(18): 3386-3390 [2000].
Guo, Z., et al., "3'-End-Forming Signals of Yeast mRNA," Mol. Cell. Biol., 15(11):5983-5990 [1995].
Henikoff, S., et al., "Amino acid substitution matrices from protein blocks," Proc. Natl. Acad. Sci. USA, 89:10915-10919 [1992].
Ikeda, K, et al., "Phenylalanine ammonia-lyase modified with polyethylene glycol: potential therapeutic agent for phenylketonuria," Amino Acids, 29(3):283-287 [2005].
Kang, T.S., et al., "Converting an injectable protein therapeutic into an oral form: Phenylalanine ammonia lyase for phenylketonuria," Mol. Gen. Metabol., 99:4-9 [2010].
Kim, W., et al., "Trends in enzyme therapy for phenylketonuria," Molec. Therap., 10(2):220-224 [2004].
Kramer, B., et al., "Different base/base mismatches are corrected with different efficiencies by the methyl-directed DNA mismatch-repair system of *E coli*," Cell, 38(3):879-887, 1984.
Ling, M.M., et al., "Approaches to DNA Mutagenesis: An Overview," Anal. Biochem., 254(2):157-78 [1997].
Matthes, H.W.D., et al., "Simultaneous rapid chemical synthesis of over one hundred oligonucleotides on a microscale," EMBO J., 3(4):801-05 (1984).
Minshull, J., et al., "Protein evolution by molecular breeding," Curr. Op. Chem. Biol., 3(3):284-290 (1999).
Needleman, S., et al., "A general method applicable to the search for similarities in the amino acid sequence of two proteins," J. Mol. Biol. 48:443-453 (1970).
Pearson, W.R., "Improved tools for biological sequence comparison," Proc. Nat'l. Acad. Sci. USA, 85:2444-2448 (1988).

Romanos, M.A., et al., "Foreign gene expression in yeast: a review," Yeast 8:423-488 [1992].
Sarkissian, C.N., et al., "A different approach to treatment of phenylketonuria: Phenylalanine degradation with recombinant phenylalanine ammonia lyase," Proc. Natl. Acad. Sci. USA, 96:2339-2344 [1999].
Shah, R.M., et al., "Strategies to maximize the encapsulation efficiency of phenylalanine ammonia lyase in microcapsules," Int. J. Pharmaceut., 356(102):61-68 [2008].
Simonen, M., et al., "Protein Secretion in *Bacillus* Species," Microbiological Reviews, 57:109-137 (1993).
Smith, M., "In vitro mutagenesis," Ann. Rev. Genet., 19:423-462 (1985).
Smith, T., et al., "Comparison of Biosequences," Adv. Appl. Math, 2:482-489 (1981).
Stemmer, W., "DNA Shuffling by Random Fragmentation and Reassembly: In vitro Recombination for Molecular Evolution," Proc. Natl. Acad. Sci. USA, 91:10747-10751 (1994).
Stemmer, W.P.C., "Rapid evolution of a protein in vitro by DNA shuffling", Nature, 370:389-391 (1994).
Turner, N.J., "Ammonia lyases and aminomutases as biocatalysts for the synthesis of alpha-amino and beta-amino acids," Curr. Opin. Chem. Biol., 15(2):234-240 [2011].
Villa-Komaroff, L., et al., "A bacterial clone synthesizing proinsulin," Proc. Natl Acad. Sci. USA, 75:3727-3731 (1978).
Wells, J.A., et al., "Cassette mutagenesis: an efficient method for generation of multiple mutations at defined sites," Gene, 34:315-323 (1985).
Zhang, J-H., et al., "Directed evolution of a fucosidase from a galactosidase by DNA shuffling and screening ," Proc. Nat. Acad. Sci., U.S.A., 94:4504-4509 (1997).
Zhao, H., et al., "Molecular evolution by staggered extension process (StEP) in vitro recombination," Nat. Biotechnol., 16:258-261 (1998).
NCBI Accession No. YP_001865631.1 dated Jun. 10, 2013.
NCBI Accession No. YP_007127054.1 dated Jun. 11, 2013.
NCBI Accession No. YP_324488.1 dated Jun. 10, 2013.
NCBI Accession No. ZP_07108482.1 dated Nov. 9, 2010.
Rowles, I., et al., "Engineering of phenylalanine ammonia lyase from Rhodotorula graminis for the enhanced synthesis of unnatural l-amino acids," Tetrahedron, 72(46):7343-7347 [2016].
Zhang, F., et al., "Modulating the pH Activity Profiles of Phenylalanine Ammonia Lyase from Anabaena variabilis by Modification of Center-Near Surface Residues," Appl. Biochem. Biotechnol., 183:699-711 [2017].
www.Codexis.com et al., "Codexis CodeEvolver Technology", Biomed Mass Spectrom. Gen Med, pp. 392-394 [2017]; Retrieved from the Internet.
Langer, B., et al., "Identification of Essential Amino Acids in Phenylalanine Ammonia-Lyase by Site-Directed Mutagenesis," Biochemistry, 36(36):10867-10871 [1997].
Siloto, R.M.P., et al., "Site saturation mutagenesis: Methods and applications in protein engineering," Biocatalysis and Agricultural Biotechnology, 1(3):181-189 [2012].

\* cited by examiner

SEQUENCE LISTING

<160> NUMBER OF SEQ ID NOS: 12

<210> SEQ ID NO 1
<211> LENGTH: 1701
<212> TYPE: DNA
<213> ORGANISM: Artificial Sequence
<220> FEATURE:
<223> OTHER INFORMATION: Anabaena variabilis PAL

<400> SEQUENCE: 1

```
atgaaaaccc tgagccaggc acagagcaaa accagcagcc agcagtttag ctttaccggc      60
aatagcagcg caaatgtgat tattggtaat cagaaactga ccatcaatga tgttgcacgt     120
gttgcccgta atggcaccct ggttagcctg accaataata ccgatattct gcagggtatt     180
caggccagct gtgattatat caataatgca gttgaaagcg gtgaaccgat ttatggtgtt     240
accagcggtt ttggtggtat ggcaaatgtt gcaattagcc gtgaacaggc aagcgaactg     300
cagaccaatc tggtttggtt tctgaaaacc ggtgcaggta taaaactgcc gctggcagat     360
gttcgtgcag caatgctgct gcgtgcaaat agccacatgc gtggtgcaag cggtattcgt     420
ctggaactga ttaaacgcat ggaaatcttt ctgaatgccg tgttaccccc gtatgtttat     480
gaatttggta gcattggtgc cagcggtgat ctggttccgc tgagctatat taccggtagc     540
ctgattggcc tggacccgag ctttaaagtt gattttaatg gcaaagaaat ggacgcaccg     600
accgcactgc gtcagctgaa tctgagtccg ctgaccctgc tgccgaaaga aggtctggca     660
atgatgaatg gcaccagcgt tatgaccggt attgcagcaa attgtgttta tgatacccag     720
attctgaccg caattgcaat gggtgttcat gcactggata ttcaggcact gaatggtaca     780
aatcagagct ttcatccgtt tatccataac agcaaaccgc atccgggtca gctgtgggca     840
gcagatcaga tgattagcct gctggccaat agccagctgg ttcgtgatga actggatggt     900
aaacatgatt atcgtgatca tgaactgatc caggatcgtt atagcctgcg ttgtctgccg     960
cagtatctgg gtccgattgt tgatggtatt agccagattg ccaaacaaat cgaaattgag    1020
attaacagcg ttaccgataa cccgctgatt gatgttgata tcaggcaag ctatcatggt    1080 ggtaattttc tgggtcagta tgttggtatg ggtatggatc atctgcgcta ttatatcggt    1140
ctgctggcaa acatctgga tgttcagatt gcactgctgg catcaccgga atttagcaat    1200
ggtctgcctc cgagtctgct gggtaatcgt gaacgtaaag ttaatatggg tctgaaaggt    1260
ctgcagattt gcggtaatag cattatgccg ctgctgacct tttatggtaa tagtattgca    1320
gatcgttttc cgacccatgc cgaacagttt aaccagaata ttaacagcca gggttatacc    1380
agcgcaaccc tggcacgtcg tagcgttgat atttttcaga attatgttgc cattgccctg    1440
atgtttggtg ttcaggcagt tgatctgcgt acctacaaaa aaaccggtca ttatgatgca    1500
```

```
cgtgcctgtc tgtcaccggc aaccgaacgt ctgtatagcg cagttcgtca tgttgttggt    1560
cagaaaccga cctcagatcg tccgtatatt tggaatgata atgaacaggg tctggatgaa    1620
catattgcac gtattagtgc agatattgca gccggtggtg ttattgttca ggccgttcag    1680
gacattctgc cgtgtctgca t                                              1701

<210> SEQ ID NO 2
<211> LENGTH: 567
<212> TYPE: PRT
<213> ORGANISM: Artificial Sequence
<220> FEATURE:
<223> OTHER INFORMATION: Anabaena variabilis PAL

<400> SEQUENCE: 2
```

| Met | Lys | Thr | Leu | Ser | Gln | Ala | Gln | Ser | Lys | Thr | Ser | Ser | Gln | Gln | Phe |
|---|---|---|---|---|---|---|---|---|---|---|---|---|---|---|---|
| 1 | | | | 5 | | | | | 10 | | | | | 15 | |

| Ser | Phe | Thr | Gly | Asn | Ser | Ser | Ala | Asn | Val | Ile | Ile | Gly | Asn | Gln | Lys |
|---|---|---|---|---|---|---|---|---|---|---|---|---|---|---|---|
| | | | 20 | | | | | 25 | | | | | 30 | | |

| Leu | Thr | Ile | Asn | Asp | Val | Ala | Arg | Val | Ala | Arg | Asn | Gly | Thr | Leu | Val |
|---|---|---|---|---|---|---|---|---|---|---|---|---|---|---|---|
| | | | 35 | | | | | 40 | | | | | 45 | | |

| Ser | Leu | Thr | Asn | Asn | Thr | Asp | Ile | Leu | Gln | Gly | Ile | Gln | Ala | Ser | Cys |
|---|---|---|---|---|---|---|---|---|---|---|---|---|---|---|---|
| | 50 | | | | | 55 | | | | | 60 | | | | |

| Asp | Tyr | Ile | Asn | Asn | Ala | Val | Glu | Ser | Gly | Glu | Pro | Ile | Tyr | Gly | Val |
|---|---|---|---|---|---|---|---|---|---|---|---|---|---|---|---|
| 65 | | | | | 70 | | | | | 75 | | | | | 80 |

| Thr | Ser | Gly | Phe | Gly | Gly | Met | Ala | Asn | Val | Ala | Ile | Ser | Arg | Glu | Gln |
|---|---|---|---|---|---|---|---|---|---|---|---|---|---|---|---|
| | | | | 85 | | | | | 90 | | | | | 95 | |

| Ala | Ser | Glu | Leu | Gln | Thr | Asn | Leu | Val | Trp | Phe | Leu | Lys | Thr | Gly | Ala |
|---|---|---|---|---|---|---|---|---|---|---|---|---|---|---|---|
| | | | 100 | | | | | 105 | | | | | 110 | | |

| Gly | Asn | Lys | Leu | Pro | Leu | Ala | Asp | Val | Arg | Ala | Ala | Met | Leu | Leu | Arg |
|---|---|---|---|---|---|---|---|---|---|---|---|---|---|---|---|
| | | 115 | | | | | 120 | | | | | 125 | | | |

| Ala | Asn | Ser | His | Met | Arg | Gly | Ala | Ser | Gly | Ile | Arg | Leu | Glu | Leu | Ile |
|---|---|---|---|---|---|---|---|---|---|---|---|---|---|---|---|
| 130 | | | | | 135 | | | | | 140 | | | | | |

| Lys | Arg | Met | Glu | Ile | Phe | Leu | Asn | Ala | Gly | Val | Thr | Pro | Tyr | Val | Tyr |
|---|---|---|---|---|---|---|---|---|---|---|---|---|---|---|---|
| 145 | | | | | 150 | | | | | 155 | | | | | 160 |

| Glu | Phe | Gly | Ser | Ile | Gly | Ala | Ser | Gly | Asp | Leu | Val | Pro | Leu | Ser | Tyr |
|---|---|---|---|---|---|---|---|---|---|---|---|---|---|---|---|
| | | | | 165 | | | | | 170 | | | | | 175 | |

| Ile | Thr | Gly | Ser | Leu | Ile | Gly | Leu | Asp | Pro | Ser | Phe | Lys | Val | Asp | Phe |
|---|---|---|---|---|---|---|---|---|---|---|---|---|---|---|---|
| | | | 180 | | | | | 185 | | | | | 190 | | |

| Asn | Gly | Lys | Glu | Met | Asp | Ala | Pro | Thr | Ala | Leu | Arg | Gln | Leu | Asn | Leu |
|---|---|---|---|---|---|---|---|---|---|---|---|---|---|---|---|
| | | 195 | | | | | 200 | | | | | 205 | | | |

| Ser | Pro | Leu | Thr | Leu | Leu | Pro | Lys | Glu | Gly | Leu | Ala | Met | Met | Asn | Gly |
|---|---|---|---|---|---|---|---|---|---|---|---|---|---|---|---|
| 210 | | | | | 215 | | | | | 220 | | | | | |

| Thr | Ser | Val | Met | Thr | Gly | Ile | Ala | Ala | Asn | Cys | Val | Tyr | Asp | Thr | Gln |
|---|---|---|---|---|---|---|---|---|---|---|---|---|---|---|---|
| 225 | | | | | 230 | | | | | 235 | | | | | 240 |

| Ile | Leu | Thr | Ala | Ile | Ala | Met | Gly | Val | His | Ala | Leu | Asp | Ile | Gln | Ala |
|---|---|---|---|---|---|---|---|---|---|---|---|---|---|---|---|
| | | | | 245 | | | | | 250 | | | | | 255 | |

| Leu | Asn | Gly | Thr | Asn | Gln | Ser | Phe | His | Pro | Phe | Ile | His | Asn | Ser | Lys |
|---|---|---|---|---|---|---|---|---|---|---|---|---|---|---|---|
| | | | 260 | | | | | 265 | | | | | 270 | | |

| Pro | His | Pro | Gly | Gln | Leu | Trp | Ala | Ala | Asp | Gln | Met | Ile | Ser | Leu | Leu |
|---|---|---|---|---|---|---|---|---|---|---|---|---|---|---|---|
| | | 275 | | | | | 280 | | | | | 285 | | | |

| Ala | Asn | Ser | Gln | Leu | Val | Arg | Asp | Glu | Leu | Asp | Gly | Lys | His | Asp | Tyr |
|---|---|---|---|---|---|---|---|---|---|---|---|---|---|---|---|
| 290 | | | | | 295 | | | | | 300 | | | | | |

| Arg | Asp | His | Glu | Leu | Ile | Gln | Asp | Arg | Tyr | Ser | Leu | Arg | Cys | Leu | Pro |
|---|---|---|---|---|---|---|---|---|---|---|---|---|---|---|---|
| 305 | | | | | 310 | | | | | 315 | | | | | 320 |

Gln Tyr Leu Gly Pro Ile Val Asp Gly Ile Ser Gln Ile Ala Lys Gln
              325                 330                 335

Ile Glu Ile Glu Ile Asn Ser Val Thr Asp Asn Pro Leu Ile Asp Val
        340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 3
<211> LENGTH: 1701
<212> TYPE: DNA
<213> ORGANISM: Artificial Sequence
<220> FEATURE:
<223> OTHER INFORMATION: Variant of PAL from Anabaena variabilis

<400> SEQUENCE: 3
atgaaaaccc tgagtcaggc acagagcaaa accagcagcc agcagtttag ccataccggc     60
aatagcagcg caaatgtgat tattggtaat cagaaactga ccatcaatga tgttgtacgt    120
gttgcccgta atggcaccgc ggttagcctg accaataata agatattct gcagcgtatt    180 caggccagct gtgattatat caataatgca gttgaaaaag gtgaaccgat ttatggtgtt    240
accagcggtt ttggtggtat ggcaaatgtt gtaattagcc gtgaacaggc aagcgaactg    300
cagaccaatc tggtttggtt tctgaaaacc ggtgcaggta taaactgcc gctggcagat    360 gttcgtgcag caatgctgct gcgtgcaaat agccacatgc gtggtgcaag cggtattcgt    420
ctggaactga ttaaacgcat ggaaatcttt ctgaatgccg tgttacccc gtatgtttat    480 gaatttggta gcattggtgc cagcggtgat ctggttccgc tgagctatat taccggtagc    540
ctgattggcc tggaccccgag ctttaaagtt gattttaatg caaagaaat ggacgcaccg    600 accgcactgc gtcagctgaa tctgagtccg ctgaccctgc agccgaaaga aggtctggca    660

```
atgatgaatg gcaccagcgt tatgaccggt attgcagcaa attgtgttta tgatacccag    720
attctgaccg caattgcaat gggtgttcat gcactggata ttcaggcact gaatggtaca    780
aatcagagct ttcatccgtt tatccataac agcaaaccgc atccgggtca gctgtgggca    840
gcagatcaga tgattagcct gctggccggt agccagctgg ttcgtgatga actggatggt    900
aaacatgatt atatggatgg tgaactgatc caggatcgtt atagcctgcg ttgtctgccg    960
cagtatctgg gtccgattgt tgatggtatt agccagattg ccaaacaaat cgaaattgag   1020
attaacagcg ttaccgataa cccgctgatt gatgttgata tcaggcaag  ctatcatggt   1080 ggtaattttc tgggtcagta tgttggtatg ggtatggatc atctgcgcta ttatatcggt   1140
ctgctggcaa acatctgga tgttcagatt gcactgctgg catcaccgga atttagcaat   1200
ggtctgcctc cgagtctggt gggtaatcgt gaacgtaaag ttaatatggg tctgaaaggt   1260
ctgcagattt gcggtaatag cattatgccg ctgctgacct tttatggtaa tagtattgca   1320
gatcgttttc cgacccatgc cgaacagttt aaccagaata ttaacagcca gggttatacc   1380
agcgcaaccc tggcacgtcg tagcgttgat attttcaga attatgttgc cattgccctg   1440
atgtttggtg ttcaggcagt tgatctgcgt acctacaaaa aaaccggtca ttatgatgca   1500
cgtgcccagc tgtcaccggc aaccgaacgt ctgtatagcg cagttcgtca tgttgttggt   1560
aaaaaaccga gctcagatcg tccgtatatt tggaatgata tgaacaggg  tctggatgaa   1620 catattgcac gtattagtgc agatattgca gccggtggtg ttattgttca ggccgttcag   1680
gacattctgc cgccgctgca t                                             1701

<210> SEQ ID NO 4
<211> LENGTH: 567
<212> TYPE: PRT
<213> ORGANISM: Artificial Sequence
<220> FEATURE:
<223> OTHER INFORMATION: Variant of PAL from Anabaena variabilis

<400> SEQUENCE: 4

Met Lys Thr Leu Ser Gln Ala Gln Ser Lys Thr Ser Gln Gln Phe
1               5                   10                  15

Ser His Thr Gly Asn Ser Ser Ala Asn Val Ile Ile Gly Asn Gln Lys
                20                  25                  30

Leu Thr Ile Asn Asp Val Val Arg Val Ala Arg Asn Gly Thr Ala Val
            35                  40                  45

Ser Leu Thr Asn Asn Lys Asp Ile Leu Gln Arg Ile Gln Ala Ser Cys
        50                  55                  60

Asp Tyr Ile Asn Asn Ala Val Glu Lys Gly Glu Pro Ile Tyr Gly Val
65                  70                  75                  80

Thr Ser Gly Phe Gly Gly Met Ala Asn Val Val Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175
```

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
            195                 200                 205

Ser Pro Leu Thr Leu Gln Pro Lys Glu Gly Leu Ala Met Met Asn Gly
210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
            275                 280                 285

Ala Gly Ser Gln Leu Val Arg Asp Glu Leu Asp Gly Lys His Asp Tyr
            290                 295                 300

Met Asp Gly Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
            355                 360                 365

Gly Met Gly Met Asp His Leu Arg Tyr Tyr Ile Gly Leu Leu Ala Lys
            370                 375                 380

His Leu Asp Val Gln Ile Ala Leu Leu Ala Ser Pro Glu Phe Ser Asn
385                 390                 395                 400

Gly Leu Pro Pro Ser Leu Val Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
            435                 440                 445

Gln Phe Asn Gln Asn Ile Asn Ser Gln Gly Tyr Thr Ser Ala Thr Leu
            450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Gln Leu Ser Pro Ala Thr Glu Arg Leu Tyr
            500                 505                 510

Ser Ala Val Arg His Val Val Gly Lys Lys Pro Ser Ser Asp Arg Pro
            515                 520                 525

Tyr Ile Trp Asn Asp Asn Glu Gln Gly Leu Asp Glu His Ile Ala Arg
            530                 535                 540

Ile Ser Ala Asp Ile Ala Ala Gly Gly Val Ile Val Gln Ala Val Gln
545                 550                 555                 560

Asp Ile Leu Pro Pro Leu His
                565

<210> SEQ ID NO 5
<211> LENGTH: 1701

```
<212> TYPE: DNA
<213> ORGANISM: Artificial Sequence
<220> FEATURE:
<223> OTHER INFORMATION: Variant of PAL from Anabaena variabilis

<400> SEQUENCE: 5
atgaaaaccc tgagtcaggc acagagcaaa accagcagcc agcagtttag ccataccggc      60
aatagcagcg caaatgtgat tattggtaat cagaaactga ccatcaatga tgttgtacgt     120
gttgcccgta atggcaccgc ggttagcctg accaataata aagatattct gcagcgtatt     180
caggccagct gtgattatat caataatgca gttgaaaaag gtgaaccgat ttatggtgtt     240
accagcggtt ttggtggtat ggcaaatgtt gtaattagcc gtgaacaggc aagcgaactg     300
cagaccaatc tggtttggtt tctgaaaacc ggtgcaggta taaactgcc gctggcagat     360
gttcgtgcag caatgctgct gcgtgcaaat agccacatgc gtggtgcaag cggtattcgt     420
ctggaactga ttaaacgcat ggaaatcttt ctgaatgccg tgttacccc gtatgtttat     480
gaatttggta gcattggtgc cagcggtgat ctggttccgc tgagctatat taccggtagc     540
ctgattggcc tggacccgag ctttaaagtt gattttaatg caagaaat ggacgcaccg     600
accgcactgc gtcagctgaa tctgagtccg ctgacccctgc agccgaaaga aggtctggca     660
atgatgaatg gcaccagcgt tatgaccggt attgcagcaa attgtgttta tgatacccag     720
attctgaccg caattgcaat gggtgttcat gcactggata ttcaggcact gaatggtaca     780
aatcagagct tcatccgtt tatccataac agcaaaccgc atccgggtca gctgtgggca     840
gcagatcaga tgattagcct gctggccggt agccagctgg ttcgtgatga actggatggt     900
aaacatgatt atatggatgg tgaactgatc caggatcgtt atagcctgcg ttgtctgccg     960
cagtatctgg gtccgattgt tgatggtatt agccagattg ccaaacaaat cgaaattgag    1020
attaacagcg ttaccgataa cccgctgatt gatgttgata atcaggcaag ctatcatggt    1080
ggtaattttc tgggtcagta tgttggtatg ggtatggatc atctgcgcta ttatatcggt    1140
ctgctggcaa acatctgga tgttcagatt gcactgctgg catcaccgga atttagcaat    1200
ggtctgcctc cgagtctggt gggtaatcgt gaacgtaaag ttaatatggg tctgaaaggt    1260
ctgcagattt gcggtaatag cattatgccg ctgctgacct tttatggtaa tagtattgca    1320
gatcgttttc cgacccatgc cgaacaggca accagaata ttaacagcca gggttatacc    1380
agcgcaaccc tggcacgtcg tagcgttgat atttttcaga attatgttgc cattgccctg    1440
atgtttggtg ttcaggcagt tgatctgcgt acctacaaaa aaaccggtca ttatgatgca    1500
cgtgcccagc tgtcaccggc aaccgaacgt ctgtatagcg cagttcgtca tgttgttggt    1560
aaaaaaccga gctcagatcg tccgtatatt tggaatgata tgaacaggg tctggatgaa    1620
catattgcac gtattagtgc agatattgca gccggtggtg ttattgttca ggccgttcag    1680
gacattctgc cgccgctgca t                                              1701

<210> SEQ ID NO 6
<211> LENGTH: 567
<212> TYPE: PRT
<213> ORGANISM: Artificial Sequence
<220> FEATURE:
<223> OTHER INFORMATION: Variant of PAL from Anabaena variabilis

<400> SEQUENCE: 6

Met Lys Thr Leu Ser Gln Ala Gln Ser Lys Thr Ser Ser Gln Gln Phe
 1               5                  10                  15

Ser His Thr Gly Asn Ser Ser Ala Asn Val Ile Ile Gly Asn Gln Lys
```

```
                    20                  25                  30
Leu Thr Ile Asn Asp Val Val Arg Val Ala Arg Asn Gly Thr Ala Val
                35                  40                  45
Ser Leu Thr Asn Asn Lys Asp Ile Leu Gln Arg Ile Gln Ala Ser Cys
         50                  55                  60
Asp Tyr Ile Asn Asn Ala Val Glu Lys Gly Glu Pro Ile Tyr Gly Val
 65                  70                  75                  80
Thr Ser Gly Phe Gly Gly Met Ala Asn Val Val Ile Ser Arg Glu Gln
                 85                  90                  95
Ala Ser Glu Leu Gln Thr Asn Leu Val Trp Phe Leu Lys Thr Gly Ala
                100                 105                 110
Gly Asn Lys Leu Pro Leu Ala Asp Val Arg Ala Ala Met Leu Leu Arg
                115                 120                 125
Ala Asn Ser His Met Arg Gly Ala Ser Gly Ile Arg Leu Glu Leu Ile
                130                 135                 140
Lys Arg Met Glu Ile Phe Leu Asn Ala Gly Val Thr Pro Tyr Val Tyr
145                 150                 155                 160
Glu Phe Gly Ser Ile Gly Ala Ser Gly Asp Leu Val Pro Leu Ser Tyr
                165                 170                 175
Ile Thr Gly Ser Leu Ile Gly Leu Asp Pro Ser Phe Lys Val Asp Phe
                180                 185                 190
Asn Gly Lys Glu Met Asp Ala Pro Thr Ala Leu Arg Gln Leu Asn Leu
                195                 200                 205
Ser Pro Leu Thr Leu Gln Pro Lys Glu Gly Leu Ala Met Met Asn Gly
                210                 215                 220
Thr Ser Val Met Thr Gly Ile Ala Ala Asn Cys Val Tyr Asp Thr Gln
225                 230                 235                 240
Ile Leu Thr Ala Ile Ala Met Gly Val His Ala Leu Asp Ile Gln Ala
                245                 250                 255
Leu Asn Gly Thr Asn Gln Ser Phe His Pro Phe Ile His Asn Ser Lys
                260                 265                 270
Pro His Pro Gly Gln Leu Trp Ala Ala Asp Gln Met Ile Ser Leu Leu
                275                 280                 285
Ala Gly Ser Gln Leu Val Arg Asp Glu Leu Asp Gly Lys His Asp Tyr
                290                 295                 300
Met Asp Gly Glu Leu Ile Gln Asp Arg Tyr Ser Leu Arg Cys Leu Pro
305                 310                 315                 320
Gln Tyr Leu Gly Pro Ile Val Asp Gly Ile Ser Gln Ile Ala Lys Gln
                325                 330                 335
Ile Glu Ile Glu Ile Asn Ser Val Thr Asp Asn Pro Leu Ile Asp Val
                340                 345                 350
Asp Asn Gln Ala Ser Tyr His Gly Gly Asn Phe Leu Gly Gln Tyr Val
                355                 360                 365
Gly Met Gly Met Asp His Leu Arg Tyr Tyr Ile Gly Leu Leu Ala Lys
                370                 375                 380
His Leu Asp Val Gln Ile Ala Leu Leu Ala Ser Pro Glu Phe Ser Asn
385                 390                 395                 400
Gly Leu Pro Pro Ser Leu Val Gly Asn Arg Glu Arg Lys Val Asn Met
                405                 410                 415
Gly Leu Lys Gly Leu Gln Ile Cys Gly Asn Ser Ile Met Pro Leu Leu
                420                 425                 430
Thr Phe Tyr Gly Asn Ser Ile Ala Asp Arg Phe Pro Thr His Ala Glu
                435                 440                 445
```

```
Gln Ala Asn Gln Asn Ile Asn Ser Gln Gly Tyr Thr Ser Ala Thr Leu
    450                 455                 460
Ala Arg Arg Ser Val Asp Ile Phe Gln Asn Tyr Val Ala Ile Ala Leu
465                 470                 475                 480
Met Phe Gly Val Gln Ala Val Asp Leu Arg Thr Tyr Lys Lys Thr Gly
                485                 490                 495
His Tyr Asp Ala Arg Ala Gln Leu Ser Pro Ala Thr Glu Arg Leu Tyr
            500                 505                 510
Ser Ala Val Arg His Val Val Gly Lys Lys Pro Ser Ser Asp Arg Pro
        515                 520                 525
Tyr Ile Trp Asn Asp Asn Glu Gln Gly Leu Asp Glu His Ile Ala Arg
    530                 535                 540
Ile Ser Ala Asp Ile Ala Ala Gly Gly Val Ile Val Gln Ala Val Gln
545                 550                 555                 560
Asp Ile Leu Pro Pro Leu His
                565

<210> SEQ ID NO 7
<211> LENGTH: 1701
<212> TYPE: DNA
<213> ORGANISM: Artificial Sequence
<220> FEATURE:
<223> OTHER INFORMATION: Variant of PAL from Anabaena variabilis

<400> SEQUENCE: 7
atgaaaaccc tgagtcaggc acagagcaaa accagcagcc agcagtctag ccataccggc      60
aatagcagcg caaatgtgat tattggtaat cagaaactga ccatcaatga tgttgtacgt     120
gttgcccgta atggcaccgc ggttagcctg accaataata aagatattct gcagcgtatt     180
caggccagct gtgattatat caataatgca gttgaaaaag gtgaaccgat ttatggtgtt     240
accagcggtt ttggtggtat ggcaaatgtt gtaattagcc gtgaacaggc aagcgaactg     300
cagaccaatc tggtttggtt tctgaaaacc ggtgcaggta taaaactgcc gctggcagat     360
gttcgtgcag caatgctgct gcgtgcaaat agccacatgc gtggtgcaag cggtattcgt     420
ctggaactga ttaaacgcat ggaaatcttt ctgaatgccg tgttaccccg tatgttttat     480
gaatttggta gcattggtgc cagcggtgat ctggttccgc tgagctatat taccggtagc     540
ctgattggcc tggaccccga gctttaaagtt gattttaatg caaagaaat ggacgcaccg     600
accgcactgc gtcagctgaa tctgagtccg ctgaccctgc agccgaaaga aggtctggca     660
atgatgaatg gcaccagcgt tatgaccggt attgcagcaa attgtgttta tgataccag     720
attctgaccg caattgcaat gggtgttcat gcactggata ttcaggcact gaatggtaca     780
aatcagagct tcatccgtt tatccataac agcaaaccgc atccgggtca gctgtgggca     840
gcagatcaga tgattagcct gctggccggt agccagctgg ttcgtgatga actggatggt     900
aaacatgatt atatggatgg tgaactgatc caggatcgtt atagcctgcg ttgtctgccg     960
cagtatctgg gtccgattgt tgatggtatt agccagattg ccaaacaaat cgaaattgag    1020
attaacagcg ttaccgataa cccgctgatt gatgttgata tcaggcaag ctatcatggt    1080
ggtaattttc tgggtcagta tgttggtatg ggtatggatc tctgcgcta ttatatcggt    1140
ctgctggcaa acatctgga tgttcagatt gcactgctgg catcaccgga atttagcaat    1200
ggtctgccte cgagtctggt gggtaatcgt gaacgtaaag ttaatatggg tctgaaaggt    1260
ctgcagattt gcggtaatag cattatgccg ctgctgacct ttatggtaa tagtattgca    1320
```

-continued

```
gatcgttttc cgacccatgc cgaacaggca aaccagaata ttaacagcca gggttatacc    1380
agcgcaaccc tggcacgtcg tagcgttgat attttcaga attatgttgc cattgccctg     1440
```
```
atgtttggtg ttcaggcagt tgatctgcgt acctacaaaa aaaccggtca ttatgatgca    1500
cgtgcccagc tgtcaccggc aaccgaacgt ctgtatagcg cagttcgtca tgttgttggt    1560
aaaaaaccga gctcagatcg tccgtatatt tggaatgata atgaacaggg tctggatgaa    1620
catattgcac gtattagtgc agatattgca gccggtggtg ttattgttca ggccgttcag    1680
gacattctgc cgccgctgca t                                              1701
```

<210> SEQ ID NO 8
<211> LENGTH: 567
<212> TYPE: PRT
<213> ORGANISM: Artificial Sequence
<220> FEATURE:
<223> OTHER INFORMATION: Variant of PAL from Anabaena variabilis

<400> SEQUENCE: 8

```
Met Lys Thr Leu Ser Gln Ala Gln Ser Lys Thr Ser Ser Gln Gln Ser
1               5                   10                  15

Ser His Thr Gly Asn Ser Ser Ala Asn Val Ile Ile Gly Asn Gln Lys
            20                  25                  30

Leu Thr Ile Asn Asp Val Val Arg Val Ala Arg Asn Gly Thr Ala Val
        35                  40                  45

Ser Leu Thr Asn Asn Lys Asp Ile Leu Gln Arg Ile Gln Ala Ser Cys
    50                  55                  60

Asp Tyr Ile Asn Asn Ala Val Glu Lys Gly Glu Pro Ile Tyr Gly Val
65                  70                  75                  80

Thr Ser Gly Phe Gly Gly Met Ala Asn Val Val Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Gln Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Gly Ser Gln Leu Val Arg Asp Glu Leu Asp Gly Lys His Asp Tyr
```

```
        290                 295                 300
Met Asp Gly Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
385                 390                 395                 400

Gly Leu Pro Pro Ser Leu Val Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Ala Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Gln Leu Ser Pro Ala Thr Glu Arg Leu Tyr
            500                 505                 510

Ser Ala Val Arg His Val Val Gly Lys Lys Pro Ser Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Pro Leu His
                565
```

<210> SEQ ID NO 9
<211> LENGTH: 1701
<212> TYPE: DNA
<213> ORGANISM: Artificial Sequence
<220> FEATURE:
<223> OTHER INFORMATION: Variant of PAL from Anabaena variabilis

<400> SEQUENCE: 9

```
atgaaaaccc tgagtcaggc acagagcaaa accagcagcc agcagtctag ccataccggc    60
aatagcagcg caaatgtgat tattggtaat cagaaactga ccatcaatga tgttgtacgt   120
gttgcccgta atggcaccgc ggttagcctg accaataata aagatattct gcagcgtatt   180
caggccagct gtgattatat caataatgca gttgaaaaag gtgaaccgat ttatggtgtt   240
accagcggtt ttggtggtat ggcaaatgtt gtaattagcc gtgaacaggc aagcgaactg   300
cagaccaatc tggtttggtt tctgaaaacc ggtgcaggta taaactgcc gctggcagat   360 gttcgtgcag caatgctgct gcgtgcaaat agccacatgc gtggtgcaag cggtattcgt   420
ctggaactga ttaaacgcat ggaaatcttt ctgaatgccg gtgttacccc gtatgtttat   480
```

-continued

```
gaatttggta gcattggtgc cagcggtgat ctggttccgc tgagctatat taccggtagc    540
ctgattggcc tggacccgag ctttaaagtt gattttaatg caaagaaat ggacgcaccg    600 accgcactga gacagctgaa tctgccgccg ctgaccctgc agccgaaaga aggtctggca    660
atgatgaatg gcaccagcgt tatgaccggt attgcagcaa attgtgttta tgatacccag    720
attctgaccg caattgcaat gggtgttcat gcactggata ttcaggcact gaatggtaca    780
aatcagagct ttcatccgtt tatccataac agcaaaccgc atccgggtca gctgtgggca    840
gcagatcaga tgctaagcct gctggccggt agccagctgg ttcgtgatga actggatggt    900
aaacatgatt atatggatgg tgaactgatc caggatcgtt atagcctgcg ttgtctgccg    960
cagtatctgg gtccgattgt tgatggtatt agccagattg ccaaacaaat cgaaattgag    1020
attaacagcg ttaccgataa cccgctgatt gatgttgata tcaggcaag ctatcatgtt    1080 ggtaattttc atggtcagta tgttggtatg ggtatggatc atctgcgcta ttatatcggt    1140
ctgctggcaa acatctgga tgttcagatt gcactgctgg catcaccgga atttagcaat    1200
ggtctgcctc cgagtctggt gggtaatcgt gaacgtaaag ttaatatggg tctgaaaggt    1260
ctgcagattt gcggtaatag cattatgccg ctgctgacct tttatggtaa tagtattgca    1320
gatcgttttc cgacccatgc cgaacaggca aaccagaata ttaacagcca gggttatacc    1380
agcgcaaccc tggcacgtcg tagcgttgaa attttcaga attatgttgc cattgccctg    1440
atgtttggtg ttcaggcagt tgatctgcgt acctacaaaa aaaccggtca ttatgatgca    1500
cgtgcccagc tgtcaccggc aaccgaacgt ctgtatagcg cagttcgtca tgttgttggt    1560
aaaaaaccga gctcagatcg tccgtatatt tggaatgata tgaacaggg tctggatgaa    1620 catattgcac gtattagtgc agatattgca gccggtggtg ttattgttca ggccgttcag    1680
gacattctgc cgccgctgca t                                              1701
```

<210> SEQ ID NO 10
<211> LENGTH: 567
<212> TYPE: PRT
<213> ORGANISM: Artificial Sequence
<220> FEATURE:
<223> OTHER INFORMATION: Variant of PAL from Anabaena variabilis

<400> SEQUENCE: 10

```
Met Lys Thr Leu Ser Gln Ala Gln Ser Lys Thr Ser Ser Gln Gln Ser
1               5                   10                  15

Ser His Thr Gly Asn Ser Ser Ala Asn Val Ile Ile Gly Asn Gln Lys
                20                  25                  30

Leu Thr Ile Asn Asp Val Val Arg Val Ala Arg Asn Gly Thr Ala Val
            35                  40                  45

Ser Leu Thr Asn Asn Lys Asp Ile Leu Gln Arg Ile Gln Ala Ser Cys
        50                  55                  60

Asp Tyr Ile Asn Asn Ala Val Glu Lys Gly Glu Pro Ile Tyr Gly Val
65                  70                  75                  80

Thr Ser Gly Phe Gly Gly Met Ala Asn Val Val Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140
```

```
Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
                180                 185                 190

Asn Gly Lys Glu Met Asp Ala Pro Thr Ala Leu Arg Gln Leu Asn Leu
                195                 200                 205

Pro Pro Leu Thr Leu Gln Pro Lys Glu Gly Leu Ala Met Met Asn Gly
210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
                260                 265                 270

Pro His Pro Gly Gln Leu Trp Ala Ala Asp Gln Met Leu Ser Leu Leu
                275                 280                 285

Ala Gly Ser Gln Leu Val Arg Asp Glu Leu Asp Gly Lys His Asp Tyr
                290                 295                 300

Met Asp Gly Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
                340                 345                 350

Asp Asn Gln Ala Ser Tyr His Gly Gly Asn Phe His Gly Gln Tyr Val
                355                 360                 365

Gly Met Gly Met Asp His Leu Arg Tyr Tyr Ile Gly Leu Leu Ala Lys
                370                 375                 380

His Leu Asp Val Gln Ile Ala Leu Leu Ala Ser Pro Glu Phe Ser Asn
385                 390                 395                 400

Gly Leu Pro Pro Ser Leu Val Gly Asn Arg Glu Arg Lys Val Asn Met
                405                 410                 415

Gly Leu Lys Gly Leu Gln Ile Cys Gly Asn Ser Ile Met Pro Leu Leu
                420                 425                 430

Thr Phe Tyr Gly Asn Ser Ile Ala Asp Arg Phe Pro Thr His Ala Glu
                435                 440                 445

Gln Ala Asn Gln Asn Ile Asn Ser Gln Gly Tyr Thr Ser Ala Thr Leu
                450                 455                 460

Ala Arg Arg Ser Val Glu Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Gln Leu Ser Pro Ala Thr Glu Arg Leu Tyr
                500                 505                 510

Ser Ala Val Arg His Val Val Gly Lys Lys Pro Ser Ser Asp Arg Pro
                515                 520                 525

Tyr Ile Trp Asn Asp Asn Glu Gln Gly Leu Asp Glu His Ile Ala Arg
                530                 535                 540

Ile Ser Ala Asp Ile Ala Ala Gly Gly Val Ile Val Gln Ala Val Gln
545                 550                 555                 560

Asp Ile Leu Pro Pro Leu His
```

<210> SEQ ID NO 11
<211> LENGTH: 1701
<212> TYPE: DNA
<213> ORGANISM: Artificial Sequence
<220> FEATURE:
<223> OTHER INFORMATION: Variant of PAL from Anabaena variabilis

<400> SEQUENCE: 11

```
atgaaaaccc tgagtcaggc tcagagcaaa accagcagcc agcagtctag ccataccggc      60
aatagcagcg caaatgtgat tattggtaat cagaaactga ccatcaatga tgttgtacgt     120
gttgcccgta atggcaccgc ggttagcctg accaataata aagatattct gcagcgtatt     180
caggccagct gtgattatat caataatgca gttgaaaaag gtgaaccgat ttatggtgtt     240
accagcggtt ttggtggtat ggcaaatgtt gtaattagcc gtgaacaggc aagcgaactg     300
cagaccaatc tggtttggtt tctgaaaacc ggtgcaggta taaactgcc gctggcagat     360
gttcgtgcag caatgctgct gcgtgcaaat agccacatgc gtggtgcaag cggtattcgt     420
ctggaactga ttaaacgcat ggaaatcttt ctgaatgccg tgttacccc gtatgtttat     480
gaatttggta gcattggtgc cagcggtgat ctggttccgc tgagctatat taccggtagc     540
ctgattggcc tggacccgag cttttaaagtt gattttaatg caaagaaat ggacgcaccg     600
accgcactga cacagctgaa tctgccgccg ctgaccctgc agccgaaaga aggtctggca     660
atgatgaatg gcaccagcgt tatgaccggt attgcagcaa attgtgttta tgatacccag     720
attctgaccg caattgcaat gggtgttcat gcactggata ttcaggcact gaatggtaca     780
aatcagagct ttcatccgtt tatccataac agcaaaccgc atccgggtca gctgtgggca     840
gcagatcaga tgctaagcct gctggccggt agccagctgg ttcgtgatga actggatggt     900
aaacatgatt atatggatgg tgaactgatc caggatcgtt atagcctgcg ttgtctgccg     960
cagtatctgg gtccgattgt tgatggtatt agccagattg ccaaacaaat cgaaattgag    1020
attaacagcg ttaccgataa cccgctgatt gatgttgata tcaggcaag ctatcatggt    1080
ggtaattttc atggtcagta tgttggtatg ggtatggatc atctgcgcta ttatatcggt    1140
ctgctggcaa acatctgga tgttcagatt gcactgctgg catcaccgga atttagcaat    1200
ggtctgcctc cgagtctggt gggtaatcgt gaacgtaaag ttaatatggg tctgaaaggt    1260
ctgcagattt gcggtaatag cattatgccg ctgctgacct tttatggtaa tagtattgca    1320
gatcgttttc cgacccatgc cgaacaggca aaccagaata ttaacagcca gggttatacc    1380
agcgcaaccc tggcacgtcg tagcgttgaa attttcaga attatgttgc cattgccctg    1440
atgtttggtg ttcaggcagt tgatctgcgt acctacaaaa aaaccggtca ttatgatgca    1500
cgtgcccagc tgtcaccggc aaccgaacgt ctgtatagcc agttcgtca tgttgttggt    1560
aaaaaaccga gctcagatcg tccgtatatt tggaatgata tgaacagggg tctggatgaa    1620
catattgcac gtattagtgc agatattgca gccggtggtg ttattgttca ggccgttcag    1680
gacattctgc cgccgctgca t                                              1701
```

<210> SEQ ID NO 12
<211> LENGTH: 567
<212> TYPE: PRT
<213> ORGANISM: Artificial Sequence
<220> FEATURE:
<223> OTHER INFORMATION: Variant of PAL from Anabaena variabilis

<400> SEQUENCE: 12

-continued

```
Met Lys Thr Leu Ser Gln Ala Gln Ser Lys Thr Ser Gln Gln Ser
1               5                   10                  15

Ser His Thr Gly Asn Ser Ser Ala Asn Val Ile Ile Gly Asn Gln Lys
            20                  25                  30

Leu Thr Ile Asn Asp Val Val Arg Val Ala Arg Asn Gly Thr Ala Val
                35                  40                  45

Ser Leu Thr Asn Asn Lys Asp Ile Leu Gln Arg Ile Gln Ala Ser Cys
    50                  55                  60

Asp Tyr Ile Asn Asn Ala Val Glu Lys Gly Glu Pro Ile Tyr Gly Val
65                  70                  75                  80

Thr Ser Gly Phe Gly Gly Met Ala Asn Val Val Ile Ser Arg Glu Gln
                85                  90                  95

Ala Ser Glu Leu Gln Thr Asn Leu Val Trp Phe Leu Lys Thr Gly Ala
                100                 105                 110

Gly Asn Lys Leu Pro Leu Ala Asp Val Arg Ala Ala Met Leu Leu Arg
            115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
                180                 185                 190

Asn Gly Lys Glu Met Asp Ala Pro Thr Ala Leu Arg Gln Leu Asn Leu
            195                 200                 205

Pro Pro Leu Thr Leu Gln Pro Lys Glu Gly Leu Ala Met Met Asn Gly
210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Leu Ser Leu Leu
    275                 280                 285

Ala Gly Ser Gln Leu Val Arg Asp Glu Leu Asp Gly Lys His Asp Tyr
290                 295                 300

Met Asp Gly Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
                340                 345                 350

Asp Asn Gln Ala Ser Tyr His Gly Gly Asn Phe His Gly Gln Tyr Val
            355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
385                 390                 395                 400

Gly Leu Pro Pro Ser Leu Val Gly Asn Arg Glu Arg Lys Val Asn Met
                405                 410                 415
```

-continued

```
Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Ala Asn Gln Asn Ile Asn Ser Gln Gly Tyr Thr Ser Ala Thr Leu
        450                 455                 460

Ala Arg Arg Ser Val Glu Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Gln Leu Ser Pro Ala Thr Glu Arg Leu Tyr
            500                 505                 510

Ser Ala Val Arg His Val Val Gly Lys Lys Pro Ser Ser Asp Arg Pro
        515                 520                 525

Tyr Ile Trp Asn Asp Asn Glu Gln Gly Leu Asp Glu His Ile Ala Arg
        530                 535                 540

Ile Ser Ala Asp Ile Ala Ala Gly Gly Val Ile Val Gln Ala Val Gln
545                 550                 555                 560

Asp Ile Leu Pro Pro Leu His
                565
```

ENGINEERED PHENYLALANINE AMMONIA LYASE POLYPEPTIDES

The present application claims priority U.S. Prov. Pat. Appln. Ser. No. 62/565,555 filed Sep. 29, 2017, and U.S. Prov. Pat. Appln. Ser. No. 62/458,232, filed Feb. 13, 2017, both of which are incorporated by reference in their entireties for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file CX7-159USP1-Substitute_ST25.txt, created on Mar. 21, 2018, with a size of 44 kilobytes, machine format IBM-PC, MS-Windows operating system, is hereby incorporated by reference.

FIELD OF THE INVENTION

The present invention provides engineered phenylalanine ammonia lyase (PAL) polypeptides and compositions thereof, as well as polynucleotides encoding the engineered phenylalanineammonia lyase (PAL) polypeptides. In some embodiments, the engineered PAL polypeptides are optimized to provide enhanced catalytic activity, as well as reduced sensitivity to proteolysis and increased tolerance to storage at elevated temperatures. In some embodiments the engineered PAL polypeptides contain fewer phenylalanine residues. The invention also relates to the use of the compositions comprising the engineered PAL polypeptides for therapeutic and industrial purposes.

BACKGROUND OF THE INVENTION

Phenylalanine ammonia lyase (PAL) along with histidine ammonia lyase (HAL) and tyrosine ammonia lyase (TAL) are members of the aromatic amino acid lyase family (EC 4.3.1.23-1.25 and 4.3.1.3). More specifically the enzymes having PAL activity (EC 4.3.1.23-1.25 and previously classified as EC4.3.1.5) catalyze the nonoxidative deamination of L-phenylalanine into (E)-cinnamic acid. PAL is a non-mammalian enzyme that is widely distributed in plants and has also been identified in fungi and a limited number of bacteria.

PAL enzymes may be used as a therapeutic protein for the treatment of the metabolic disorder, phenylalanine hydroxylase deficiency (PAHD), better known as phenylketonuria (PKU). PKU is an autosomal metabolic genetic disorder in which the hepatic enzyme phenylalanine hydroxylase (PAH) or one or more of the enzymes involved in the synthesis or recycling of the co-factor tetrahydrobiopterin, is partially functional or non-functional due to a mutation in the corresponding genes. This lack of functionality results in elevated levels of phenylalanine in the bloodstream. Depending on the type of mutation the concentration of phenylalanine in the blood stream of PKU patients is typically >360 µM. The phenylalanine is converted into phenylpyruvate (phenylketone) and other derivatives. In humans, if PKU is not treated early, high levels of phenylalanine and some of its breakdown products can cause significant medical problems including intellectual disability, microcephaly and seizures. Numerous studies have focused on the use of PAL in the treatment of PKU by enzyme substitution (Ambrus et al., Science 201:837-839 [1978]; Bourget et al., Appl. Biochem. Biotechnol., 10:57-59 [1984]; and Sarkissian et al., Proc. Natl. Acad. Sci. USA 96:2339-2344 [1999]).

SUMMARY OF THE INVENTION

The present invention provides engineered phenylalanine ammonia lyase (PAL) polypeptides and compositions thereof, as well as polynucleotides encoding the engineered phenylalanine ammonia lyase (PAL) polypeptides. In some embodiments, the engineered PAL polypeptides are optimized to provide enhanced catalytic activity, as well as reduced sensitivity to proteolysis and increased tolerance to storage at elevated temperatures. In some embodiments the engineered PAL polypeptides contain fewer phenylalanine residues. The invention also relates to the use of the compositions comprising the engineered PAL polypeptides for therapeutic and industrial purposes. In some embodiments, the present invention is directed to engineered phenylalanine ammonia lyase (PAL) polypeptides and biologically active fragments and analogs thereof having improved properties such an increased storage stability and/or reduced sensitivity to proteolysis.

The present invention is directed to engineered PAL polypeptides and biologically active fragments and analogs thereof having improved properties when compared to a wild-type PAL enzyme or a reference PAL polypeptide under essentially the same conditions. The invention is further directed to methods of using the engineered PAL polypeptides and biologically active fragments and analogs thereof in therapeutic and/or industrial compositions and methods of using such compositions for therapeutic and/or industrial purposes.

The present invention provides engineered polypeptides comprising amino acid sequences having at least 85%, 86%, 87%, 88%, 89%, 90%, 91%, 92%, 93%, 94%, 95%, 96%, 97%, 98%, 99% or more sequence identity to at least one of SEQ ID NO:4, 6, 8, 10, and/or 12, wherein the amino acid positions of the amino acid sequences are numbered with reference to the amino acid sequence of SEQ ID NO:2 or another amino acid sequence designated as a reference sequence. In some embodiments, the present invention provides engineered polypeptides comprising amino acid sequences having at least 85% or more sequence identity to at least one of SEQ ID NO:4, 6, 8, 10, and/or 12, wherein the amino acid positions of the amino acid sequences are numbered with reference to the amino acid sequence of SEQ ID NO:2 or another amino acid sequence designated as a reference sequence. In some embodiments, the present invention provides engineered polypeptides comprising amino acid sequences having at least 90% or more sequence identity to at least one of SEQ ID NO:4, 6, 8, 10, and/or 12, wherein the amino acid positions of the amino acid sequences are numbered with reference to the amino acid sequence of SEQ ID NO:2 or another amino acid sequence designated as a reference sequence. In some embodiments, the present invention provides engineered polypeptides comprising amino acid sequences having at least 95% or more sequence identity to at least one of SEQ ID NO:4, 6, 8, 10, and/or 12, wherein the amino acid positions of the amino acid sequences are numbered with reference to the amino acid sequence of SEQ ID NO:2 or another amino acid sequence designated as a reference sequence. In some embodiments, the present invention provides engineered polypeptides comprising amino acid sequences having at least 98% or more sequence identity to at least one of SEQ ID NO:4, 6, 8, 10, and/or 12, wherein the amino acid positions of the amino acid sequences are numbered with reference to the amino acid sequence of SEQ ID NO:2 or another amino acid sequence designated as a reference sequence. In some embodiments, the present invention provides engineered polypeptides comprising amino acid sequences comprising at least one of SEQ ID NO:4, 6, 8, 10, and/or 12, wherein the amino acid positions of the amino acid sequences are numbered with reference to the amino acid sequence of SEQ ID NO:2 or another amino acid sequence designated as a reference sequence.

The present invention also provides engineered polypeptides comprising at least one substitution or substitution set at one or more amino acid positions selected from 16, 16/150, 44/56, 44/56/102/239/285/469/470/495, 44/239, 44/239/285/469/495, 44/239/285/470, 44/239/469/470, 44/239/470/546, 44/239/495, 44/239/495/546, 44/469/470, 102, 102/470, 162, 165, 188, 239/285, 239/285/469, 239/469/470/495, 264, 267, 285/469/470/495, 285/470, 285/470/495, 364, 455, 469/470, 472, and 482, wherein the amino acid positions are numbered with reference to SEQ ID NO:6. In some additional embodiments, the engineered polypeptides comprise at least one substitution at one or more amino acid positions selected from 16, 264, 364, 472, 482, and/or any combinations thereof, wherein the amino acid positions are numbered with reference to SEQ ID NO:6. In some embodiments, the engineered polypeptides comprise at least one substitution or substitution set at one or more amino acid positions selected from 16, 16/150, 162, 188, 264, 267, 398, 434, 472, and 482, and/or any combinations thereof, wherein the amino acid positions are numbered with reference to SEQ ID NO:6.

The present invention also provides engineered polypeptides comprising at least one substitution or substitution set at one or more amino acid positions selected from 44/47/204/209/285, 44/47/364/470/495, 44/54/56/204/239/285/364/495, 44/54/56/204/239/470/495, 44/54/285/470, 44/102/285/364, 44/204/209/285, 44/204/285/364/470/495, 44/209/285/460/495, 44/285/364, 47/54/209, 47/204/209/239/285/495, 47/204/285/364/495, 47/209/239/364, 47/239/285/364, 47/470, 54, 54/56, 54/56/204/209/470, 54/56/204/209/495, 54/56/204/495, 54/56/209/562, 54/56/285/364/470, 54/56/285/470, 54/165/204/209/239/285/470/495, 54/239/495, 54/285/470, 54/470, 56, 165, 204, 204/209/239/285/470/495, 204/209/364, 204/209/364/495, 204/239, 204/239/285, 204/364, 204/470, 209/285/364/470, 209/285/364/470/495, 209/364, 209/364/495, 209/470, 239/364, 285/364, 285/364/495, 364, 364/470, 470, and 495, and/or any combinations thereof, wherein the amino acid positions are numbered with reference to SEQ ID NO:8.

The present invention also provides engineered polypeptides comprising at least one substitution or substitution set at one or more amino acid positions selected from 54/56/162/204/285, 54/56/162/204/398, 54/56/204/285, 54/56/204/398, 54/56/204/398/472, 54/56/285, 54/56/398, 54/56/398/472, 54/162/204/398, 54/162/398, 54/204/285/398/472, 54/204/398, 54/285/398, 54/285/398/472, 56/162/398, 56/204/285, 56/204/398, 56/204/398/460, 56/204/398/472, 56/285, 56/285/398/472, 56/398, 56/398/472, and 201/204/398, and/or any combinations thereof, wherein the amino acid positions are numbered with reference to SEQ ID NO:12. In some embodiments, the engineered polypeptides comprise at least one substitution or substitution set at one or more amino acid positions selected from 16, 18, 39, 47, 54, 59, 73, 91, 209, 214, 285, 290, 305, 307, 364, 407, 450, 470, 503, 521, 524, and 565, and/or any combinations thereof, wherein the amino acid positions are numbered with reference to SEQ ID NO:12.

The present invention also provides engineered polypeptides comprising at least one substitution or substitution set at one or more amino acid positions selected from 15/18/39/47/54/59/73/91/209/214/285/290/307/364/407/450/470/503/521/524/565, 16/18/19/214/407, 16/18/23/47/54/59/73/91/209/214/285/290/305/307/364/407/450/470/503/521/524/565, 16/18/39/43/44/59/209/503/565, 16/18/39/45/47/54/59/73/98/209/214/285/290/305/364/407/450/470/503/521/524/565, 16/18/39/47/49/54/59/73/209/285/290/305/307/364/450/470/503/521/524/565, 16/18/39/47/54/59/73/91/98/285/290/305/307/364/450/470/503/524/565, 16/18/39/47/54/59/73/91/209/214/285/290/305/307/313/364/450/503/521/524/565, 16/18/39/47/54/59/73/91/209/214/285/290/305/307/364/407/450/470/503/521/524, 16/18/39/47/54/59/73/91/209/214/285/290/305/307/364/407/450/470/503/521/524/565, 16/18/39/47/54/59/73/91/209/214/285/290/305/307/364/407/450/470/521/524/565, 16/18/39/47/54/59/73/91/209/214/285/290/305/307/364/407/450/503/521/524, 16/18/39/47/54/59/73/91/209/214/285/290/305/307/364/450/470/521/524/565, 16/18/39/47/54/59/73/91/209/214/285/290/305/364/407/450/503/521/524/565, 16/18/39/47/54/59/73/91/209/214/285/290/305/364/407/470/503/521/524, 16/18/39/47/54/59/73/91/209/214/285/290/307/364/407/450/470/503/521/524/565, 16/18/39/47/54/59/73/91/209/285/290/305/307/407/450/503/521/524/565, 16/18/39/47/54/59/73/91/209/285/290/307/364/407/470/503/521/524/565, 16/18/39/47/54/59/73/91/214/285/290/305/307/364/407/503, 16/18/39/47/54/59/73/91/285/290/305/307/364/407/450/470/503/521, 16/18/39/47/54/59/73/91/285/290/305/307/364/407/450/470/503/521/524/565, 16/18/39/47/54/59/73/91/285/290/305/364/407/470/503/521/524, 16/18/39/47/54/59/73/285/290/305/307/364/407/450/470/503/521/524/565, 16/18/39/47/54/59/91/98/209/285/290/305/307/364/407/450/470/503/521/524, 16/18/39/47/54/59/91/209/214/285/290/305/307/364/450/470/503/521/524/565, 16/18/39/47/54/59/91/214/285/290/305/307/364/407/450/470/503/521/524/565, 16/18/39/47/54/59/91/214/285/290/305/307/364/450/503/521/524, 16/18/39/47/54/59/91/285/290/305/307/364/407/450/503/521/524, 16/18/39/47/54/73/91/209/214/285/290/305/307/364/407/470/503/521/565, 16/18/39/47/54/73/91/209/285/290/305/307/364/407/450/470/503/521/524, 16/18/39/47/54/73/209/214/285/290/305/307/364/450/470/503/521/524/565, 16/18/39/47/54/91/214/285/290/305/364/407/450/470/503/521, 16/18/39/47/54/209/214/407/503/524/565, 16/18/39/47/59/73/91/214/290/305/307/364/407/450/470/503/521, 16/18/39/47/59/214/503/565, 16/18/39/47/91/290/407, 16/18/39/54/59/73/91/209/214/285/290/305/307/364/407/450/470/503/521/524, 16/18/39/54/59/73/209/214/285/290/364/407/450/470/503/521/524/565, 16/18/39/54/59/73/214/285/290/305/364/407/450/521/524/565, 16/18/39/54/73/91/209/210/285/290/307/364/407/450/470/503/521/524/565, 16/18/39/54/73/91/209/214/285/290/305/307/364/407/450/470/503/521/524, 16/18/39/54/73/98/214/285/290/305/307/364/407/470/503/521/524/565, 16/18/39/54/73/209/285/290/305/307/364/407/470/503/521/524/565, 16/18/39/54/91/214/285/290/364/450/470/503/521/524, 16/18/39/91/503/521, 16/18/47/54/59/73/91/98/285/290/364/407/450/470/503/521/524/565, 16/18/47/54/59/73/98/209/290/305/307/364/450/470/503/521/524/565, 16/18/47/54/59/73/209/285/290/305/307/364/450/470/503/521/524/565, 16/18/47/54/73/91/209/214/285/290/305/307/364/407/450/470/503/521/524/565, 16/18/47/59/285/407/450/565, 16/18/47/73/91/209/285/290/450/470/503/521/524, 16/18/47/73/214/307/503, 16/18/47/73/290/407/450, 16/18/47/209, 16/18/47/285/364/503/521, 16/18/47/364/407, 16/18/54/59/73/91/209/285/290/305/307/364/407/450/503/521, 16/18/54/59/290/407/

450/503/524, 16/18/54/73/91/214/285/290/407/561, 16/18/54/91/209/214/285/290/307/364/407/450/503/521/524/565, 16/18/54/407, 16/18/55/209/285/305, 16/18/59/209/450/503/524, 16/18/73/209/214/450, 16/18/91/209/407/503, 16/18/91/214/407/521/524/565, 16/18/209/450/503, 16/18/214/407/450/503, 16/18/285/290/470, 16/18/503, 16/22/214/503/524/565, 16/39/47/54/59/73/91/98/209/214/285/290/305/307/364/407/450/470/503/521/524/565, 16/39/47/54/59/73/91/98/209/214/285/290/307/364/407/450/470/521/524/565, 16/39/47/54/59/73/91/209/214/285/290/305/307/364/407/450/470/503/521/524, 16/39/47/54/59/73/91/209/214/285/290/305/307/364/407/450/470/503/521/524/565, 16/39/47/54/59/73/91/209/214/285/290/305/307/364/407/450/503/521/524/565, 16/39/47/54/59/73/91/209/214/285/290/305/307/364/407/470/503/521/524/565, 16/39/47/54/59/73/91/209/214/285/290/305/364/407/450/470/503/521/524, 16/39/47/54/59/73/91/209/214/285/290/305/364/407/450/503/521, 16/39/47/54/59/73/91/209/214/285/290/305/364/407/503/521/524/565, 16/39/47/54/59/73/91/209/214/285/290/307/450/470/503/521/524/565, 16/39/47/54/59/73/91/209/214/290/305/307/364/407/450/470/503/521/524/565, 16/39/47/54/59/73/91/209/214/290/305/407/450/470/503/521/524/565, 16/39/47/54/59/73/91/209/285/290/305/307/364/407/470/503/521/524, 16/39/47/54/59/73/91/214/285/290/305/307/364/450/470/503/521/524, 16/39/47/54/59/73/91/214/285/290/305/307/450/470/503/521/524/565, 16/39/47/54/59/73/91/214/285/290/305/364/407/450/503/524/565, 16/39/47/54/59/73/91/214/285/290/307/364/407/450/503/521/524/565, 16/39/47/54/59/73/91/214/290/364/407/450/470/524/565, 16/39/47/54/59/73/98/209/285/305/307/407/450/470/503/524, 16/39/47/54/59/73/285/290/305/307/364/407/524, 16/39/47/54/59/73/307/364/407/503/521/524, 16/39/47/54/59/214/364/450/470/503/521/524, 16/39/47/54/73/91/209/214/285/290/407/450/470/521/524/565, 16/39/47/54/73/91/209/307/364/407/470/503/521/524/565, 16/39/47/54/91/209/214/285/290/305/307/364/407/450/470/503/521/524, 16/39/47/54/209/214/285/290/305/307/364/470/503/521/524/565, 16/39/47/54/209/307/503, 16/39/47/59/73/209/214/285/290/305/307/364/407/450/470/503/524/565, 16/39/47/73/91/285/290/307/364/450/470/503/521/524/565, 16/39/47/73/209/214/285/290/305/307/364/407/450/470/503/521/524, 16/39/54/59/73/91/209/214/285/290/305/307/364/407/450/503/521/524/565, 16/39/54/59/73/91/214/285/290/305/307/364/407/450/503/521/524/565, 16/39/54/59/73/91/214/285/290/305/307/364/407/470/503/521, 16/39/54/59/73/91/214/290/305/307/407/470/503/521/524/565, 16/39/54/59/91/285/290/305/364/407/450/470/503/521/524/565, 16/39/55/59/503/565, 16/39/73/364, 16/39/214/255/407/565, 16/39/214/407/503/565, 16/39/214/524, 16/39/407/450/470/475, 16/39/521/565, 16/47/54/59/73/91/209/214/285/290/305/364/450/470/503/521/524/565, 16/47/54/59/73/91/209/214/285/290/305/450/470/503/524/565, 16/47/54/59/73/91/209/285/290/307/450/470/503/521/524/565, 16/47/54/59/91/290/305/307/364/407/450/470/503/521/524/565, 16/47/54/73/91/209/285/290/305/307/364/450/470/503/521/524/565, 16/47/54/91/209/470/524/565, 16/47/54/91/285/290/305/307/450/503/521/524/565, 16/47/54/214/290/364/407/503/521/524, 16/47/59/364/407/523, 16/47/59/524, 16/47/73/91/209/214/285/290/305/307/364/450/470/503/521/524/565, 16/47/73/91/214/285/407/565, 16/47/73/214/305/407/565, 16/47/91/214/307/407/470/503/565, 16/47/209/214/364/407/470/503/521/565, 16/47/407, 16/47/407/450/524, 16/47/450/470/565, 16/47/450/521, 16/54/59/73/91/209/214/285/290/307/450/470/503/524, 16/54/59/73/91/290/307/364/450/470/503/521/524/565, 16/54/59/91/209/364/407/450/521, 16/54/59/209/214/285/450, 16/54/59/214/565, 16/54/73/91/285/290/305/307/407/450/470/524, 16/54/73/407/450/470/503, 16/54/73/407/450/470/503/565, 16/59/73/91/370/503/524, 16/59/73/407/450/503/565, 16/59/73/503/565, 16/59/364/407/450/524, 16/73/91/209/470, 16/73/214/524, 16/91/209/214, 16/91/209/214/364/450, 16/91/214/407/503, 16/91/285/290/364/407/364/450, 16/209/214/407/503/524, 16/214/364/470, 16/214/407/565, 16/214/470, 16/290/305/364/407/470/479, 16/364/503/565, 16/407/470, 16/407/524/565, 16/450/470/524, 16/565, 18, 18/22/39/91/214/285/450/470/503, 18/39/47/54/59/73/91/98/209/214/285/290/305/307/364/407/450/470/503/521/524/565, 18/39/47/54/59/73/91/98/209/214/285/290/305/307/364/407/450/470/503/524, 18/39/47/54/59/73/91/98/214/285/290/305/307/364/450/470/503/524, 18/39/47/54/59/73/91/209/214/285/290/305/307/364/407/450/470/503/521/524, 18/39/47/54/59/73/91/209/214/285/290/305/307/364/407/450/470/503/524/565, 18/39/47/54/59/73/91/209/214/285/290/305/307/364/407/450/470/521/524/565, 18/39/47/54/59/73/91/209/214/285/290/305/307/364/407/450/503/521/524/565, 18/39/47/54/59/73/91/209/214/285/290/305/307/364/407/470/503/521/524, 18/39/47/54/59/73/91/209/214/285/290/305/307/364/407/503/521/524, 18/39/47/54/59/73/91/209/214/285/290/305/364/407/450/470/503/521/524, 18/39/47/54/59/73/91/209/214/285/290/305/307/364/407/450/470/503/521/524/565, 18/39/47/54/59/73/91/209/214/290/305/307/407/503/524/565, 18/39/47/54/59/73/91/209/214/290/307/364/407/450/470/503/521/524/565, 18/39/47/54/59/73/91/209/285/290/305/307/364/407/450/470/503, 18/39/47/54/59/73/91/209/290/307/364/407/470/503/521/565, 18/39/47/54/59/73/91/285/290/305/307/364/407/450/470/503/521/524/565, 18/39/47/54/59/73/91/285/290/305/307/364/407/450/470/503/524/565, 18/39/47/54/59/73/91/285/290/305/307/364/407/450/503/521/524, 18/39/47/54/59/73/91/285/290/307/364/450/470/503/524, 18/39/47/54/59/73/209/214/285/290/305/307/364/407/450/503/521/565, 18/39/47/54/59/73/214/285/290/305/364/407/450/470/503/524, 18/39/47/54/59/91/98/209/285/290/305/307/364/407/450/470/503/521/524, 18/39/47/54/59/91/209/214/285/290/305/307/364/407/450/470/503/521/524/565, 18/39/47/54/59/91/209/214/290/305/307/364/407/470/503/521/524/565, 18/39/47/54/59/91/209/285/290/305/307/364/407/450/470/503/521/524, 18/39/47/54/59/209/214/285/290/305/307/364/407/450/470/503/521/565, 18/39/47/54/59/209/285/290/305/307/407/450/503/521/524, 18/39/47/54/59/214/470/503/521/524, 18/39/47/54/73/91/98/214/285/290/305/307/364/407/450/470/503/521/524/565, 18/39/47/54/73/91/98/285/290/305/450/503/521/524/565, 18/39/47/54/73/91/98/290/305/307/364/450/470/503/521/524, 18/39/47/54/73/91/154/209/290/305/307/364/407/450/470/503/521/524/565, 18/39/47/54/73/91/209/214/285/290/305/307/364/407/450/470/503/521/524, 18/39/47/54/73/91/209/214/285/290/305/307/450/503/521/524/565, 18/39/47/54/73/91/209/214/285/290/307/364/407/450/470/503/521/524/565, 18/39/47/54/73/91/209/214/285/290/307/364/407/450/470/503/565, 18/39/47/54/73/91/209/285/290/305/307/364/407/470/521/524/565, 18/39/47/54/73/91/209/305/364/407/450/470/503/521, 18/39/47/54/73/91/285/290/305/307/364/407/450/503/521/524, 18/39/47/54/91/214/285/290/305/307/407/450/503/521/524, 18/39/47/59/73/91/209/214/285/290/305/307/364/450/470/503/521/524/565, 18/39/47/59/73/91/214/285/307/364/450/470/503/521/524/565, 18/39/47/59/73/98/209/214/285/290/305/307/364/407/450/470/503/524, 18/39/47/73/91/209/214/290/305/307/364/450/470/503, 18/39/47/209/214/290/565, 18/39/54/59/73/91/98/209/214/285/290/305/307/364/407/521/524, 18/39/54/59/73/91/98/209/214/285/290/305/307/364/470/503/521/524/565, 18/39/54/59/73/91/209/214/285/290/305/307/364/407/450/470/503/521, 18/39/54/59/73/91/209/214/285/

290/305/307/364/407/450/470/503/521/524, 18/39/54/59/73/91/209/214/285/290/305/307/364/407/450/503/521/524, 18/39/54/59/73/91/209/214/285/290/307/364/407/450/470/503/521/524/565, 18/39/54/59/73/91/209/214/285/290/307/364/407/470/503/521, 18/39/54/59/73/91/209/214/285/305/307/364/407/450/470/503/521/524/565, 18/39/54/59/73/91/214/285/290/307/407/450/470/503/521/524/565, 18/39/54/59/73/91/285/290/305/307/364/407/450/470/503/521/524/565, 18/39/54/59/73/91/285/290/307/364/407/450/470/503/521/524/565, 18/39/54/59/73/285/290/307/364/470/503/521/524/565, 18/39/54/59/91/209/214/285/290/305/307/364/407/450/470/503/521/524/565, 18/39/54/59/285/290/305/307/364/407/450/470/503/524, 18/39/54/73/91/98/285/290/305/407/450/470/503/521/524/565, 18/39/54/73/91/209/285/290/305/307/364/407/450/470/503, 18/39/54/73/209/214/285/290/305/307/364/407/503/521/524, 18/39/55/407/470/503, 18/39/73/91/209/214/285/290/307/364/407/450/470/503/521/524/565, 18/39/73/91/214/285/290/305/364/407/450/470/503/521/524, 18/39/214/364/407/470/503, 18/39/214/364/450/470/521/524, 18/43/305/364/416/450, 18/47/54/59/73/91/209/214/290/305/364/407/450/503/524, 18/47/54/59/73/91/214/285/290/305/307/364/407/450/470/503/521/524, 18/47/54/59/73/91/214/285/290/307/364/407/485/503/524/565, 18/47/54/73/91/209/214/285/290/305/307/407/470/503/521/524, 18/47/54/73/91/209/285/290/364/407/450/470/503/521/524/565, 18/47/59/97/98/407/503, 18/47/59/214/285/565, 18/47/59/214/362/407, 18/47/59/214/450/521, 18/47/73/91/364/407/503, 18/47/97/98/182/209/364/407/503, 18/47/209/290/364/470, 18/47/209/407/450/470/503/521, 18/47/209/407/450/503, 18/47/214/285/287/290/470/503, 18/47/214/407/524/565, 18/47/364/470, 18/47/364/503, 18/47/364/503/565, 18/47/450/470, 18/47/521/565, 18/54/59/73/91/285/290/305/307/364/407/470/503/521/524, 18/54/73/214/307, 18/59/91/209/214/364, 18/59/91/565, 18/59/209, 18/59/305/364/470/565, 18/59/407/450, 18/59/503/524, 18/73/91/182/287/407/450/503, 18/73/285/364/407/470, 18/73/285/521/524, 18/73/364/450/565, 18/73/407, 18/91/209/364/407, 18/91/214, 18/91/214/407/524/565, 18/91/364/407, 18/91/364/407/450, 18/91/364/450/565, 18/91/407/470/521/524, 18/91/407/503, 18/209, 18/209/364/407/521/565, 18/214/364/407/470/503/524, 18/214/407, 18/290/565, 18/364/450/521/524/565, 18/364/503, 18/407/450/503/565, 18/450/503, 39/47/54/59/73/91/209/214/285/290/305/307/364/407/470/503/521/524/565, 39/47/54/59/73/91/209/214/285/290/305/364/407/503/521/524/565, 39/47/54/59/73/91/209/214/290/305/307/364/407/450/470/503, 39/47/54/59/73/91/209/214/290/305/307/364/407/470/503/521/524/565, 39/47/54/59/73/91/209/285/290/305/364/407/450/470/503/521/524/565, 39/47/54/59/73/91/209/285/290/307/407/450/470/503/521/565, 39/47/54/59/73/91/209/285/290/364/450/470/503/521/524, 39/47/54/59/73/91/214/285/290/305/307/407/412/450/470/503/521/524/565, 39/47/54/59/73/91/214/285/290/305/307/407/450/470/503/521/524/565, 39/47/54/59/73/91/214/285/290/364/450/470/503/521/524/565, 39/47/54/59/73/91/285/290/305/307/364/407/450/470/503/521/524/565, 39/47/54/59/73/91/285/290/305/307/364/407/470/503/521/524/565, 39/47/54/59/73/91/285/290/305/307/364/450/470/503/521/565, 39/47/54/59/73/91/285/290/305/307/407/450/470/503/521/524/565, 39/47/54/59/73/91/285/290/305/307/450/470/503/521/524, 39/47/54/59/73/209/214/285/290/307/407/450/503/521/524, 39/47/54/59/73/209/285/290/305/307/364/450/470/503/521/524, 39/47/54/59/91/98/209/214/285/290/305/307/364/407/450/503/521/524, 39/47/54/73/91/209/214/285/290/305/307/364/407/450/470/503/521/524/565, 39/47/54/73/91/209/214/285/290/305/307/407/450/470/503/521/524/565,

364/407/470/503/521/524, 39/47/54/73/91/209/285/290/305/364/450/470/503/521/524, 39/47/54/73/91/214/285/290/305/364/407/450/503/524, 39/47/54/73/91/285/290/305/307/364/407/450/470/503/521/524/565, 39/47/54/91/209/214/285/305/307/407/503/521/565, 39/47/54/91/209/285/290/307/364/407/450/470/503/521/524/565, 39/47/54/91/214/285/290/307/364/470/503/521/524, 39/47/59/73/91/209/214/285/290/305/307/364/407/450/470/503/521/524, 39/47/59/91/98/209/214/285/290/305/307/364/403/407/450/470/503/524/565, 39/47/59/91/209/214/285/290/305/307/364/450/470/503/521/524, 39/47/73/91/214/285/290/305/307/364/407/450/470/503/521/524/565, 39/47/73/91/214/285/290/305/364/407/450/503/521/524, 39/47/91/209/214/285/290/305/307/364/407/450/470/503/521/524/565, 39/47/91/214, 39/47/285/503, 39/54/59/73/91/209/214/285/290/305/307/364/407/450/470/503/521/524/565, 39/54/59/73/91/209/214/285/290/305/307/364/407/470/503, 39/54/59/73/91/209/214/285/290/364/407/470/503/524/565, 39/54/59/73/91/209/214/290/305/307/407/503/521/524/565, 39/54/59/73/91/209/214/290/305/407/450/503/524/565, 39/54/59/73/91/209/285/290/305/364/407/450/470/503/521/524/565, 39/54/59/73/91/285/290/307/364/407/450/470/503/524, 39/54/59/73/98/209/214/285/290/305/307/364/450/470/503, 39/54/59/73/209/214/285/290/305/307/364/407/450/503/521/565, 39/54/59/73/290/305/307/364/407/470/503/521/524/565, 39/54/59/91/98/209/287/290/291/307/364/407/450/470/521/524, 39/54/59/91/98/285/290/503/521/524/565, 39/54/59/91/209/214/285/290/305/307/364/407/450/470/503/524/565, 39/54/73/91/209/214/285/290/305/364/503/524/565, 39/59/73/209/285/290/305/307/364/407/450/470/503/521/524/565, 39/59/202/407/524/565, 39/59/364/450/470/565, 39/73/290/307/364/407/450/524/565, 39/209/214/407/450/470/503/521, 39/209/450/470/503, 39/214/285/290/305/307/364/503/521/524, 39/214/307/503/524, 47, 47/54/59/73/91/209/214/285/290/305/307/364/407/450/470/503/521/524/565, 47/54/59/73/91/209/285/290/305/307/364/407/450/470/503/521/524, 47/54/59/73/91/209/285/290/305/307/364/407/450/503/524/565, 47/54/59/73/91/285/290/311/364/407/503/521/524/565, 47/54/59/73/91/285/305/307/407/470/521/524, 47/54/59/73/98/209/214/285/290/305/307/364/407/450/470/503/521/524, 47/54/59/73/209/285/290/364/407/432/450/470/503/521/524/565, 47/54/73/91/209/214/285/290/305/307/364/407/450/470/503/521/524/565, 47/54/73/91/285/290/307/364/450/470/503/521/524/565, 47/54/91/97/209/364/503/565, 47/55, 47/59/91/407/470/503/565, 47/59/91/503/521, 47/59/209, 47/59/450/470/503, 47/73, 47/73/91/214, 47/73/91/285/290/305/307/364/450/470/503/521/524, 47/73/91/290/407/416/450/503/521/524, 47/73/209/364/450/521, 47/73/214/305/307/364/503/565, 47/73/214/305/407/503/565, 47/73/214/364/407, 47/73/407/470/503, 47/209/214/305/307/364/503/521/524, 47/209/503/524/565, 47/214/364/503, 47/214/407, 47/285/290/364/503/565, 47/305, 47/364/407/470/521/524, 47/364/524/565, 47/407, 47/407/450/521/524, 47/407/565, 47/524/565, 51/407/470/503/524, 54/59/73/91/214/285/290/364/407/470/503/524/565, 54/59/91/209/407, 54/73/91/214/450/503/521/524, 54/73/91/305/364/407/450/470/503/521, 54/73/450, 54/209/285/290/305/307/364/407/450/470/503/565, 54/209/407/450/470/565, 54/209/470/503/524/565, 54/450, 54/503, 55/290/305/364/450/503, 59/73/290/407/503/554, 59/73/305/307/503, 59/91/407/450, 59/209/364/470/503, 59/214, 59/214/364/407/452/503, 59/214/450/503, 59/407/503/521/524, 59/450/503, 59/565, 73/91/214/524/565, 73/91/521, 91/97/209/285, 91/209/214/255/285/290/307/450, 91/209/214/364/407/450/470/565, 91/209/214/407/503/565, 91/209/214/450/521/524/565, 91/209/214/470/

565, 91/209/407, 91/214, 209, 209/214/305, 209/214/307/ 407/450/503, 209/214/407/450/470/503, 209/470, 214/285/ 307/503/565, 214/407/503/565, 214/470/503, 214/470/521, 290/470, 305/407/521, 364, 364/407/419/450/470/521/565, 364/407/565, 364/470/503/521/524, 407, 407/450/565, 407/ 503, 450/503, 450/524, 503, and 524, and/or any combinations thereof, wherein the amino acid positions are numbered with reference to SEQ ID NO:2.

In some embodiments, the engineered polypeptide is an *Anabaena variabilis* variant enzyme. In some additional embodiments, the engineered polypeptide of the present invention is more thermostable than wild-type *Anabaena variabilis* phenylalanine ammonia lyase. In some additional embodiments, the engineered polypeptide more resistant to proteolysis than wild-type *Anabaena variabilis* phenylalanine ammonia lyase. In yet some further embodiments, the engineered polypeptide is resistant to proteolysis by at least one digestive tract enzyme than wild-type *Anabaena variabilis* phenylalanine ammonia lyase. In still some further embodiments, the engineered polypeptide is more resistant to proteolysis by chymotrypsin, trypsin, carboxypeptidases, and/or elastases than wild-type *Anabaena variabilis* phenylalanine ammonia lyase. In yet some further embodiments, the engineered polypeptide is more acid stable than wild-type *Anabaena variabilis* phenylalanine ammonia lyase. In still additional embodiments, the engineered polypeptide is purified.

The present invention also provides engineered phenylalanine ammonia lyase polypeptides comprising amino acid sequences having at least 85%, 86%, 87%, 88%, 89%, 90%, 91%, 92%, 93%, 94%, 95%, 96%, 97%, 98%, 99% or more sequence identity to SEQ ID NO:2, 4, 6, 8, 10, and/or 12, or a functional fragment thereof. In some embodiments, the engineered phenylalanine ammonia lyase polypeptides comprise amino acid sequences having at least 90% sequence identity to SEQ ID NO:2, 4, 6, 8, 10, and/or 12, or a functional fragment thereof. In some additional embodiments, the engineered phenylalanine ammonia lyase polypeptides comprise an amino acid sequences having at least about 95% sequence identity to SEQ ID NO:2, 4, 6, 8, 10, and/or 12, or a functional fragment thereof. In some further embodiments, the engineered phenylalanine ammonia lyase polypeptide is a variant phenylalanine ammonia lyase polypeptide provided in any of Table 6.1, Table 7.1, Table 8.1, Table 9.1, Table 10.1, Table 14.1, and/or Table 15.1.

In some additional embodiments, the engineered phenylalanine ammonia lyase polypeptide is an *Anabaena variabilis* variant enzyme. In some additional embodiments, the engineered phenylalanine ammonia lyase polypeptide of the present invention is more thermostable than wild-type *Anabaena variabilis* phenylalanine ammonia lyase. In some additional embodiments, the engineered phenylalanine ammonia lyase polypeptide more resistant to proteolysis than wild-type *Anabaena variabilis* phenylalanine ammonia lyase. In yet some further embodiments, the engineered phenylalanine ammonia lyase polypeptide is resistant to proteolysis by at least one digestive tract enzyme, than wild-type *Anabaena variabilis* phenylalanine ammonia lyase. In still some further embodiments, the engineered phenylalanine ammonia lyase polypeptide is more resistant to proteolysis by chymotrypsin, trypsin, carboxypeptidases, and/or elastases than wild-type *Anabaena variabilis* phenylalanine ammonia lyase. In some additional embodiments, the engineered phenylalanine ammonia lyase polypeptide is more acid stable than wild-type *Anabaena variabilis* phenylalanine ammonia lyase. In some further embodiments, the engineered phenylalanine ammonia lyase polypeptide is purified.

The present invention also provides engineered polynucleotide sequences encoding at least one engineered polypeptide and/or phenylalanine ammonia lyase polypeptide provided herein. In some embodiments, the engineered polynucleotide encodes at least one engineered polypeptide provided herein. In some additional embodiments, the engineered polynucleotide encodes at least one engineered phenylalanine ammonia lyase polypeptide provided herein. In some embodiments, the engineered polynucleotide encodes an engineered polypeptide provided herein. In some additional embodiments, the engineered polynucleotide encodes an engineered phenylalanine ammonia lyase polypeptide provided herein. In some embodiments, the engineered polynucleotide sequence is operably linked to a control sequence. In some additional embodiments, the engineered polynucleotide sequence is codon-optimized.

The present invention also provides expression vectors comprising at least one engineered polynucleotide sequence provided herein. In some embodiments, the expression vectors comprise an engineered polynucleotide sequence provided herein. In some additional embodiments, the expression vectors further comprise at least one control sequence. In some additional embodiments, the expression vectors further comprise a control sequence. In some further embodiments, the control sequence comprises a promoter. In some embodiments, the promoter is a heterologous promoter.

The present invention also provides host cells transformed with at least one polynucleotide sequence provided herein. In some embodiments, the host cells are transformed with a polynucleotide sequence provide herein. In some additional embodiments, the host cells are *E. coli* cell.

The present invention also provides methods of producing an engineered polypeptide in a host cell comprising culturing a host cell comprising at least one polynucleotide encoding at least one engineered polypeptide provided herein, and/or at least one polynucleotide sequence provided herein, and/or at least one expression vector provided herein, under suitable culture conditions, such that at least one engineered polypeptide is produced. In some embodiments, the present invention also provides methods of producing an engineered phenylalanine ammonia lyase polypeptide in a host cell comprising culturing a host cell comprising at least one polynucleotide encoding at least one engineered phenylalanine ammonia lyase polypeptide provided herein, and/ or at least one polynucleotide sequence provided herein, and/or at least one expression vector provided herein, under suitable culture conditions, such that at least one engineered phenylalanine ammonia lyase polypeptide is produced. In some embodiments, the methods further comprise recovering at least one engineered polypeptide and/or phenylalanine ammonia lyase polypeptide provided herein from the culture and/or host cells. In some further embodiments, the methods further comprise the step of purifying at least one engineered polypeptide and/or phenylalanine ammonia lyase polypeptide provided herein.

The present invention also provides compositions comprising at least one engineered polypeptide provided herein. The present invention also provides compositions comprising at least one engineered phenylalanine ammonia lyase polypeptide provided herein. The present invention also provides compositions comprising an engineered phenylalanine ammonia lyase polypeptide provided herein.

The present invention also provides compositions comprising at least one engineered polynucleotide provided herein. In some embodiments, the compositions comprise an engineered polynucleotide provided herein. In some embodiments, the composition is a pharmaceutical composition. In some additional embodiments, the composition further comprises at least one pharmaceutically acceptable excipient and/or carrier. In some further embodiments, the composition is suitable for the treatment of phenylketonuria. In some additional embodiments, the composition is suitable for the treatment of elevated blood phenylalanine. In some embodiments, the composition is suitable for the treatment of hyperphenylalaninemia. In some additional embodiments, the composition is suitable for the treatment of tyrosinemia. In some further embodiments, the composition is suitable for the treatment of elevated blood tyrosine. In some embodiments, the composition is suitable for the treatment of hypertyrosinemia. In yet some additional embodiments, the composition is suitable for use in gene therapy. In some further embodiments, the composition is suitable for use in gene therapy to treat phenylketonuria, elevated blood phenylalanine, hyperphenylalaninemia, tyrosinemia, elevated blood tyrosinemia, and/or hypertyrosinemia. In yet some additional embodiments, the composition is suitable for use in mRNA therapy. In some further embodiments, the composition is suitable for use in mRNA therapy to treat phenylketonuria, elevated blood phenylalanine, hyperphenylalaninemia, tyrosinemia, elevated blood tyrosinemia, and/or hypertyrosinemia. In some embodiments, the composition is suitable for oral administration to a human. In some additional embodiments, the composition is in the form of a pill, tablet, capsule, gelcap, liquid, or emulsion. In some further embodiments, the pill, tablet, capsule, or gelcap further comprises an enteric coating. In some alternative embodiments, the composition is suitable for parenteral injection into a human. In yet some additional embodiments, the composition is coadministered with at least one additional therapeutically effective compound. In some other embodiments, the composition comprises at least one additional therapeutically effective compound.

The present invention also provides methods for treating and/or preventing the symptoms of phenylketonuria in a subject, comprising providing a subject having phenylketonuria, and providing at least one composition provided herein to a subject. In some embodiments, the phenylalanine concentration in the blood of the subject is reduced upon providing the composition to the subject. In some additional embodiments, the cinnamic acid concentration in the blood of the subject is increased upon providing the composition to the subject. In some further embodiments, the symptoms of phenylketonuria in the subject are ameliorated. In yet some additional embodiments, the subject is able to eat a diet that is less restricted in its phenylalanine content than diets required by subjects who have not been provided at least one pharmaceutical composition comprising at least one engineered phenylalanine ammonia lyase provided herein. In some embodiments, the subject is an infant, while in some other embodiments, the subject is a child, and in some other embodiments, the subject is a young adult, and in yet some additional embodiments, the subject is an adult.

The present invention also provides for the use of any of the compositions provided herein. In some embodiments, the compositions comprise at least one engineered phenylalanine ammonia lyase. In some embodiments, the ny of the compositions provided herein, alone or in any combination. It is not intended that the present invention be limited to any particular use.

DESCRIPTION OF THE INVENTION

Figure 1:
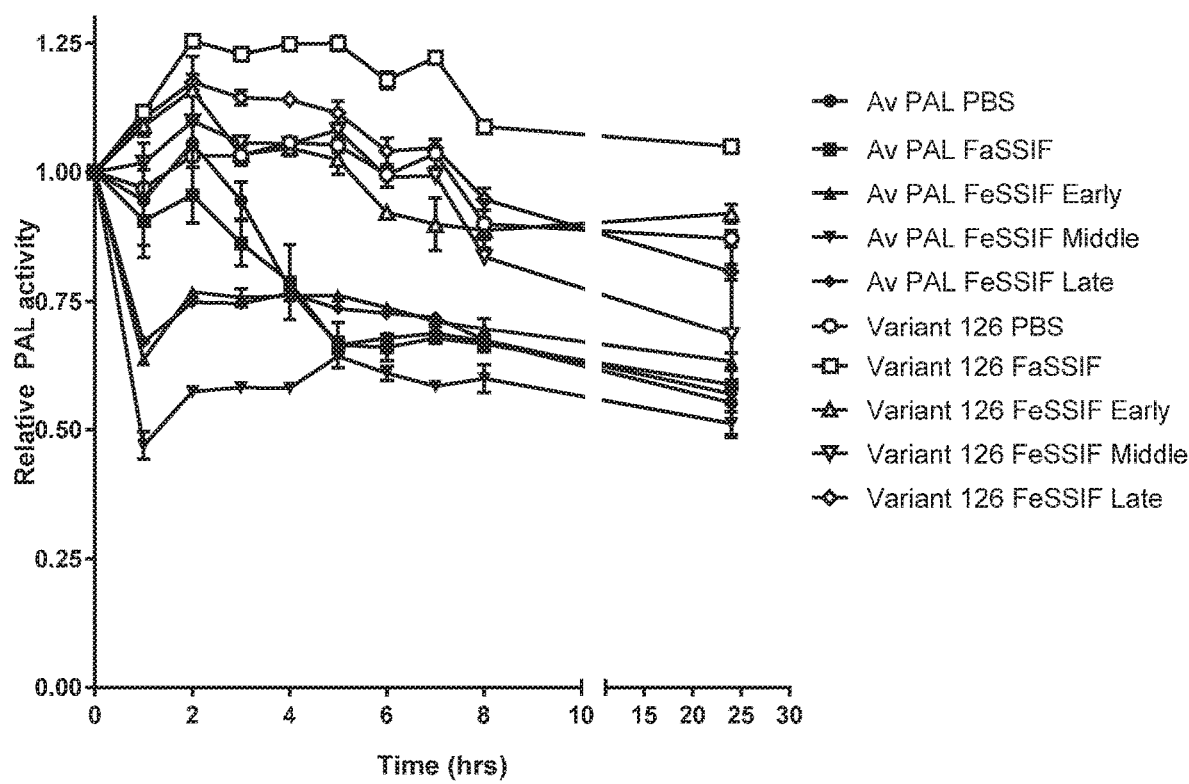
FIG. 1 is a graph showing the tolerance of AvPAL and Variant #126 to intestinal fluids without proteases. Residual PAL activity of wild-type AvPAL and Variant #126 are shown after incubation in fasted state simulated intestinal fluids (FaSSIF), early fed state simulated intestinal fluids (FeSSIF early), middle fed state simulated intestinal fluids (FeSSIF middle), and late fed state simulated intestinal fluids (FeSSIF late) in the absence of trypsin and chymotrypsin.
Figure 2:
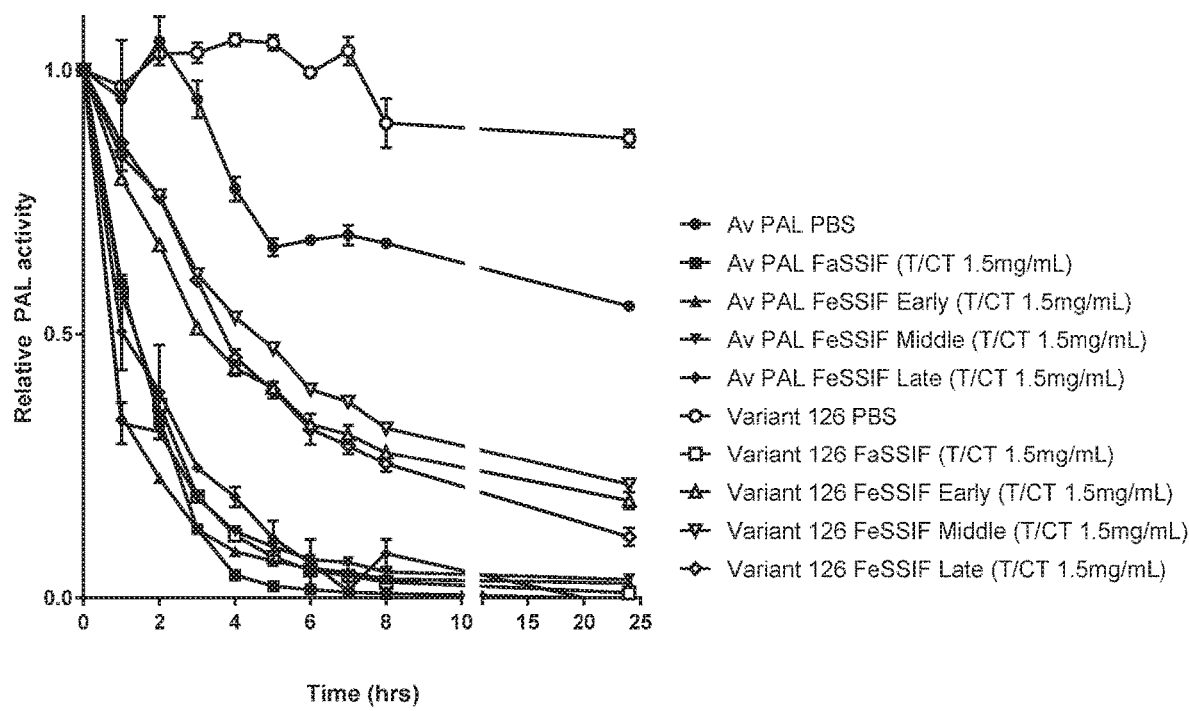
FIG. 2 is a graph showing the tolerance of AvPAL and Variant #126 to intestinal fluids with proteases. Residual PAL activity of AvPAL and Variant #126 are shown after incubation in fasted state simulated intestinal fluids (FaSSIF), early fed state simulated intestinal fluids (FeSSIF early), middle fed state simulated intestinal fluids (FeSSIF middle), and late fed state simulated intestinal fluids (FeSSIF late) in the presence of trypsin and chymotrypsin.

The present invention provides engineered PAL polypeptides, mutants, biologically active fragments and analogues thereof, and pharmaceutical and industrial compositions comprising the same.

The invention provides engineered phenylalanine ammonia lyase (PAL) polypeptides and compositions thereof, as well as polynucleotides encoding the engineered phenylalanine ammonia-lyase (PAL) polypeptides. In some embodiments, the engineered PAL polypeptides are optimized to provide enhanced catalytic activity, as well as reduced sensitivity to proteolysis and increased tolerance to storage at elevated temperatures. In some embodiments the engineered PAL polypeptides contain fewer phenylalanine residues. The present invention also provides methods for the use of compositions comprising the engineered PAL polypeptides for therapeutic and industrial purposes.

One method of detoxifying phenylalanine in the blood stream is the use of injectable recombinant PAL and PAL variants modified by pegylation (PEG-PAL). Pegylation has been shown to improve enzyme half-life and reduce subject antigenic response (See e.g., WO 2008/153776, WO 2011/097335, and U.S. Pat. No. 7,531,341). PAL variants useful in PEG-PAL compositions have been described as variants of wild-type *Nostoc punctiforme* (NpPAL); *Anabaena variabilis* (AvPAL) and *Rhodosporidium toruloides* (RtPAL). In particular, variants of wild-type AvPAL have been described wherein the cysteine residues at positions 64, 318, 503 and 565 have been substituted with serine (See e.g., U.S. Pat. Nos. 7,790,433; 7,560,263; and 7,537,923).

An alternative route of PAL administration as a means of reducing plasma concentration of L-phenylalanine in PKU subjects is a non-invasive formulation such as an oral formulation (Sarkissian et al., Proc. Natl. Acad. Sci. USA 96:2339-2344 [1999]). A key advantage of oral delivery of PAL is the reduced exposure of the enzyme to the immune system thereby minimizing the immune response which is observed with injectable PEG-PAL. However, a major limitation for the oral formulation of PAL is loss of enzyme activity in the stomach and intestinal lumen. In order to be effective and functional PAL must resist degradation by acidic pHs and proteases such as trypsin, chymotrypsin, carboxypeptidases and pepsin that normally degrade proteinaceous foods to oligopeptides and amino acids. In some previous studies (Sarkissian, supra) in order to achieve a significant effect for the oral administration of PAL, a large amount of the enzyme was required partly due to enzymatic degradation by proteases and partly due to relatively low specific activity at pH 7.0. Various means have been explored to suppress PAL degradation upon digestion (Kim et al., Molec. Therap., 10:220-224 [2004]; and Shah et al., Int. J. Pharmaceut., 356:61-68 [2008]).

One approach to increase the effectiveness of PAL under the harsh conditions of the digestive tract is to provide engineered PAL polypeptides that are tolerant to the inherent harsh conditions. Kang et al. used site directed mutagenesis of a chymotrypsin cleavage site and pegylation of surface lysines of an AvPAL to reduce proteolytic inactivation (See, Kang et al., Mol. Gen. Metabol., 99:4-9 [2010]). In these studies ten cleavage sites were specifically mutated and all but two of these resulting mutants (F18A and R94G) lost more than 50% of the original enzyme activity. None of the mutants showed increased activity and the F18A mutant showed a slight increase in trypsin resistance (Kang et al., supra). Further studies with PAL, while effective, generally have not resulted in a longer lived enzyme. Therefore, oral administration of PAL mutants previously described in the literature and derivatives thereof did not result in effective treatment of PKU.

Despite the progress made with various formulations of PAL there remains a need for PAL polypeptides having improved properties for oral administration. These improved properties include without limitation a greater half-life, increased catalytic activity, improved stability to the conditions in the digestive track as well as storage conditions, and reduced aggregation.

PAL enzymes may also find use as therapeutic proteins for the treatment of disorders of tyrosine metabolism, such as tyrosinemia Type I, tyrosinemia Type II, tyrosinemia Type III, and alkaptonuria. These disorders of tyrosine metabolism are autosomal metabolic genetic disorders in which one of the enzymes involved in the degradation of tyrosine is partially functional or non-functional due to a mutation in the corresponding gene. This lack of functionality results in elevated levels of tyrosine and other tyrosine-metabolites in the bloodstream. Because tyrosine is derived from phenylalanine, it is beneficial for patients with a disorder of tyrosine metabolism to limit phenylalanine and tyrosine intake. PAL enzymes are thus a potential treatment of disorders of tyrosine metabolism.

If patients with a disorder of tyrosine metabolism are not treated early, high levels of tyrosine and some of its breakdown products can cause significant medical problems including liver and kidney failure, liver cancer, intellectual disability, and even death.

In addition to therapeutic applications PAL enzymes may also be used in the industrial synthesis of L-phenylalanine and other substituted L-phenylalanine derivatives. These derivatives may then be used as pharmaceutical precursors (Gloge et al., Chem., 6: 3386-3390 [2000]; Bartsch et al., Prot. Eng. Des. Sel., 23:929-933 [2010]; and Turner, Curr. Opin. Chem. Biol., 234-240 [2011]). PAL enzymes may also be used in agricultural applications. PAL plays a significant role inbiosynthesis of phenylpropanoids (such as flavonoids and lignin) in plants, fungi and bacteria and can act as a defense related enzyme (Bate et al., Proc. Natl. Acad. Sci. USA 91:7608-7612 [1994]). Modulation of PAL activity by using recombinant polypeptides having PAL activity could potentially lead to effective herbicides.

Abbreviations and Definitions

Unless defined otherwise, all technical and scientific terms used herein generally have the same meaning as commonly understood by one of ordinary skill in the art to which this invention pertains. Generally, the nomenclature used herein and the laboratory procedures of cell culture, molecular genetics, microbiology, organic chemistry, analytical chemistry and nucleic acid chemistry described below are those well-known and commonly employed in the art. Such techniques are well-known and described in numerous texts and reference works well known to those of skill in the art. Standard techniques, or modifications thereof, are used for chemical syntheses and chemical analyses. All patents, patent applications, articles and publications mentioned herein, both supra and infra, are hereby expressly incorporated herein by reference.

Although any suitable methods and materials similar or equivalent to those described herein find use in the practice of the present invention, some methods and materials are described herein. It is to be understood that this invention is not limited to the particular methodology, protocols, and reagents described, as these may vary, depending upon the context they are used by those of skill in the art. Accordingly, the terms defined immediately below are more fully described by reference to the application as a whole. All patents, patent applications, articles and publications mentioned herein, both supra and infra, are hereby expressly incorporated herein by reference.

Also, as used herein, the singular "a", "an," and "the" include the plural references, unless the context clearly indicates otherwise.

Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

The term "about" means an acceptable error for a particular value. In some instances "about" means within 0.05%, 0.5%, 1.0%, or 2.0%, of a given value range. In some instances, "about" means within 1, 2, 3, or 4 standard deviations of a given value.

Furthermore, the headings provided herein are not limitations of the various aspects or embodiments of the invention which can be had by reference to the application as a whole. Accordingly, the terms defined immediately below are more fully defined by reference to the application as a whole. Nonetheless, in order to facilitate understanding of the invention, a number of terms are defined below.

Unless otherwise indicated, nucleic acids are written left to right in 5' to 3' orientation; amino acid sequences are written left to right in amino to carboxy orientation, respectively.

As used herein, the term "comprising" and its cognates are used in their inclusive sense (i.e., equivalent to the term "including" and its corresponding cognates).

"EC" number refers to the Enzyme Nomenclature of the Nomenclature Committee of the International Union of Biochemistry and Molecular Biology (NC-IUBMB). The IUBMB biochemical classification is a numerical classification system for enzymes based on the chemical reactions they catalyze.

"ATCC" refers to the American Type Culture Collection whose biorepository collection includes genes and strains.

"NCBI" refers to National Center for Biological Information and the sequence databases provided therein.

As used herein, the term "phenylalanine ammonia lyase (PAL) polypeptide" refers to a class of enzymes within the aromatic amino acid lyase family (EC 4.3.1.23, EC 4.3.1.24 and EC4.3.1.25) which also includes histidine ammonia lyase, and tyrosine ammonia lyase. The PAL polypeptides are also sometimes referred to as phenylalanine/tyrosine ammonia lyases because some PAL enzymes may use tyrosine as well as phenylalanine as a substrate. However, the AvPAL and variants disclosed and claimed herein do not use tyrosine as a substrate. PAL polypeptides catalyze the conversion of L-phenylalanine to trans-cinnamic acid and ammonia. PAL activity refers to the enzymatic activity of PAL polypeptides. In some preferred embodiments, a PAL enzyme also contains the cofactor 3,5-dihydro-5-methylidene-4H-imidazol-4-one (MIO). This cofactor maybe required for catalytic activity and is formed by cyclization and dehydration of a conserved active site Ala167-Ser168-Gly169 tripeptide segment.

"Protein," "polypeptide," and "peptide" are used interchangeably herein to denote a polymer of at least two amino acids covalently linked by an amide bond, regardless of length or post-translational modification (e.g., glycosylation or phosphorylation).

"Polynucleotide" is used herein to denote a polymer comprising at least two nucleotides where the nucleotides are either deoxyribonucleotides or ribonucleotides.

"Amino acids" are referred to herein by either their commonly known three-letter symbols or by the one-letter symbols recommended by IUPAC-IUB Biochemical Nomenclature Commission. Nucleotides, likewise, may be referred to by their commonly accepted single letter codes.

The term "engineered," "recombinant," "non-naturally occurring," and "variant," when used with reference to a cell, a polynucleotide or a polypeptide refers to a material or a material corresponding to the natural or native form of the material that has been modified in a manner that would not otherwise exist in nature or is identical thereto but produced or derived from synthetic materials and/or by manipulation using recombinant techniques.

As used herein, "wild-type" and "naturally-occurring" refer to the form found in nature. For example a wild-type polypeptide or polynucleotide sequence is a sequence present in an organism that can be isolated from a source in nature and which has not been intentionally modified by human manipulation.

"Coding sequence" refers to that part of a nucleic acid (e.g., a gene) that encodes an amino acid sequence of a protein.

The term "percent (%) sequence identity" is used herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman (Smith and Waterman, Adv. Appl. Math., 2:482 [1981]), by the homology alignment algorithm of Needleman and Wunsch (Needleman and Wunsch, J. Mol. Biol., 48:443 [1970]), by the search for similarity method of Pearson and Lipman (Pearson and Lipman, Proc. Natl. Acad. Sci. USA 85:2444 [1988]), by computerized implementations of these algorithms (e.g., GAP, BESTFIT, FASTA, and TFASTA in the GCG Wisconsin Software Package), or by visual inspection, as known in the art. Examples of algorithms that are suitable for determining percent sequence identity and sequence similarity include, but are not limited to the BLAST and BLAST 2.0 algorithms (See e.g., Altschul et al., J. Mol. Biol., 215: 403-410 [1990]; and Altschul et al., Nucleic Acids Res., 3389-3402 [1977]). Software for performing BLAST analyses is publicly available through the National Center for Biotechnology Information website. This algorithm involves first identifying high scoring sequence pairs (HSPs) by identifying short words of length "W" in the query sequence, which either match or satisfy some positive-valued threshold score "T," when aligned with a word of the same length in a database sequence. T is referred to as the neighborhood word score threshold (See, Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters "M" (reward score for a pair of matching residues; always >0) and "N" (penalty score for mismatching residues; always <0). For amino acid sequences, a scoring matrix is used to calculate the cumulative score. Extension of the word hits in each direction are halted when: the cumulative alignment score falls off by the quantity "X" from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (See e.g., Henikoff and Henikoff, Proc. Natl. Acad. Sci. USA 89:10915 [1989]). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, at least 100 residues in length or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides or polypeptides over a "comparison window" to identify and compare local regions of sequence similarity. In some embodiments, a "reference sequence" can be based on a primary amino acid sequence, where the reference sequence is a sequence that can have one or more changes in the primary sequence. For instance, the phrase "reference sequence based on SEQ ID NO:4 having a valine at the residue corresponding to X39" refers to a reference sequence in which the corresponding residue at position X39 in SEQ ID NO:4 (e.g., an alanine), has been changed to valine.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Corresponding to", "reference to," and "relative to" when used in the context of the numbering of a given amino acid or polynucleotide sequence refer to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered PAL, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Amino acid difference" and "residue difference" refer to a difference in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X91 as compared to SEQ ID NO:4" refers to a difference of the amino acid residue at the polypeptide position corresponding to position 91 of SEQ ID NO:4. Thus, if the reference polypeptide of SEQ ID NO:4 has a alanine at position 91, then a "residue difference at position X91 as compared to SEQ ID NO:4" refers to an amino acid substitution of any residue other than alanine at the position of the polypeptide corresponding to position 91 of SEQ ID NO:4. In most instances herein, the specific amino acid residue difference at a position is indicated as "XnY" where "Xn" specified the corresponding residue and position of the reference polypeptide (as described above), and "Y" is the single letter identifier of the amino acid found in the engineered polypeptide (i.e., the different residue than in the reference polypeptide). In some instances (e.g., in the Tables in the Examples), the present disclosure also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. In some instances, a polypeptide of the present disclosure can include one or more amino acid residue differences relative to a reference sequence, which is indicated by a list of the specified positions where residue differences are present relative to the reference sequence. In some embodiments, where more than one amino acid can be used in a specific residue position of a polypeptide, the various amino acid residues that can be used are separated by a "l" (e.g., X307G/X307Q or X307G/Q). The present disclosure includes engineered polypeptide sequences comprising one or more amino acid differences that include either/or both conservative and non-conservative amino acid substitutions.

The terms "amino acid substitution set" and "substitution set" refers to a group of amino acid substitutions within a polypeptide sequence. In some embodiments, substitution sets comprise 1, 2, 3, 4, 5, 6, 7, 8, 9, 10, 11, 12, 13, 14, 15, or more amino acid substitutions. In some embodiments, a substitution set refers to the set of amino acid substitutions that is present in any of the variant AvPAL polypeptides listed in any of the Tables in the Examples.

"Conservative amino acid substitution" refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain may be substituted with another aliphatic amino acid (e.g., alanine, valine, leucine, and isoleucine); an amino acid with hydroxyl side chain is substituted with another amino acid with a hydroxyl side chain (e.g., serine and threonine); an amino acid having aromatic side chains is substituted with another amino acid having an aromatic side chain (e.g., phenylalanine, tyrosine, tryptophan, and histidine); an amino acid with a basic side chain is substituted with another amino acid with a basic side chain (e.g., lysine and arginine); an amino acid with an acidic side chain is substituted with another amino acid with an acidic side chain (e.g., aspartic acid or glutamic acid); and a hydrophobic or hydrophilic amino acid is replaced with another hydrophobic or hydrophilic amino acid, respectively. Exemplary conservative substitutions are provided in Table 1.

TABLE 1

Exemplary Conservative Amino Acid Substitutions

| Residue | Potential Conservative Substitutions |
|---|---|
| A, L, V, I | Other aliphatic (A, L, V, I) |
|  | Other non-polar (A, L, V, I, G, M) |
| G, M | Other non-polar (A, L, V, I, G, M) |
| D, E | Other acidic (D, E) |
| K, R | Other basic (K, R) |
| N, Q, S, T | Other polar |
| H, Y, W, F | Other aromatic (H, Y, W, F) |
| C, P | Non-polar |

"Non-conservative substitution" refers to substitution of an amino acid in the polypeptide with an amino acid with significantly differing side chain properties. Non-conservative substitutions may use amino acids between, rather than within, the defined groups and affect: (a) the structure of the peptide backbone in the area of the substitution (e.g., proline for glycine); (b) the charge or hydrophobicity; and/or (c) the bulk of the side chain. By way of example and not limitation, exemplary non-conservative substitutions include an acidic amino acid substituted with a basic or aliphatic amino acid; an aromatic amino acid substituted with a small amino acid; and a hydrophilic amino acid substituted with a hydrophobic amino acid.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered transaminase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

The terms "functional fragment" and "biologically active fragment" are used interchangeably herein, to refer to a polypeptide that has an amino-terminal and/or carboxy-terminal deletion(s) and/or internal deletions, but where the remaining amino acid sequence is identical to the corresponding positions in the sequence to which it is being compared (e.g., a full length engineered PAL of the present invention) and that retains substantially all of the activity of the full-length polypeptide.

"Isolated polypeptide" refers to a polypeptide which is substantially separated from other contaminants that naturally accompany it (e.g., protein, lipids, and polynucleotides). The term embraces polypeptides which have been removed or purified from their naturally-occurring environment or expression system (e.g., host cell or in vitro synthesis). The recombinant PAL polypeptides may be present within a cell, present in the cellular medium, or prepared in various forms, such as lysates or isolated preparations. As such, in some embodiments, the recombinant PAL polypeptides provided herein are isolated polypeptides.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure PAL composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated recombinant PAL polypeptides are substantially pure polypeptide compositions.

"Improved enzyme property" refers to an engineered PAL polypeptide that exhibits an improvement in any enzyme property as compared to a reference PAL polypeptide, such as a wild-type PAL polypeptide (e.g., AvPAL wild-type having SEQ ID NO:4) or another engineered PAL polypeptide. Improved properties include but are not limited to such properties as increased protein expression, increased thermoactivity, increased thermostability, increased pH activity, increased stability, increased enzymatic activity, increased substrate specificity and/or affinity, increased specific activity, increased resistance to substrate and/or end-product inhibition, increased chemical stability, improved chemoselectivity, improved solvent stability, increased tolerance to acidic pH, increased tolerance to proteolytic activity (i.e., reduced sensitivity to proteolysis), reduced aggregation, increased solubility, reduced immunogenicity, and altered temperature profile.

The phrase "contains fewer phenylalanine residues" means that an engineered PAL polypeptide according to the invention will retain at least the activity, or stability when compared to a reference PAL in a standard assay (e.g., as described in the Examples) after one or more phenylalanine residues have been removed from its polypeptide sequence via mutation to any other amino acid.

"Increased enzymatic activity" and "enhanced catalytic activity" refer to an improved property of the engineered PAL polypeptides, which can be represented by an increase in specific activity (e.g., product produced/time/weight protein) and/or an increase in percent conversion of the substrate to the product (e.g., percent conversion of starting amount of substrate to product in a specified time period using a specified amount of PAL) as compared to the reference PAL enzyme (e.g., wild-type AvPAL and/or another engineered AvPAL). Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.1 fold the enzymatic activity of the corresponding wild-type enzyme, to as much as 2-fold, 5-fold, 10-fold, 20-fold, 25-fold, 50-fold, 75-fold, 100-fold, 150-fold, 200-fold or more enzymatic activity than the naturally occurring PAL or another engineered PAL from which the PAL polypeptides were derived.

In some embodiments, the engineered PAL polypeptides have a $k_{cat}$ of at least 0.1/sec, at least 0.2/sec, at least 0.3/sec, at least 0.5/sec, at least 1.0/sec, and in some preferred embodiments greater than 2.0/sec. In some embodiments, the $K_m$ is in the range of about 1 μm to about 5 mM; in the range of about 5 μm to about 2 mM; in the range of about 10 μm to about 2 mM; or in the range of about 10 μm to about 1 mM. In some specific embodiments, the engineered PAL enzyme exhibits improved enzymatic activity in the range of 1.5 to 10 fold, 1.5 to 25 fold, 1.5 to 50 fold, 1.5 to 100 fold or greater, than that of the reference PAL enzyme. PAL activity can be measured by any standard assay known in the art (e.g., by monitoring changes in spectrophotometric properties of reactants or products). In some embodiments, the amount of products produced is measured by High-Performance Liquid Chromatography (HPLC) separation combined with UV absorbance or fluorescent detection directly or following o-phthaldialdehyde (OPA) derivatization. In some embodiments, comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells, in order to minimize variations in amount of enzyme produced by the host cells and present in the lysates.

"Physiological pH" as used herein means the pH range generally found in a subject's (e.g., human) small intestine. There normally is a gradient pH from the pyloric valve to the large intestine, in the range of about 6.0 to 7.5.

The terms "proteolytic activity" and "proteolysis" used interchangeably herein refer to the breakdown of proteins into smaller polypeptides or amino acids. The breakdown of proteins is generally the result of hydrolysis of the peptide bond by protease (proteinase) enzymes. Protease enzymes include but are not limited to pepsin, trypsin, chymotrypsin, elastase; carboxypeptidase A and B, and peptidases (e.g., amino peptidase, dipeptidase and enteropeptidase).

The phrases "reduced sensitivity to proteolysis," "reduced proteolytic sensitivity" and "increased tolerance to proteolysis," are used interchangeably herein mean that an engineered PAL polypeptide according to the invention has a higher enzyme activity compared to a reference PAL in a standard assay (e.g., as described in the Examples) after treatment with one or more proteases.

The phrase "increased storage stability at elevated temperature" means that an engineered PAL polypeptide according to the invention will retain more activity compared to a reference PAL in a standard assay (e.g., as described in the Examples) after it has been produced in a dried form, e.g. by lyophilization or spray-drying, and stored for a period of time ranging from a few days to multiple months at a temperature above room temperature (e.g., 30° C., 37° C., 45° C., 55° C., etc.).

"Aggregation" means clumping or precipitation of a PAL polypeptide. Aggregation can lead to inactivation of the enzyme. The term "reduced aggregation" means an engineered PAL polypeptide will be less prone to aggregation, as compared to a reference PAL. Methods for assessing aggregation are known in the art, including but not limited to the use of fluorescent microscopy with appropriate dyes (e.g., thioflavin T or Nile Red), dynamic light scattering, flow cytometry with appropriate dyes (e.g., Bodipy), filtration and analysis by SDS-PAGE, and/or Western blotting, fluorescent correlation spectroscopy, and electron microscopy. There are commercially available kits to assess aggregation (e.g., the ProteoStat Protein Aggregation Assay kit [Enzo]).

"Conversion" refers to the enzymatic conversion (or biotransformation) of substrate(s) to the corresponding product(s). "Percent conversion" refers to the percent of the substrate that is converted to the product within a period of time under specified conditions. Thus, the "enzymatic activity" or "activity" of a PAL polypeptide can be expressed as "percent conversion" of the substrate to the product in a specific period of time.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA, with greater than about 90% identity to target-polynucleotide. Exemplary moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5×Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Codon optimized" refers to changes in the codons of the polynucleotide encoding a protein to those preferentially used in a particular organism such that the encoded protein is more efficiently expressed in that organism. Although the genetic code is degenerate, in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the PAL enzymes are codon optimized for optimal production from the host organism selected for expression. "Control sequence" refers herein to include all components that are necessary or advantageous for the expression of a polynucleotide and/or polypeptide of the present disclosure. Each control sequence may be native or foreign to the nucleic acid sequence encoding the polypeptide. Such control sequences include, but are not limited to, leaders, polyadenylation sequences, propeptide sequences, promoter sequences, signal peptide sequences, initiation sequences, and transcription terminators. At a minimum, the control sequences include a promoter, and transcriptional and translational stop signals. In some embodiments, the control sequences are provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed (i.e., in a functional relationship) at a position relative to a polynucleotide of interest such that the control sequence directs or regulates the expression of the polynucleotide encoding a polypeptide of interest.

"Promoter sequence" refers to a nucleic acid sequence that is recognized by a host cell for expression of a polynucleotide of interest, such as a coding sequence. The promoter sequence contains transcriptional control sequences that mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Substrate" in the context of an enzymatic conversion reaction process refers to the compound or molecule acted on by the PAL polypeptide. "Product" in the context of an enzymatic conversion process refers to the compound or molecule resulting from the action of the PAL polypeptide on the substrate.

As used herein the term "culturing" refers to the growing of a population of microbial cells under suitable conditions using any suitable medium (e.g., liquid, gel, or solid).

Recombinant polypeptides (e.g., PAL enzyme variants) can be produced using any suitable methods known the art. For example, there is a wide variety of different mutagenesis techniques well known to those skilled in the art. In addition, mutagenesis kits are also available from many commercial molecular biology suppliers. Methods are available to make specific substitutions at defined amino acids (site-directed), specific or random mutations in a localized region of the gene (regio-specific), or random mutagenesis over the entire gene (e.g., saturation mutagenesis). Numerous suitable methods are known to those in the art to generate enzyme variants, including but not limited to site-directed mutagenesis of single-stranded DNA or double-stranded DNA using PCR, cassette mutagenesis, gene synthesis, error-prone PCR, shuffling, and chemical saturation mutagenesis, or any other suitable method known in the art. Non-limiting examples of methods used for DNA and protein engineering are provided in the following patents: U.S. Pat. Nos. 6,117,679; 6,420,175; 6,376,246; 6,586,182; 7,747,391; 7,747,393; 7,783,428; and 8,383,346. After the variants are produced, they can be screened for any desired property (e.g., high or increased activity, or low or reduced activity, increased thermal activity, increased thermal stability, and/or acidic pH stability, etc.). In some embodiments, "recombinant PAL polypeptides" (also referred to herein as "engineered PAL polypeptides," "variant PAL enzymes," and "PAL variants") find use.

As used herein, a "vector" is a DNA construct for introducing a DNA sequence into a cell. In some embodiments, the vector is an expression vector that is operably linked to a suitable control sequence capable of effecting the expression in a suitable host of the polypeptide encoded in the DNA sequence. In some embodiments, an "expression vector" has a promoter sequence operably linked to the DNA sequence (e.g., transgene) to drive expression in a host cell, and in some embodiments, also comprises a transcription terminator sequence.

As used herein, the term "expression" includes any step involved in the production of the polypeptide including, but not limited to, transcription, post-transcriptional modification, translation, and post-translational modification. In some embodiments, the term also encompasses secretion of the polypeptide from a cell.

As used herein, an amino acid or nucleotide sequence (e.g., a promoter sequence, signal peptide, terminator sequence, etc.) is "heterologous" to another sequence with which it is operably linked if the two sequences are not associated in nature.

As used herein, the terms "host cell" and "host strain" refer to suitable hosts for expression vectors comprising DNA provided herein (e.g., a polynucleotide sequences encoding at least one AvPAL variant). In some embodiments, the host cells are prokaryotic or eukaryotic cells that have been transformed or transfected with vectors constructed using recombinant DNA techniques as known in the art.

The term "analogue" means a polypeptide having more than 70% sequence identity but less than 100% sequence identity (e.g., more than 75%, 78%, 80%, 83%, 85%, 88%, 90%, 91%, 92%, 93%, 94%, 95%, 96%, 97%, 98%, 99% sequence identity) with a reference polypeptide. In some embodiments, analogues include non-naturally occurring amino acid residues including, but not limited to, homoarginine, ornithine and norvaline, as well as naturally occurring amino acids. In some embodiments, analogues also include one or more D-amino acid residues and non-peptide linkages between two or more amino acid residues.

The term "therapeutic" refers to a compound administered to a subject who shows signs or symptoms of pathology having beneficial or desirable medical effects.

The term "pharmaceutical composition" refers to a composition suitable for pharmaceutical use in a mammalian subject (e.g., human) comprising a pharmaceutically effective amount of an engineered PAL polypeptide encompassed by the invention and an acceptable carrier.

The term "gene therapy" is used in reference to the use of genes (i.e., genetic material) to treat and/or prevent disease in a mammalian subject (e.g., human) In some embodiments, the genetic material is introduced directly into at least some cells of the mammalian subject. It is not intended that the present invention be limited to any specific method(s) or composition(s) useful for gene therapy.

The term "mRNA therapy" is used in reference to the use of messenger RNA (mRNA) to treat and/or prevent disease in a mammalian subject (e.g., human) In some embodiments, the genetic material is introduced directly into at least some cells of the mammalian subject. It is not intended that the present invention be limited to any specific method(s) or composition(s) useful for mRNA therapy.

The term "effective amount" means an amount sufficient to produce the desired result. One of general skill in the art may determine what the effective amount by using routine experimentation.

The terms "isolated" and "purified" are used to refer to a molecule (e.g., an isolated nucleic acid, polypeptide, etc.) or other component that is removed from at least one other component with which it is naturally associated. The term "purified" does not require absolute purity, rather it is intended as a relative definition.

The term "subject" encompasses mammals such as humans, non-human primates, livestock, companion animals, and laboratory animals (e.g., rodents and lagamorphs). It is intended that the term encompass females as well as males.

As used herein, the term "patient" means any subject that is being assessed for, treated for, or is experiencing disease.

The term "infant" refers to a child in the period of the first month after birth to approximately one (1) year of age. As used herein, the term "newborn" refers to child in the period from birth to the 28$^{th}$ day of life. The term "premature infant" refers to an infant born after the twentieth completed week of gestation, yet before full term, generally weighing ~500 to ~2499 grams at birth. A "very low birth weight infant" is an infant weighing less than 1500 g at birth.

As used herein, the term "child" refers to a person who has not attained the legal age for consent to treatment or research procedures. In some embodiments, the term refers to a person between the time of birth and adolescence.

As used herein, the term "adult" refers to a person who has attained legal age for the relevant jurisdiction (e.g., 18 years of age in the United States). In some embodiments, the term refers to any fully grown, mature organism. In some embodiments, the term "young adult" refers to a person less than 18 years of age, but who has reached sexual maturity.

As used herein, "composition" and "formulation" encompass products comprising at least one engineered PAL of the present invention, intended for any suitable use (e.g., pharmaceutical compositions, dietary/nutritional supplements, feed, etc.).

The terms "administration" and "administering" a composition mean providing a composition of the present invention to a subject (e.g., to a person suffering from the effects of PKU).

The term "carrier" when used in reference to a pharmaceutical composition means any of the standard pharmaceutical carrier, buffers, and excipients, such as stabilizers, preservatives, and adjuvants.

The term "pharmaceutically acceptable" means a material that can be administered to a subject without causing any undesirable biological effects or interacting in a deleterious manner with any of the components in which it is contained and that possesses the desired biological activity.

As used herein, the term "excipient" refers to any pharmaceutically acceptable additive, carrier, diluent, adjuvant, or other ingredient, other than the active pharmaceutical ingredient (API; e.g., the engineered PAL polypeptides of the present invention). Excipients are typically included for formulation and/or administration purposes.

The term "therapeutically effective amount" when used in reference to symptoms of disease/condition refers to the amount and/or concentration of a compound (e.g., engineered PAL polypeptides) that ameliorates, attenuates, or eliminates one or more symptom of a disease/condition or prevents or delays the onset of symptom(s) (e.g., PKU). In some embodiments, the term is use in reference to the amount of a composition that elicits the biological (e.g., medical) response by a tissue, system, or animal subject that is sought by the researcher, physician, veterinarian, or other clinician.

The term "therapeutically effective amount" when used in reference to a disease/condition refers to the amount and/or concentration of a composition that ameliorates, attenuates, or eliminates the disease/condition.

It is intended that the terms "treating," "treat" and "treatment" encompass preventative (e.g., prophylactic), as well as palliative treatment.

Engineered PAL Polypeptides:

The parent PAL polypeptides from which the engineered PAL polypeptides of the invention are derived from include bacterial strains such as *Anabaena* (e.g., *A. variabilis*), *Nostoc* (e.g., *N. punctiforme*), *Rhodosporidium* (e.g., *R. toruloides*), *Streptomyces* (e.g., *S. maritimus* or *S. verticillatus*), *Oscillatoria* sp., *Gloeocapsa* sp., and *Rivularia* sp. PAL enzymes from these strains have been identified and are well known. Homologous enzyme sequences from *Anabaena* (*A. variabilis*) ATCC 29413 and NCBI YP_324488.1; *Nostoc* (*N. punctiforme*) ATCC 29133 and NCBI YP_00186563.1; *Oscillatoria* sp. PCC 6506 and NCBI ZP_07108482.1 and *Gloeocapsa* sp. PCC7428 and NCBI YP_007127054.1 are provided in FIG. 1 of US Pat. Appln. Ser. No. 2014/0314843, incorporated herein by reference.

Furthermore, when a particular PAL variant (i.e., an engineered PAL polypeptide) is referred to by reference to modification of particular amino acids residues in the sequence of a wild-type PAL or reference PAL it is to be understood that variants of another PAL modified in the equivalent position(s) (as determined from the optional amino acid sequence alignment between the respective amino acid sequences) are encompassed herein. In some embodiments, the engineered PAL polypeptide is derived from any one of the polypeptides listed from the bacterial strains above (i.e., *Nostoc*[*N. punctiforme*], *Rhodosporidium* [*R. toruloides*], *Streptomyces* [*S. maritimus* or *S. verticillatus*], *Oscillatoria* sp., *Gloeocapsa* sp and *Rivularia* sp.). In some additional embodiments, the engineered PAL polypeptide of the present invention comprises the conserved active site Ala167-Ser168-Gly169 and comprises at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO:4. In some embodiments, the engineered PAL polypeptides comprise not only PAL activity but are also active on tyrosine and/or histidine substrates.

In some embodiments, engineered PAL polypeptides are produced by cultivating a microorganism comprising at least one polynucleotide sequence encoding at least one engineered PAL polypeptide under conditions which are conducive for producing the engineered PAL polypeptide. In some embodiments, the engineered PAL polypeptide is subsequently recovered from the resulting culture medium and/or cells.

The present invention provides exemplary engineered PAL polypeptides having PAL activity. The Examples provide Tables showing sequence structural information correlating specific amino acid sequence features with the functional activity of the engineered PAL polypeptides. This structure-function correlation information is provided in the form of specific amino acid residue differences relative to the reference engineered polypeptide of SEQ ID NO:2, as well as associated experimentally determined activity data for the exemplary engineered PAL polypeptides.

In some embodiments, the engineered PAL polypeptides of the present invention having PAL activity comprise a) an amino acid sequence having at least 85% sequence identity to reference sequence SEQ ID NO:2; b) an amino acid residue difference as compared to SEQ ID NO:2 at one or more amino acid positions; and c) which exhibits an improved property selected from i) enhanced catalytic activity, ii) reduced proteolytic sensitivity, iii) reduced aggregation, iv) increased stability as a lyophilized preparation to elevated temperatures, v) a reduced number of phenylalanine residues in its primary structure, or a combination of any of i), ii), iii), iv), or v) as compared to the reference sequence.

In some embodiments the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:2, and an amino acid residue difference as compared to SEQ ID NO:2, at one or more amino acid positions (such as at 1, 2, 3, 4, 5, 6, 7, 8, 9, 10, 11, 12, 14, 15, 20 or more amino acid positions compared to SEQ ID NO:2 or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:2). In some embodiments, the residue difference as compared to SEQ ID NO:2, at one or more positions includes at least 1, 2, 3, 4, 5, 6, 7, 8, 9, 10 or more conservative amino acid substitutions. In some embodiments, the engineered PAL polypeptide is a polypeptide listed in the Tables provided in the Examples.

In some embodiments, the engineered PAL polypeptides of the present invention having PAL activity comprise a) an amino acid sequence having at least 85% sequence identity to reference sequence SEQ ID NO:4; b) an amino acid residue difference as compared to SEQ ID NO:4 at one or more amino acid positions; and c) which exhibits an improved property selected from i) enhanced catalytic activity, ii) reduced proteolytic sensitivity, iii) reduced aggregation, iv) increased stability as a lyophilized preparation to elevated temperatures, v) a reduced number of phenylalanine residues in its primary structure, or a combination of any of i), ii), iii), iv), or v) as compared to the reference sequence.

In some embodiments the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:4, and an amino acid residue difference as compared to SEQ ID NO:4, at one or more amino acid positions (such as at 1, 2, 3, 4, 5, 6, 7, 8, 9, 10, 11, 12, 14, 15, 20 or more amino acid positions compared to SEQ ID NO:4 or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:4). In some embodiments, the residue difference as compared to SEQ ID NO:4, at one or more positions includes at least 1, 2, 3, 4, 5, 6, 7, 8, 9, 10 or more conservative amino acid substitutions. In some embodiments, the engineered PAL polypeptide is a polypeptide listed in the Tables provided in the Examples.

In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:6. In some embodiments the amino acid difference is 1, 2, 3, 4, 5, 6, 7, 8, 9, 10, 15, or 20 or greater amino acid positions. In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:6 and at least one amino acid residue difference as compared to SEQ ID NO:6, at one or more amino acid positions selected from 16, 16/150, 44/239/495, 44/56, 44/56/102/239/285/469/470/495, 44/239, 44/239/285/470, 44/239/285/469/495, 44/239/285/470, 44/239/469/470, 44/239/470/546, 44/239/495/546, 44/469/470, 102, 102/470, 162, 162, 165, 188, 239/285/469, 239/285, 239/469/470/495, 264, 267, 267, 285/470, 285/469/470/495, 285/470/495, 364, 455, 469/470, 472, and 482, or any combination thereof, wherein the amino acid positions are numbered relative SEQ ID NO:6. In some embodiments, the amino acid substitutions are selected from F16A/E/K/N/R/S/T/V/W, F16K/F150A, N44C/T239A/T495A, N44H/I56V, N44H/I56V/T102Q/T239A/I285L/V469I/D470E/T495A, N44H/T239A, N44H/T239A/I285L/D470E, N44H/T239A/I285R/V469I/T495A, N44H/T239A/I285R/D470E, N44H/T239A/V469I/D470E, N44H/T239A/D470E/S546A, N44H/T239A/T495A/S546A, N44H/V469I/D470E, T102Q, T102Q/D470E, F162Q/W, I165L, F188I, T239A/I285L/V469I, T239A/I285R, T239A/V469I/D470E/T495A, F264H, F267G/V, I285L/D470E, I285L/V469I/D470E/T495A, I285R/D470E/T495A, L364E/H/S/T, N455S, V469I/D470E, F472A, and F482C/N, wherein the amino acid positions are numbered relative to SEQ ID NO:6.

In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:6. In some embodiments the amino acid difference is 1, 2, 3, 4, 5, 6, 7, 8, 9, 10, 15, or 20 or greater amino acid positions. In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:6 and at least one amino acid residue difference as compared to SEQ ID NO:6, at one or more amino acid positions selected from 16, 264, 364, and 472, wherein the amino acid positions are numbered relative to SEQ ID NO:8. In some embodiments, the amino acid substitutions are selected from F16S, F264H, L364H, F472A, and F482N, wherein the amino acid positions are numbered relative to SEQ ID NO:6.

In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:6. In some embodiments the amino acid difference is 1, 2, 3, 4, 5, 6, 7, 8, 9, 10, 15, or 20 or greater amino acid positions. In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:6, and at least one amino acid residue difference as compared to SEQ ID NO:8, at one or more amino acid positions selected from 16, 16/150, 162, 188, 264, 267, 398, 434, 472A/L/V, and F482C/N/S, wherein the amino acid positions are numbered relative to SEQ ID NO:6. In some embodiments, the amino acid substitutions are selected from F16A/E/K/L/M/N/P/R/S/T/V/W, F16K/F150A, F162M/Q/W, F188A/I/N, F264H, F267G/L/Q/S/V, F398H, F434V, F472A/L/V, and F482C/N/S, wherein the amino acid positions are numbered relative to SEQ ID NO:6.

In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:8. In some embodiments the amino acid difference is 1, 2, 3, 4, 5, 6, 7, 8, 9, 10, 15, or 20 or greater amino acid positions. In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:8, and at least one amino acid residue difference as compared to SEQ ID NO:8, at one or more amino acid position selected from 44/102/285/364, 44/285/364, 44/47/204/209/285, 44/47/364/470/495, 44/54/285/470, 44/54/56/204/239/285/364/495, 44/54/56/204/239/470/495, 44/204/285/364/470/495, 44/204/209/285, 44/209/285/460/495, 47/54/209, 47/204/209/239/285/495, 47/204/285/364/495, 47/209/239/364, 47/239/285/364, 47/470, 54, 54/285/470, 54/56/204/209/470, 54/56/204/209/495, 54/56/285/364/470, 54/56, 54/56/285/470, 54/56/204/495, 54/56/209/562, 54/165/204/209/239/285/470/495, 54/239/495, 54/470, 56, 165, 204, 204/209/239/285/470/495, 204/209/364, 204/209/364/495, 204/239, 204/239/285, 204/364, 204/470, wherein the amino acid positions are numbered relative to SEQ ID NO:8. In some embodiments, the amino acid substitutions are selected from N44C/T102Q/I285R/L364H, N44C/I285R/L364E, N44H/A47K/R204K/S209P/I285R, N44H/A47K/L364H/D470E/T495A, N44H/K54P/I285R/D470E, N44H/K54P/I56V/R204K/T239A/I285R/L364S/T495A, N44H/K54P/I56V/R204K/T239A/D470E/T495A, N44H/R204K/I285R/L364H/D470E/T495A, N44H/R204K/S209P/I285R, N44H/S209P/I285R/T460G/T495A, A47K/K54P/S209P, A47K/R204K/S209P/T239A/I285R/T495A, A47K/R204K/I285R/L364H/T495A, A47K/S209P/T239A/L364H, A47K/T239A/I285R/L364H, A47K/T239A/I285R/L364H, A47K/D470E, K54E, K54P/I285L/D470E, K54E/I285R/D470E, K54E/I56V/R204K/S209P/D470E, K54E/I56V/R204K/S209P/T495A, K54E/I56V/I285R/L364S/D470E, K54P/I56V, K54P/I56V/I285L/D470E, K54P/I56V/R204K/T495A, K54P/I56V/S209P/I562N, K54P/I165L/R204K/S209P/T239A/I285R/D470E/T495A, K54P/T239A/T495A, K54P/D470E, I56V, I165L, R204K, R204K/S209P/T239A/I285R/D470E/T495A, R204K/S209P/L364E/T495A, R204K/S209P/L364H, R204K/S209P/L364H/T495A, R204K/T239A, R204K/T239A/I285R, R204K/L364H, R204K/D470E, S209P/I285L/L364H/D470E, S209P/I285R/L364E/D470E, S209P/I285R/L364E/D470E/T495A, S209P/I285R/L364H/D470E/T495A, S209P/L364H, S209P/L364H/T495A, S209P/D470E, T239A/L364H, I285R/L364H, I285R/L364H/T495A, L364H, L364H/D470E, D470E, and T495A, wherein the amino acid positions are numbered relative to SEQ ID NO:8.

In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:12. In some embodiments the amino acid difference is 1, 2, 3, 4, 5, 6, 7, 8, 9, 10, 15, or 20 or greater amino acid positions. In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:12 and at least one amino acid residue difference as compared to SEQ ID NO:12, at one or more amino acid position selected from 54/56/162/204/285, 54/56/398/472, 54/162/204/398, 54/162/398, 54/204/398, 54/56/162/204/398, 54/56/204/285, 54/56/204/398, 54/56/204/398/472, 54/56/285, 54/56/398, 54/162/398, 54/204/285/398/472, 54/285/398, 54/285/398/472, 56/162/398, 56/204/285, 56/204/398, 56/204/398/460, 56/204/398/472, 56/285, 56/285/398/472, 56/398, 56/398/472, and 201/204/398, wherein the amino acid positions are numbered relative to SEQ ID NO:12. In some embodiments, the amino acid substitutions are selected from K54E/I56V/F162W/R204K/L285I, K54E/I56V/F398H/F472L, K54E/F162W/R204K/F398H, K54E/F162W/F398H, K54E/R204K/F398H, K54P/I56V/F162W/R204K/F398H, K54P/I56V/R204K/L285I, K54P/I56V/R204K/F398H, K54P/I56V/R204K/F398H/F472L, K54P/I56V/L285I, K54P/I56V/F398H, K54P/F162W/F398H, K54P/R204K/L285I/F398H/F472L, K54P/L285I/F398H, K54P/L285I/F398H/F472L, I56V/F162W/F398H, I56V/R204K/L285I, I56V/R204K/F398H, I56V/R204K/F398H/T460G, I56V/R204K/F398H/F472L, I56V/L285I, I56V/L285I, I56V/L285I/F398H/F472L, I56V/F398H, I56V/F398H, I56V/F398H/F472L, and T201A/R204K/F398H, wherein the amino acid positions are numbered relative to SEQ ID NO:12.

In some embodiments, the engineered PAL polypeptides exhibiting at least one improved property have at least 85%, at least 86%, at least 87%, at least 88%, at least 90%, at least 91%, at least 92%, at least 93%, at least 94%, at least 95%, at least 96%, at least 97%, at least 98%, or 99% sequence identity to SEQ ID NO:2, 4, 8, 10, and/or 12. In some embodiments, the engineered PAL polypeptide exhibiting at least one improved property is selected from SEQ ID NOS:4, 6, 8, 10, and 12.

In some embodiments, the present invention provides functional fragments of engineered PAL polypeptides. In some embodiments, functional fragments comprise at least about 90%, at least about 95%, at least about 96%, at least about 97%, at least about 98%, or at least about 99% of the activity of the engineered PAL polypeptide from which it was derived (i.e., the parent engineered PAL). In some embodiments, functional fragments comprise at least about 90%, at least about 91%, at least about 92%, at least about 93%, at least about 94%, at least about 95%, at least about 96%, at least about 97%, at least about 98%, or at least about 99% of the parent sequence of the engineered PAL. In some embodiments the functional fragment is truncated by less than 5, less than 10, less than 15, less than 10, less than 25, less than 30, less than 35, less than 40, less than 45, and less than 50 amino acids.

In some embodiments, the present invention provides functional fragments of engineered PAL polypeptides. In some embodiments, functional fragments comprise at least about 95%, 96%, 97%, 98%, or 99% of the activity of the engineered PAL polypeptide from which it was derived (i.e., the parent engineered PAL). In some embodiments, functional fragments comprise at least 90%, 91%, 92%, 93%, 94%, 95%, 96%, 97%, 98%, or 99% of the parent sequence of the engineered PAL. In some embodiments the functional fragment is truncated by less than 5, less than 10, less than 15, less than 10, less than 25, less than 30, less than 35, less than 40, less than 45, less than 50, less than 55, less than 60, less than 65, or less than 70 amino acids.

In some embodiments, the engineered PAL polypeptide exhibiting at least one improved property has at least 85%, at least 88%, at least 90%, at least 91%, at least 92%, at least 93%, at least 94%, at least 95%, at least 96%, at least 97%, at least 98%, at least 99%, or greater amino acid sequence identity with SEQ ID NO:6, 8, 10, 12, and/or 14, and an amino acid residue difference as compared to SEQ ID NO:4, 6, 8, 10, and/or 12, at one or more amino acid positions (such as at 1, 2, 3, 4, 5, 6, 7, 8, 9, 10, 11, 12, 14, 15 or more amino acid positions) compared to SEQ ID NO:4, 6, 8, 10, and/or 12, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:4, 6, 8, 10, and/or 12. In some embodiments, the engineered PALs comprise at least 90% sequence identity to SEQ ID NO:6 and comprise an amino acid difference as compared to SEQ ID NO:4, 6, 8, 10, and/or 12, of at least 1, 2, 3, 4, 5, 6, 7, 8, 9, 10 or more amino acid positions. In some embodiments, the engineered PAL polypeptide consists of the sequence of SEQ ID NO:4, 6, 8, 10, and/or 12.

In some embodiments, the engineered PAL polypeptide exhibiting at least one improved property has at least 85%, at least 88%, at least 90%, at least 91%, at least 92%, at least 93%, at least 94%, at least 95%, at least 96%, at least 97%, at least 98%, at least 99%, or greater amino acid sequence identity with SEQ ID NO:4, or a functional fragment thereof, and an amino acid residue difference as compared to SEQ ID NO:4, at one or more amino acid positions (such as at 1, 2, 3, 4, 5, 6, 7, 8, 9, 10, 11, 12, 14, 15 or more amino acid positions) compared to SEQ ID NO:4, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:4. In some embodiments, the engineered PALs comprise at least 90% sequence identity to SEQ ID NO:4 and comprise an amino acid difference as compared to SEQ ID NO:4, of at least 1, 2, 3, 4, 5, 6, 7, 8, 9, 10 or more amino acid positions. In some embodiments, the engineered PAL polypeptide consists of the sequence of SEQ ID NO:4.

In some embodiments, the engineered PAL polypeptide exhibiting at least one improved property has at least 85%, at least 88%, at least 90%, at least 91%, at least 92%, at least 93%, at least 94%, at least 95%, at least 96%, at least 97%, at least 98%, at least 99%, or greater amino acid sequence identity with SEQ ID NO:6, or a functional fragment thereof, and an amino acid residue difference as compared to SEQ ID NO:6, at one or more amino acid positions (such as at 1, 2, 3, 4, 5, 6, 7, 8, 9, 10, 11, 12, 14, 15 or more amino acid positions) compared to SEQ ID NO:6, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:6. In some embodiments, the engineered PALs comprise at least 90% sequence identity to SEQ ID NO:6 and comprise an amino acid difference as compared to SEQ ID NO:6, of at least 1, 2, 3, 4, 5, 6, 7, 8, 9, 10 or more amino acid positions. In some embodiments, the engineered PAL polypeptide consists of the sequence of SEQ ID NO:6.

In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99%, or greater amino acid sequence identity with SEQ ID NO:8, or a functional fragment thereof and an amino acid residue difference as compared to SEQ ID NO:8, at one or more amino acid positions (such as at 1, 2, 3, 4, 5, 6, 7, 8, 9, 10, 11, 12, 14, 15 or more amino acid positions) compared to SEQ ID NO:8, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:8. In some embodiments, the engineered PALs comprise at least 90% sequence identity to SEQ ID NO:8, and comprise an amino acid difference as compared to SEQ ID NO:8, of at least 1, 2, 3, 4, 5, 6, 7, 8, 9, 10 or more amino acid positions. In some embodiments, the engineered PAL polypeptide consists of the sequence of SEQ ID NO:8.

In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99%, or greater amino acid sequence identity with SEQ ID NO:10, or a functional fragment thereof and an amino acid residue difference as compared to SEQ ID NO:10, at one or more amino acid positions (such as at 1, 2, 3, 4, 5, 6, 7, 8, 9, 10, 11, 12, 14, 15 or more amino acid positions) compared to SEQ ID NO:10, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:10. In some embodiments, the engineered PALs comprise at least 90% sequence identity to SEQ ID NO:10, and comprise an amino acid difference as compared to SEQ ID NO:10, of at least 1, 2, 3, 4, 5, 6, 7, 8, 9, 10 or more amino acid positions. In some embodiments, the engineered PAL polypeptide consists of the sequence of SEQ ID NO:10.

In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:12 or a functional fragment thereof and an amino acid residue difference as compared to SEQ ID NO:12 at one or more amino acid positions (such as at 1, 2, 3, 4, 5, 6, 7, 8, 9, 10, 11, 12, 14, 15 or more amino acid positions) compared to SEQ ID NO:12, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:12. In some embodiments, the engineered PALs comprise at least 90% sequence identity to SEQ ID NO:12, and comprise an amino acid difference as compared to SEQ ID NO:12, of at least 1, 2, 3, 4, 5, 6, 7, 8, 9, 10 or more amino acid positions. In some embodiments, the engineered PAL polypeptide consists of the sequence of SEQ ID NO:12.

Variants with Reduced Sensitivity to Proteolysis:

In some embodiments, the engineered PAL polypeptides of the present invention have PAL activity, exhibit reduced sensitivity to proteolysis, and comprise: a) an amino acid sequence having at least 85% sequence identity to reference sequence SEQ ID NO:4, 6, 8, 10, and/or 12; an b) an amino acid residue difference as compared to SEQ ID NO:4, 6, 8, 10, and/or 12, at one or more amino acid positions.

In some embodiments, the engineered PAL polypeptides that exhibit reduced sensitivity to proteolysis have at least 85%, at least 88%, at least 90%, at least 91%, at least 92%, at least 93%, at least 94%, at least 95%, at least 96%, at least 97%, at least 98%, at least 99%, or greater amino acid sequence identity with SEQ ID NO:4, 6, 8, 10, and/or 12, and an amino acid residue difference as compared to SEQ ID NO:4, 6, 8, 10, and/or 12, at one or more amino acid positions (such as at 1, 2, 3, 4, 5, 6, 7, 8, 9, 10, 11, 12, 14, 15, 20 or more amino acid positions compared to SEQ ID NO:4, 6, 8, 10, and/or 12, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:4, 6, 8, 10, and/or 12).

In some embodiments, the proteolytic sensitivity of the engineered PAL polypeptides is reduced by at least 5%, at least 10%, at least 15%, at least 20%, at least 25%, at least 30%, at least 40%, at least 50%, at least 60%, at least 70%, at least 80%, at least 85%, at least 90%, or at least 95%, of that of the wild-type PAL (e.g., AvPAL having SEQ ID NO:2) or as compared to a reference PAL polypeptide under essentially the same conditions. The proteolytic activity can be measured using any suitable methods known in the art, including but not limited to those described in the Examples.

In some embodiments, the engineered PAL polypeptides having reduced sensitivity to proteolysis have reduced sensitivity to a composition comprising one or more proteases, including, but not limited to pepsin, trypsin, chymotrypsin, carboxypeptidase A and B, peptidases (e.g., amino peptidase, dipeptidase and enteropeptidase) when both the reference PAL and the engineered PAL having reduced sensitivity are compared and exposed to essentially the same amount and kind of protease under essentially the same conditions.

In some embodiments, the engineered PAL polypeptide having reduced sensitivity to proteolysis have enzyme activity levels that are about 1.0 fold, 2-fold, 5-fold, 10-fold, 20-fold, 25-fold, 50-fold, 75-fold, 100-fold, 150-fold, 200-fold or more of the enzymatic activity of the reference PAL (e.g., AvPAL). In some embodiments, the engineered polypeptides have more enzyme activity, as compared to a reference PAL, when activity is measured at a pH range of 4.5 to 7.5; when activity is measured at a pH range of 4.5 to 6.5; when activity is measured at a pH range of 5.0 to 7.5; when activity is measured at a pH range of 5.0 to 6.5; when activity is measured at a pH range of 5.5 to 7.5; and/or also when activity is measured at a pH range of 5.5 to 6.5. In some other embodiments, the engineered PAL polypeptides have $K_m$ values in the range of 1 μM to 5 mM.

Variants with Increased Tolerance to Storage at Elevated Temperatures:

In some embodiments, the engineered PAL polypeptides of the invention have PAL activity, are more tolerant to storage at elevated temperatures and comprise: a) an amino acid sequence having at least 85% sequence identity to reference sequence SEQ ID NO:4, 6, 8, 10, and/or 12, or a fragment thereof; and b) an amino acid residue difference as compared to SEQ ID NO:4, 6, 8, 10, and/or 12, at one or more amino acid positions.

In some embodiments, the engineered PAL polypeptides that exhibit increased tolerance to storage at elevated temperatures as compared to wild-type AvPAL and/or another reference polypeptide have at least 85%, at least 88%, at least 90%, at least 91%, at least 92%, at least 93%, at least 94%, at least 95%, at least 96%, at least 97%, at least 98%, at least 99%, or greater amino acid sequence identity with SEQ ID NO:4, 6, 8, 10, and/or 12, and an amino acid residue difference as compared to SEQ ID NO:4, at one or more amino acid positions (such as at 1, 2, 3, 4, 5, 6, 7, 8, 9, 10, 11, 12, 14, 15, 20 or more amino acid positions compared to SEQ ID NO:4, 6, 8, 10, and/or 12, or a sequence having at least 85%, at least 88%, at least 90%, at least 91%, at least 92%, at least 93%, at least 94%, at least 95%, at least 96%, at least 97%, at least 98%, at least 99%, or greater amino acid sequence identity with SEQ ID NO:4, 6, 8, 10, and/or 12.

In some embodiments, when all other assay conditions are essentially the same, the engineered PAL polypeptides having increased tolerance to storage at elevated temperatures as compared to a reference PAL polypeptide have an increased tolerance at a temperature of about 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., etc.

In some embodiments, the engineered PAL polypeptides that have increased tolerance to storage at elevated temperatures also exhibit greater PAL activity as compared to a reference PAL when measure by a standard assay. Any suitable assay finds use in the present invention, including, but not limited to those provided herein.

Variants that Contain Fewer Phenylalanine Residues:

In some embodiments, the engineered PAL polypeptides of the present invention have PAL activity, and a reduced number of phenylalanine residues in its primary sequence, and comprise: a) an amino acid sequence having at least 85% sequence identity to reference sequence SEQ ID NO:4, 6, 8, 10, and/or 12; and/or b) an amino acid residue difference as compared to SEQ ID NO:4, 6, 8, 10, and/or 12, at one or more amino acid positions.

In some embodiments, the engineered PAL polypeptides that contain a reduced number of phenylalanine residues in its primary sequence have at least 85%, at least 88%, at least 90%, at least 91%, at least 92%, at least 93%, at least 94%, at least 95%, at least 96%, at least 97%, at least 98%, at least 99%, or greater amino acid sequence identity with SEQ ID NO:4, 6, 8, 10, and/or 12, and an amino acid residue difference as compared to SEQ ID NO:4, 6, 8, 10, and/or 12, at one or more amino acid positions (such as at 1, 2, 3, 4, 5, 6, 7, 8, 9, 10, 11, 12, 14, 15, 20 or more amino acid positions compared to SEQ ID NO:4, 6, 8, 10, and/or 12, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:4, 6, 8, 10, and/or 12).

In some embodiments, the engineered PAL polypeptides that contain a reduced number of phenylalanine residues in its primary sequence have at least 85%, at least 88%, at least 90%, at least 91%, at least 92%, at least 93%, at least 94%, at least 95%, at least 96%, at least 97%, at least 98%, at least 99%, or greater amino acid sequence identity with SEQ ID NO:6 and an amino acid residue difference as compared to SEQ ID NO:6, at one or more amino acid positions are selected from 16, 16/150, 162, 188, 264, 267, 398, 434, 472A/L/V, and F482C/N/S, or any combination thereof, when optimally aligned with the amino acid sequence of SEQ ID NO:6. In some embodiments the amino acid difference is 1, 2, 3, 4, 5, 6, 7, 8, 9, 10, 15, 20, or 25, or greater amino acid positions.

In some embodiments, the engineered PAL polypeptides that contain a reduced number of phenylalanine residues in its primary sequence have at least 85%, at least 88%, 90%, 91%, 92%, 93%, 94%, 95%, 96%, 97%, 98%, or 99% sequence identity to SEQ ID NO:6, and comprise an amino acid residue difference at position F16, F150, F162, F188, F264, F267, F398, F434, F472, F482 and optionally an amino acid residue difference at 1, 2, 3, 4, 5, 6, 7, 8, 9, 10 or more amino acid positions. In some embodiments, the amino acid residue difference is selected from F16A/E/K/L/M/N/P/R/S/TN/W, F16K/F150A, F162M/Q/W, F188A/I/N, F264H, F267G/L/Q/S/V, F398H, F434V, F472A/L/V, and F482C/N/S, wherein the amino acid residues are numbered with reference to SEQ ID NO:6.

In some embodiments, the engineered PAL polypeptides containing fewer phenylalanine residues than wild-type PAL also have proteolytic sensitivity that is reduced by at least 5%, at least 10%, at least 15%, at least 20%, at least 25%, at least 30%, at least 40%, at least 50%, at least 60%, at least 70%, at least 80%, at least 85%, at least 90%, or at least 95%, of that of the wild-type PAL (e.g., AvPAL having SEQ ID NO:2) or as compared to a reference PAL polypeptide under essentially the same conditions. The activity can be measured using any suitable methods known in the art, including but not limited to those described in the Examples.

In some embodiments, the engineered PAL polypeptides containing fewer phenylalanine residues than wild-type PAL in their primary sequences, have reduced sensitivity to compositions comprising one or more proteases, including, but not limited to pepsin, trypsin, chymotrypsin, carboxypeptidase A and B, peptidases (e.g., amino peptidase, dipeptidase and enteropeptidase) when both the reference PAL and the engineered PAL having the reduced phenylalanine content are compared and exposed to essentially the same amount and kind of protease under essentially the same conditions.

In some embodiments, the engineered PAL polypeptides containing a reduced number of phenylalanine residues in their primary sequences have enzyme activity levels that are about 1.0 fold, 2-fold, 5-fold, 10-fold, 20-fold, 25-fold, 50-fold, 75-fold, 100-fold, 150-fold, 200-fold or more of the enzymatic activity of the reference PAL (e.g., AvPAL). In some embodiments, the engineered polypeptides have more enzyme activity, as compared to a reference PAL, when activity is measured at a pH range of 4.5 to 7.5; when activity is measured at a pH range of 4.5 to 6.5; when activity is measured at a pH range of 5.0 to 7.5; when activity is measured at a pH range of 5.0 to 6.5; when activity is measured at a pH range of 5.5 to 7.5; and/or also when activity is measured at a pH range of 5.5 to 6.5. In some other embodiments, the engineered PAL polypeptides have $K_m$ values in the range of 1 µM to 5 mM.

It is further contemplated that any of the exemplary engineered polypeptides (i.e., all of the variants provided in the tables and described herein) find use as the starting amino acid sequence for synthesizing other engineered PAL polypeptides, for example by subsequent rounds of evolution by adding new combinations of various amino acid differences from other polypeptides and other residue positions described herein. In some embodiments, additional improvements are generated by including amino acid differences at residue positions that were maintained as unchanged throughout earlier rounds of evolution. It is not intended that the present invention be limited to any particular method for producing engineered PAL polypeptides, as any suitable method finds use, including but not limited to the methods provided herein.

Polynucleotides Encoding Engineered Polypeptides, Expression Vectors and Host Cells:

The present invention provides polynucleotides encoding the engineered PAL polypeptides described herein. In some embodiments, the polynucleotides are operatively linked to one or more heterologous regulatory sequences that control gene expression to create a recombinant polynucleotide capable of expressing the polypeptide. In some embodiments, expression constructs containing at least one heterologous polynucleotide encoding the engineered PAL polypeptide(s) is introduced into appropriate host cells to express the corresponding PAL polypeptide(s).

As will be apparent to the skilled artisan, availability of a protein sequence and the knowledge of the codons corresponding to the various amino acids provide a description of all the polynucleotides capable of encoding the subject polypeptides. The degeneracy of the genetic code, where the same amino acids are encoded by alternative or synonymous codons, allows an extremely large number of nucleic acids to be made, all of which encode an engineered PAL polypeptide. Thus, the present invention provides methods and compositions for the production of each and every possible variation of PAL polynucleotides that could be made that encode the PAL polypeptides described herein by selecting combinations based on the possible codon choices, and all such variations are to be considered specifically disclosed for any polypeptide described herein, including the amino acid sequences presented in the Examples (e.g., in the various Tables).

In some embodiments, the codons are preferably optimized for utilization by the chosen host cell for protein production. For example, preferred codons used in bacteria are typically used for expression in bacteria. Consequently, codon optimized polynucleotides encoding the engineered PAL polypeptides contain preferred codons at about 40%, 50%, 60%, 70%, 80%, 90%, or greater than 90% of the codon positions in the full length coding region.

In some embodiments, the PAL polynucleotide encodes an engineered polypeptide having PAL activity with the properties disclosed herein, wherein the polypeptide comprises an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NOS:3, 5, 7, 9, and/or 11, or the amino acid sequence of any variant (e.g., those provided in the Examples), and one or more residue differences as compared to the reference polynucleotide of SEQ ID NOS:3, 5, 7, 9, and/or 11, or the amino acid sequence of any variant as disclosed in the Examples (for example 1, 2, 3, 4, 5, 6, 7, 8, 9, 10 or more amino acid residue positions). In some embodiments, the reference sequence is selected from SEQ ID NOS:3, 5, 7, 9, and/or 11.

In some embodiments, the PAL polynucleotide encodes an engineered polypeptide having PAL activity with the properties disclosed herein, wherein the polypeptide comprises an amino acid sequence having at least 80%, 85%, 86%, 87%, 88%, 89%, 90%, 91%, 92%, 93%, 94%, 95%, 96%, 97%, 98%, 99%, or more sequence identity to reference sequence SEQ ID NO:4, 6, 8, 10, and/or 12 and one or more residue differences as compared to SEQ ID NO:4, 6, 8, 10, and/or 12.

In some embodiments, the polynucleotide encoding the engineered PAL polypeptides comprises a polynucleotide sequence selected from a polynucleotide sequence selected from SEQ ID NOS:3, 5, 7, 9, and/or 11. In some embodiments, the polynucleotide encoding an engineered PAL polypeptide has at least 80%, 85%, 90%, 93%, 95%, 96%, 97%, 98%, 99% nucleotide residue identity to SEQ ID NOS:3, 5, 7, 9, and/or 11.

In some embodiments, the polynucleotides are capable of hybridizing under highly stringent conditions to a reference polynucleotide sequence selected from SEQ ID NOS:3, 5, 7, 9, and/or 11, or a complement thereof, or a polynucleotide sequence encoding any of the variant PAL polypeptides provided herein. In some embodiments, the polynucleotide capable of hybridizing under highly stringent conditions encodes a PAL polypeptide comprising an amino acid sequence that has one or more residue differences as compared to SEQ ID NO:4, 6, 8, 10, and/or 12.

In some embodiments, an isolated polynucleotide encoding any of the engineered PAL polypeptides herein is manipulated in a variety of ways to facilitate expression of the PAL polypeptide. In some embodiments, the polynucleotides encoding the PAL polypeptides comprise expression vectors where one or more control sequences is present to regulate the expression of the PAL polynucleotides and/or polypeptides. Manipulation of the isolated polynucleotide prior to its insertion into a vector may be desirable or necessary depending on the expression vector utilized. Techniques for modifying polynucleotides and nucleic acid sequences utilizing recombinant DNA methods are well known in the art. In some embodiments, the control sequences include among others, promoters, leader sequences, polyadenylation sequences, propeptide sequences, signal peptide sequences, and transcription terminators. In some embodiments, suitable promoters are selected based on the host cells selection. For bacterial host cells, suitable promoters for directing transcription of the nucleic acid constructs of the present disclosure, include, but are not limited to promoters obtained from the E. coli lac operon, Streptomyces coelicolor agarase gene (dagA), Bacillus subtilis levansucrase gene (sacB), Bacillus licheniformis alpha-amylase gene (amyL), Bacillus stearothermophilus maltogenic amylase gene (amyM), Bacillus amyloliquefaciens alpha-amylase gene (amyQ), Bacillus licheniformis penicillinase gene (penP), Bacillus subtilis xylA and xylB genes, and prokaryotic beta-lactamase gene (See e.g., Villa-Kamaroff et al., Proc. Natl Acad. Sci. USA 75:3727-3731 [1978]), as well as the tac promoter (See e.g., DeBoer et al., Proc. Natl Acad. Sci. USA 80: 21-25 [1983]). Exemplary promoters for filamentous fungal host cells, include, but are not limited to promoters obtained from the genes for Aspergillus oryzae TAKA amylase, Rhizomucor miehei aspartic proteinase, Aspergillus niger neutral alpha-amylase, Aspergillus niger acid stable alpha-amylase, Aspergillus niger or Aspergillus awamori glucoamylase (glaA), Rhizomucor miehei lipase, Aspergillus oryzae alkaline protease, Aspergillus oryzae triose phosphate isomerase, Aspergillus nidulans acetamidase, and Fusarium oxysporum trypsin-like protease (See e.g., WO 96/00787), as well as the NA2-tpi promoter (a hybrid of the promoters from the genes for Aspergillus niger neutral alpha-amylase and Aspergillus oryzae triose phosphate isomerase), and mutant, truncated, and hybrid promoters thereof. Exemplary yeast cell promoters can be from the genes can be from the genes for Saccharomyces cerevisiae enolase (ENO-1), Saccharomyces cerevisiae galactokinase (GAL1), Saccharomyces cerevisiae alcohol dehydrogenase/glyceraldehyde-3-phosphate dehydrogenase (ADH2/GAP), and Saccharomyces cerevisiae 3-phosphoglycerate kinase. Other useful promoters for yeast host cells are known in the art (See e.g., Romanos et al., Yeast 8:423-488 [1992]).

In some embodiments, the control sequence is also a suitable transcription terminator sequence (i.e., a sequence recognized by a host cell to terminate transcription). In some embodiments, the terminator sequence is operably linked to the 3' terminus of the nucleic acid sequence encoding the PAL polypeptide. Any suitable terminator which is functional in the host cell of choice finds use in the present invention. Exemplary transcription terminators for filamentous fungal host cells can be obtained from the genes for Aspergillus oryzae TAKA amylase, Aspergillus niger glucoamylase, Aspergillus nidulans anthranilate synthase, Aspergillus niger alpha-glucosidase, and Fusarium oxysporum trypsin-like protease. Exemplary terminators for yeast host cells can be obtained from the genes for Saccharomyces cerevisiae enolase, Saccharomyces cerevisiae cytochrome C (CYC1), and Saccharomyces cerevisiae glyceraldehyde-3-phosphate dehydrogenase. Other useful terminators for yeast host cells are known in the art (See e.g., Romanos et al., supra).

In some embodiments, the control sequence is also a suitable leader sequence (i.e., a non-translated region of an mRNA that is important for translation by the host cell). in some embodiments, the leader sequence is operably linked to the 5' terminus of the nucleic acid sequence encoding the PAL polypeptide. Any suitable leader sequence that is functional in the host cell of choice find use in the present invention. Exemplary leaders for filamentous fungal host cells are obtained from the genes for Aspergillus oryzae TAKA amylase, and Aspergillus nidulans triose phosphate isomerase. Suitable leaders for yeast host cells are obtained from the genes for Saccharomyces cerevisiae enolase (ENO-1), Saccharomyces cerevisiae 3-phosphoglycerate kinase, Saccharomyces cerevisiae alpha-factor, and Saccharomyces cerevisiae alcohol dehydrogenase/glyceraldehyde-3-phosphate dehydrogenase (ADH2/GAP).

In some embodiments, the control sequence is also a polyadenylation sequence (i.e., a sequence operably linked to the 3' terminus of the nucleic acid sequence and which, when transcribed, is recognized by the host cell as a signal to add polyadenosine residues to transcribed mRNA). Any suitable polyadenylation sequence which is functional in the host cell of choice finds use in the present invention. Exemplary polyadenylation sequences for filamentous fungal host cells include, but are not limited to the genes for Aspergillus oryzae TAKA amylase, Aspergillus niger glucoamylase, Aspergillus nidulans anthranilate synthase, Fusarium oxysporum trypsin-like protease, and Aspergillus niger alpha-glucosidase. Useful polyadenylation sequences for yeast host cells are known (See e.g., Guo and Sherman, Mol. Cell. Bio., 15:5983-5990 [1995]).

In some embodiments, the control sequence is also a signal peptide (i.e., a coding region that codes for an amino acid sequence linked to the amino terminus of a polypeptide and directs the encoded polypeptide into the cell's secretory pathway). In some embodiments, the 5' end of the coding sequence of the nucleic acid sequence inherently contains a signal peptide coding region naturally linked in translation reading frame with the segment of the coding region that encodes the secreted polypeptide. Alternatively, in some embodiments, the 5' end of the coding sequence contains a signal peptide coding region that is foreign to the coding sequence. Any suitable signal peptide coding region which directs the expressed polypeptide into the secretory pathway of a host cell of choice finds use for expression of the engineered polypeptide(s). Effective signal peptide coding regions for bacterial host cells are the signal peptide coding regions include, but are not limited to those obtained from the genes for *Bacillus* NClB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are known in the art (See e.g., Simonen and Palva, Microbiol. Rev., 57:109-137 [1993]). In some embodiments, effective signal peptide coding regions for filamentous fungal host cells include, but are not limited to the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. Useful signal peptides for yeast host cells include, but are not limited to those from the genes for *Saccharomyces cerevisiae* alpha-factor and *Saccharomyces cerevisiae* invertase.

In some embodiments, the control sequence is also a propeptide coding region that codes for an amino acid sequence positioned at the amino terminus of a polypeptide. The resultant polypeptide is referred to as a "proenzyme," "propolypeptide," or "zymogen." A propolypeptide can be converted to a mature active polypeptide by catalytic or autocatalytic cleavage of the propeptide from the propolypeptide. The propeptide coding region may be obtained from any suitable source, including, but not limited to the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (See e.g., WO 95/33836). Where both signal peptide and propeptide regions are present at the amino terminus of a polypeptide, the propeptide region is positioned next to the amino terminus of a polypeptide and the signal peptide region is positioned next to the amino terminus of the propeptide region.

In some embodiments, regulatory sequences are also utilized. These sequences facilitate the regulation of the expression of the polypeptide relative to the growth of the host cell. Examples of regulatory systems are those that cause the expression of the gene to be turned on or off in response to a chemical or physical stimulus, including the presence of a regulatory compound. In prokaryotic host cells, suitable regulatory sequences include, but are not limited to the lac, tac, and trp operator systems. In yeast host cells, suitable regulatory systems include, but are not limited to the ADH2 system or GAL1 system. In filamentous fungi, suitable regulatory sequences include, but are not limited to the TAKA alpha-amylase promoter, *Aspergillus niger* glucoamylase promoter, and *Aspergillus oryzae* glucoamylase promoter.

In another aspect, the present invention is directed to a recombinant expression vector comprising a polynucleotide encoding an engineered PAL polypeptide, and one or more expression regulating regions such as a promoter and a terminator, a replication origin, etc., depending on the type of hosts into which they are to be introduced. In some embodiments, the various nucleic acid and control sequences described herein are joined together to produce recombinant expression vectors which include one or more convenient restriction sites to allow for insertion or substitution of the nucleic acid sequence encoding the PAL polypeptide at such sites. Alternatively, in some embodiments, the nucleic acid sequence of the present invention is expressed by inserting the nucleic acid sequence or a nucleic acid construct comprising the sequence into an appropriate vector for expression. In some embodiments involving the creation of the expression vector, the coding sequence is located in the vector so that the coding sequence is operably linked with the appropriate control sequences for expression.

The recombinant expression vector may be any suitable vector (e.g., a plasmid or virus), that can be conveniently subjected to recombinant DNA procedures and bring about the expression of the PAL polynucleotide sequence. The choice of the vector typically depends on the compatibility of the vector with the host cell into which the vector is to be introduced. The vectors may be linear or closed circular plasmids.

In some embodiments, the expression vector is an autonomously replicating vector (i.e., a vector that exists as an extra-chromosomal entity, the replication of which is independent of chromosomal replication, such as a plasmid, an extra-chromosomal element, a minichromosome, or an artificial chromosome). The vector may contain any means for assuring self-replication. In some alternative embodiments, the vector is one in which, when introduced into the host cell, it is integrated into the genome and replicated together with the chromosome(s) into which it has been integrated. Furthermore, in some embodiments, a single vector or plasmid, or two or more vectors or plasmids which together contain the total DNA to be introduced into the genome of the host cell, and/or a transposon is utilized.

In some embodiments, the expression vector contains one or more selectable markers, which permit easy selection of transformed cells. A "selectable marker" is a gene, the product of which provides for biocide or viral resistance, resistance to heavy metals, prototrophy to auxotrophs, and the like. Examples of bacterial selectable markers include, but are not limited to the dal genes from *Bacillus subtilis* or *Bacillus licheniformis*, or markers, which confer antibiotic resistance such as ampicillin, kanamycin, chloramphenicol or tetracycline resistance. Suitable markers for yeast cells include, but are not limited to ADE2, HIS3, LEU2, LYS2, MET3, TRP1, and URA3. Selectable markers for use in filamentous fungal host cells include, but are not limited to, amdS (acetamidase; e.g., from *A. nidulans* or *A. oryzae*), argB (ornithine carbamoyltransferases), bar (phosphinothricin acetyltransferase; e.g., from *S. hygroscopicus*), hph (hygromycin phosphotransferase), niaD (nitrate reductase), pyrG (orotidine-5'-phosphate decarboxylase; e.g., from *A. nidulans* or *A. oryzae*), sC (sulfate adenyltransferase), and trpC (anthranilate synthase), as well as equivalents thereof. In another aspect, the present invention provides a host cell comprising at least one polynucleotide encoding at least one engineered PAL polypeptide of the present invention, the polynucleotide(s) being operatively linked to one or more control sequences for expression of the engineered PAL enzyme(s) in the host cell. Host cells suitable for use in expressing the polypeptides encoded by the expression vectors of the present invention are well known in the art and include but are not limited to, bacterial cells, such as *E. coli*, *Vibrio fluvialis*, *Streptomyces* and *Salmonella typhimurium* cells; fungal cells, such as yeast cells (e.g., *Saccharomyces cerevisiae* or *Pichia pastoris* (ATCC Accession No.

201178)); insect cells such as *Drosophila* S2 and *Spodoptera* Sf9 cells; animal cells such as CHO, COS, BHK, 293, and Bowes melanoma cells; and plant cells. Exemplary host cells also include various *Escherichia coli* strains (e.g., W3110 (ΔfhuA) and BL21).

Accordingly, in another aspect, the present invention provides methods of producing the engineered PAL polypeptides, where the methods comprise culturing a host cell capable of expressing a polynucleotide encoding the engineered PAL polypeptide under conditions suitable for expression of the polypeptide. In some embodiments, the methods further comprise the steps of isolating and/or purifying the PAL polypeptides, as described herein.

Appropriate culture media and growth conditions for host cells are well known in the art. It is contemplated that any suitable method for introducing polynucleotides for expression of the PAL polypeptides into cells will find use in the present invention. Suitable techniques include, but are not limited to electroporation, biolistic particle bombardment, liposome mediated transfection, calcium chloride transfection, and protoplast fusion.

Engineered PAL polypeptides with the properties disclosed herein can be obtained by subjecting the polynucleotide encoding the naturally occurring or engineered PAL polypeptide to any suitable mutagenesis and/or directed evolution methods known in the art, and/or as described herein. An exemplary directed evolution technique is mutagenesis and/or DNA shuffling (See e.g., Stemmer, Proc. Natl. Acad. Sci. USA 91:10747-10751 [1994]; WO 95/22625; WO 97/0078; WO 97/35966; WO 98/27230; WO 00/42651; WO 01/75767 and U.S. Pat. No. 6,537,746). Other directed evolution procedures that can be used include, among others, staggered extension process (StEP), in vitro recombination (See e.g., Zhao et al., Nat. Biotechnol., 16:258-261 [1998]), mutagenic PCR (See e.g., Caldwell et al., PCR Methods Appl., 3:S136-S140 [1994]), and cassette mutagenesis (See e.g., Black et al., Proc. Natl. Acad. Sci. USA 93:3525-3529 [1996]).

Mutagenesis and directed evolution methods can be readily applied to PAL-encoding polynucleotides to generate variant libraries that can be expressed, screened, and assayed. Any suitable mutagenesis and directed evolution methods find use in the present invention and are well known in the art (See e.g., U.S. Pat. Nos. 5,605,793, 5,811,238, 5,830,721, 5,834,252, 5,837,458, 5,928,905, 6,096,548, 6,117,679, 6,132,970, 6,165,793, 6,180,406, 6,251,674, 6,265,201, 6,277,638, 6,287,861, 6,287,862, 6,291,242, 6,297,053, 6,303,344, 6,309,883, 6,319,713, 6,319,714, 6,323,030, 6,326,204, 6,335,160, 6,335,198, 6,344,356, 6,352,859, 6,355,484, 6,358,740, 6,358,742, 6,365,377, 6,365,408, 6,368,861, 6,372,497, 6,337,186, 6,376,246, 6,379,964, 6,387,702, 6,391,552, 6,391,640, 6,395,547, 6,406,855, 6,406,910, 6,413,745, 6,413,774, 6,420,175, 6,423,542, 6,426,224, 6,436,675, 6,444,468, 6,455,253, 6,479,652, 6,482,647, 6,483,011, 6,484,105, 6,489,146, 6,500,617, 6,500,639, 6,506,602, 6,506,603, 6,518,065, 6,519,065, 6,521,453, 6,528,311, 6,537,746, 6,573,098, 6,576,467, 6,579,678, 6,586,182, 6,602,986, 6,605,430, 6,613,514, 6,653,072, 6,686,515, 6,703,240, 6,716,631, 6,825,001, 6,902,922, 6,917,882, 6,946,296, 6,961,664, 6,995,017, 7,024,312, 7,058,515, 7,105,297, 7,148,054, 7,220,566, 7,288,375, 7,384,387, 7,421,347, 7,430,477, 7,462,469, 7,534,564, 7,620,500, 7,620,502, 7,629,170, 7,702,464, 7,747,391, 7,747,393, 7,751,986, 7,776,598, 7,783,428, 7,795,030, 7,853,410, 7,868,138, 7,783,428, 7,873,477, 7,873,499, 7,904,249, 7,957,912, 7,981,614, 8,014,961, 8,029,988, 8,048,674, 8,058,001, 8,076,138, 8,108,150, 8,170,806, 8,224,580, 8,377,681, 8,383,346, 8,457,903, 8,504,498, 8,589,085, 8,762,066, 8,768,871, 9,593,326, and all related US and non-US counterparts; Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229:1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 0/75767; WO 2009/152336; and U.S. Pat. Appln. Publ. Nos. 2011/0082055, 2014/0005057, 2014/0214391, 2014/0221216, 2015/0133307, 2015/0134315, and 2015/0050658; all of which are incorporated herein by reference).

In some embodiments, the enzyme clones obtained following mutagenesis treatment are screened by subjecting the enzyme preparations to a defined temperature (or other assay conditions) and measuring the amount of enzyme activity remaining after heat treatments or other suitable assay conditions. Clones containing a polynucleotide encoding a PAL polypeptide are then isolated from the gene, sequenced to identify the nucleotide sequence changes (if any), and used to express the enzyme in a host cell. Measuring enzyme activity from the expression libraries can be performed using any suitable method known in the art (e.g., standard biochemistry techniques, such as HPLC analysis).

For engineered polypeptides of known sequence, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides disclosed herein can be prepared by chemical synthesis using the classical phosphoramidite method (See e.g., Beaucage et al., Tet. Lett., 22:1859-69 [1981]; and Matthes et al., EMBO J., 3:801-05 [1984]), as it is typically practiced in automated synthetic methods. According to the phosphoramidite method, oligonucleotides are synthesized (e.g., in an automatic DNA synthesizer, purified, annealed, ligated and cloned in appropriate vectors).

Accordingly, in some embodiments, a method for preparing the engineered PAL polypeptide can comprise: (a) synthesizing a polynucleotide encoding a polypeptide comprising an amino acid sequence selected from the amino acid sequence of any variant as described herein, and (b) expressing the PAL polypeptide encoded by the polynucleotide. In some embodiments of the method, the amino acid sequence encoded by the polynucleotide can optionally have one or several (e.g., up to 3, 4, 5, or up to 10) amino acid residue deletions, insertions and/or substitutions. In some embodiments, the amino acid sequence has optionally 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 18, 20, 21, 22, 23, 24, or 25 amino acid residue deletions, insertions and/or substitutions. In some embodiments, the substitutions are conservative or non-conservative substitutions.

The expressed engineered PAL polypeptide can be evaluated for any desired improved property or combination of properties (e.g., activity, selectivity, stability, acid tolerance, protease sensitivity, etc.) using any suitable assay known in the art, including but not limited to the assays and conditions described herein.

In some embodiments, any of the engineered PAL polypeptides expressed in a host cell are recovered from the cells and/or the culture medium using any one or more of the well-known techniques for protein purification, including, among others, lysozyme treatment, sonication, filtration, salting-out, ultra-centrifugation, and chromatography.

Chromatographic techniques for isolation of the PAL polypeptides include, among others, reverse phase chromatography, high-performance liquid chromatography, ion-exchange chromatography, hydrophobic-interaction chromatography, size-exclusion chromatography, gel electrophoresis, and affinity chromatography. Conditions for purifying a particular enzyme depends, in part, on factors such as net charge, hydrophobicity, hydrophilicity, molecular weight, molecular shape, etc., and will be apparent to those having skill in the art. In some embodiments, affinity techniques may be used to isolate the improved PAL enzymes. For affinity chromatography purification, any antibody that specifically binds a PAL polypeptide of interest may find use. For the production of antibodies, various host animals, including but not limited to rabbits, mice, rats, etc., are immunized by injection with a PAL polypeptide, or a fragment thereof. In some embodiments, the PAL polypeptide or fragment is attached to a suitable carrier, such as BSA, by means of a side chain functional group or linkers attached to a side chain functional group.

In some embodiments, the engineered PAL polypeptide is produced in a host cell by a method comprising culturing a host cell (e.g., an *E. coli* strain) comprising a polynucleotide sequence encoding an engineered PAL polypeptide as described herein under conditions conducive to the production of the engineered PAL polypeptide and recovering the engineered PAL polypeptide from the cells and/or culture medium. In some embodiments, the host cell produces more than one engineered PAL polypeptide.

In some embodiments, the present invention provides a method of producing an engineered PAL polypeptide comprising culturing a recombinant bacterial cell comprising a polynucleotide sequence encoding an engineered PAL polypeptide having at least 85%, 90%, 95%, 96%, 97%, 98%, or 99% sequence identity to reference sequences SEQ ID NO:4, 6, 8, 10, and/or 12, and one or more amino acid residue differences as compared to SEQ ID NO:4, 6, 8, 10, and/or 12, as provided herein, under suitable culture conditions to allow the production of the engineered PAL polypeptide and optionally recovering the engineered PAL polypeptide from the culture and/or cultured bacterial cells. In some embodiments, the host cell produces more than one engineered PAL polypeptide.

In some embodiments, once the engineered PAL polypeptides are recovered from the recombinant host cells and/or culture medium, they are further purified by any suitable method(s) known in the art. In some additional embodiments, the purified PAL polypeptides are combined with other ingredients and compounds to provide compositions and formulations comprising the engineered PAL polypeptide as appropriate for different applications and uses (e.g., pharmaceutical compositions).

Compositions:

The present invention provides engineered PAL polypeptides suitable for use in numerous compositions. These compositions find use in many fields, including but not limited to pharmaceuticals, dietary/nutritional supplements, food, feed, and fine chemical production. For example, in some embodiments, the present invention provides food and/or feeds comprising at least one engineered PAL variant and/or at least one polynucleotide sequence encoding at least one PAL variant. In some embodiments, the present invention provides beverages comprising at least one engineered PAL variant.

In some embodiments, the engineered PAL variant in food, feed, and/or nutritional/dietary supplement is glycosylated. Furthermore, the engineered PAL variants find use in any suitable edible enzyme delivery matrix. In some embodiments, the engineered PAL variants are present in an edible enzyme delivery matrix designed for rapid dispersal of the PAL variant within the digestive tract of an animal upon ingestion of the variant.

The present invention also provides engineered PAL polypeptides suitable for use in production of fine chemicals and other industrially important compounds (See e.g., US Pat. Appln. Nos. 2013/0340119, 2013/0005012, and 2005/0260724, and WO 2012/122333).

Pharmaceutical and Other Compositions:

The present invention provides engineered PAL polypeptides suitable for use in pharmaceutical and other compositions, such as dietary/nutritional supplements.

Depending on the mode of administration, these compositions comprising a therapeutically effective amount of an engineered PAL according to the invention are in the form of a solid, semi-solid, or liquid. In some embodiments, the compositions include other pharmaceutically acceptable components such as diluents, buffers, excipients, salts, emulsifiers, preservatives, stabilizers, fillers, and other ingredients. Details on techniques for formulation and administration are well known in the art and described in the literature.

In some embodiments, the engineered PAL polypeptides are formulated for use in oral pharmaceutical compositions. Any suitable format for use in delivering the engineered PAL polypeptides find use in the present invention, including but not limited to pills, tablets, gel tabs, capsules, lozenges, dragees, powders, soft gels, sol-gels, gels, emulsions, implants, patches, sprays, ointments, liniments, creams, pastes, jellies, paints, aerosols, chewing gums, demulcents, sticks, suspensions (including but not limited to oil-based suspensions, oil-in water emulsions, etc.), slurries, syrups, controlled release formulations, suppositories, etc. In some embodiments, the engineered PAL polypeptides are provided in a format suitable for injection (i.e., in an injectable formulation). In some embodiments, the engineered PAL polypeptides are provided in biocompatible matrices such as sol-gels, including silica-based (e.g., oxysilane) sol-gels. In some embodiments, the engineered PAL polypeptides are encapsulated. In some alternative embodiments, the engineered PAL polypeptides are encapsulated in nanostructures (e.g., nanotubes, nanotubules, nanocapsules, or microcapsules, microspheres, liposomes, etc.). Indeed, it is not intended that the present invention be limited to any particular delivery formulation and/or means of delivery. It is intended that the engineered PAL polypeptides be administered by any suitable means known in the art, including but not limited to parenteral, oral, topical, transdermal, intranasal, intraocular, intrathecal, via implants, etc.

In some embodiments, the engineered PAL polypeptides are chemically modified by glycosylation, pegylation (i.e., modified with polyethylene glycol [PEG] or activated PEG, etc.) or other compounds (See e.g., Ikeda, Amino Acids 29:283-287 [2005]; U.S. Pat. Nos. 7,531,341, 7,534,595, 7,560,263, and 7,53,653; US Pat. Appln. Publ. Nos. 2013/0039898, 2012/0177722, etc.). Indeed, it is not intended that the present invention be limited to any particular delivery method and/or mechanism.

In some additional embodiments, the engineered PAL polypeptides are provided in formulations comprising matrix-stabilized enzyme crystals. In some embodiments, the formulation comprises a cross-linked crystalline engineered PAL enzyme and a polymer with a reactive moiety that adheres to the enzyme crystals. The present invention also provides engineered PAL polypeptides in polymers.

In some embodiments, compositions comprising the engineered PAL polypeptides of the present invention include one or more commonly used carrier compounds, including but not limited to sugars (e.g., lactose, sucrose, mannitol, and/or sorbitol), starches (e.g., corn, wheat, rice, potato, or other plant starch), cellulose (e.g., methyl cellulose, hydroxypropylmethyl cellulose, sodium carboxy-methylcellulose), gums (e.g., arabic, tragacanth, guar, etc.), and/or proteins (e.g., gelatin, collagen, etc.). Additional components in oral formulations may include coloring and or sweetening agents (e.g., glucose, sucrose, and mannitol) and lubricating agents (e.g., magnesium stearate), as well as enteric coatings (e.g., methacrylate polymers, hydroxyl propyl methyl cellulose phthalate, and/or any other suitable enteric coating known in the art). In some embodiments, disintegrating or solubilizing agents are included (e.g., cross-linked polyvinyl pyrrolidone, agar, alginic acid or salts thereof, such as sodium alginate). In some embodiments, the engineered PAL polypeptide are combined with various additional components, including but not limited to preservatives, suspending agents, thickening agents, wetting agents, alcohols, fatty acids, and/or emulsifiers, particularly in liquid formulations.

In some embodiments, the engineered PAL polypeptide are be combined with various additional components, including but not limited to preservatives, suspending agents, thickening agents, wetting agents, alcohols, fatty acids, and/or emulsifiers, particularly in liquid formulations. In some embodiments, the engineered PAL polypeptides are administered to subjects in combination with other compounds used in the treatment of PKU, including but not limited to KUVAN® tetrahydrobiopterin (BioMarin Pharmaceutical, Inc., Novato, Calif.), antacids (e.g., omeprazole, esomeprazole and other prazoles), as well as any other suitable compounds.

In some embodiments, the present invention provides engineered PAL polypeptides suitable for use in decreasing the concentration of phenylalanine in fluids such as blood, cerebrospinal fluid, etc. The dosage of engineered PAL polypeptide(s) administered to a patient with elevated blood phenylalanine levels depends upon the genotype of the patient, the general condition of the patient, and other factors known to those in the art. In some embodiments, PKU patients with elevated blood phenylalanine levels have greater than 360 uM blood phenylalanine concentrations. However, it is not intended that the present invention be limited to administration to patients with blood phenylalanine concentrations that are greater than 360 uM, as the present invention finds use with patients with lower phenylalanine blood concentrations. In some embodiments, the compositions are intended for single or repeat administration to a patient. In some embodiments, it is contemplated that the concentration of engineered PAL polypeptide(s) in the composition(s) administered to a patient is sufficient to effectively treat, ameliorate and/or prevent the symptoms of the disease (e.g., PKU and/or PKU-related conditions, diseases and/or symptoms). In some embodiments, the engineered PAL polypeptides are administered in combination with other pharmaceutical and/or dietary compositions.

In some embodiments, PAL enzymes find use as a therapeutic protein for the treatment of disorders of tyrosine metabolism, such as tyrosinemia Type I, tyrosinemia Type II, tyrosinemia Type III, and alkaptonuria. These disorders of tyrosine metabolism are autosomal metabolic genetic disorders in which one of the enzymes involved in the degradation of tyrosine is partially functional or non-functional, due to a mutation in the corresponding gene. This lack of functionality results in elevated levels of tyrosine and other tyrosine-metabolites in the bloodstream. Because tyrosine is derived from phenylalanine, it is beneficial for patients with a disorder of tyrosine metabolism to limit phenylalanine and tyrosine intake. PAL enzymes are thus a potential treatment of disorders of tyrosine metabolism.

If patients with a disorder of tyrosine metabolism are not treated early, high levels of tyrosine and some of its breakdown products can cause significant medical problems including liver and kidney failure, liver cancer, intellectual disability, and even death.

In some embodiments, the present invention provides engineered PAL polypeptides suitable for use in decreasing the concentration of phenylalanine in fluids such as blood, cerebrospinal fluid, etc. of tyrosinemia and alkaptonuria patients. The dosage of engineered PAL polypeptide(s) administered to a patient with elevated blood tyrosine levels depends upon the genotype of the patient, the general condition of the patient, and other factors known to those in the art. In some embodiments, the compositions are intended for single or repeat administration to a tyrosinemia or alkaptonuria patient. In some embodiments, it is contemplated that the concentration of engineered PAL polypeptide(s) in the composition(s) administered to a patient is sufficient to effectively treat, ameliorate and/or prevent the symptoms of the disease (e.g., tyrosinemia Type I, Type II, or Type III, or alkaptonuria, diseases and/or symptoms), In some embodiments, the engineered PAL polypeptides are administered to tyrosinemia and alkaptonuria patients in combination with nitisinone or other pharmaceutical and/or dietary compositions.

Industrial Compositions:

It is contemplated that the engineered PAL polypeptides of the present invention will find use in industrial compositions. In some embodiments, the engineered PAL polypeptides are formulated for use in the food and/or feed industries. In some embodiments, the engineered PAL polypeptides are formulated in granulated or pelleted products which are mixed with animal feed components such as additional enzymes (for example, cellulases, laccases, and amylases). In some alternative embodiments, the engineered PAL polypeptides are used in liquid animal feed compositions (e.g., aqueous or oil based slurries). Thus, in some embodiments, the engineered PAL variants of the present invention are sufficiently thermotolerant and thermostable to withstand the treatment used to produce pellets and other processed feed/foods.

The engineered PAL variants of the present invention also find use in the production of phenylalanine and/or phenylalanine derivatives.

The foregoing and other aspects of the invention may be better understood in connection with the following non-limiting examples. The examples are provided for illustrative purposes only and are not intended to limit the scope of the present invention in any way.

EXPERIMENTAL

The following Examples, including experiments and results achieved, are provided for illustrative purposes only and are not to be construed as limiting the present invention.

In the experimental disclosure below, the following abbreviations apply: ppm (parts per million); M (molar); mM (millimolar), uM and μM (micromolar); nM (nanomolar); mol (moles); gm and g (gram); mg (milligrams); ug and μg (micrograms); L and l (liter); ml and mL (milliliter); cm (centimeters); mm (millimeters); um and μm (micrometers); sec. (seconds); min(s) (minute(s)); h(s) and hr(s) (hour(s)); U (units); MW (molecular weight); rpm (rotations per minute); psi and PSI (pounds per square inch); ° C. (degrees Centigrade); RT and rt (room temperature); CDS (coding sequence); DNA (deoxyribonucleic acid); RNA (ribonucleic acid); AUC (area under the curve); E. coli W3110 (commonly used laboratory E. coli strain, available from the Coli Genetic Stock Center [CGSC], New Haven, Conn.); HTP (high throughput); HPLC (high pressure liquid chromatography); CFSE (carboxyfluorescein succinimidyl ester); IPTG (isopropyl β-D-1-thiogalactopyranoside); PES (polyethersulfone); PHE and phe (phenylalanine); BSA (bovine serum albumin); PBMC (peripheral blood mononuclear cells); PKU (phenylketonuria); MHC (major histocompatibility complex); HLA (human leukocyte antigen); HLA-DR (an MHC Class II cell surface receptor encoded by the HLA complex on chromosome #6); FIOPC (fold improvements over positive control); LB (Luria broth); Athens Research (Athens Research Technology, Athens, Ga.); ProSpec (ProSpec Tany Technogene, East Brunswick, N.J.); Sigma-Aldrich (Sigma-Aldrich, St. Louis, Mo.); Ram Scientific (Ram Scientific, Inc., Yonkers, N.Y.); Pall Corp. (Pall, Corp., Pt. Washington, N.Y.); Millipore (Millipore, Corp., Billerica Mass.); Difco (Difco Laboratories, BD Diagnostic Systems, Detroit, Mich.); Molecular Devices (Molecular Devices, LLC, Sunnyvale, Calif.); Kuhner (Adolf Kuhner, AG, Basel, Switzerland); Biospringer (Biospringer North America, Milwaukee, Wis.); Cambridge Isotope Laboratories, (Cambridge Isotope Laboratories, Inc., Tewksbury, Mass.); Applied Biosystems (Applied Biosystems, part of Life Technologies, Corp., Grand Island, N.Y.), Agilent (Agilent Technologies, Inc., Santa Clara, Calif.); Thermo Scientific (part of Thermo Fisher Scientific, Waltham, Mass.); Corning (Corning, Inc., Palo Alto, Calif.); Constant Systems (Constant Systems Ltd., Daventry, United Kingdom); Megazyme (Megazyme International, Wicklow, Ireland); Enzo (Enzo Life Sciences, Inc., Farmingdale, N.Y.); GE Healthcare (GE Healthcare Bio-Sciences, Piscataway, N.J.); Harlan (Harlan Laboratories, Indianapolis, Ind.); AB Sciex (AB Sciex, Framingham, Mass.); PetAg Inc. (PetAg, Hampshire, Ill.); and Bio-Rad (Bio-Rad Laboratories, Hercules, Calif.).

The following polynucleotide and polypeptide sequences find use in the present invention. In some cases (as shown below), the polynucleotide sequence is followed by the encoded polypeptide.

```
Polynucleotide Sequence of WT AvPAL
(SEQ ID NO: 1):
                                                      (SEQ ID NO: 1)
ATGAAAACCCTGAGCCAGGCACAGAGCAAAACCAGCAGCCAGCAGTTTAGCTTTACCGG

CAATAGCAGCGCAAATGTGATTATTGGTAATCAGAAACTGACCATCAATGATGTTGCAC

GTGTTGCCCGTAATGGCACCCTGGTTAGCCTGACCAATAATACCGATATTCTGCAGGGTA

TTCAGGCCAGCTGTGATTATATCAATAATGCAGTTGAAAGCGGTGAACCGATTTATGGTG

TTACCAGCGGTTTTG6TGGTATGGCAAATGTTGCAATTAGCCGTGAACAGGCAAGCGAA

CTGCAGACCAATCTGGTTTGGTTTCTGAAAACCGGTGCAGGTAATAAACTGCCGCTGGCA

GATGTTCGTGCAGCAATGCTGCTGCGTGCAAATAGCCACATGCGTGGTGCAAGCGGTATT

CGTCTGGAACTGATTAAACGCATGGAAATCTTTCTGAATGCCGGTGTTACCCCGTATGTT

TATGAATTTGGTAGCATTGGTGCCAGCGGTGATCTGGTTCCGCTGAGCTATATTACCGGT

AGCCTGATTGGCCTGGACCCGAGCTTTAAAGTTGATTTTAATGGCAAAGAAATGGACGC

ACCGACCGCACTGCGTCAGCTGAATCTGAGTCCGCTGACCCTGCTGCCGAAAGAAGGTCT

GGCAATGATGAATGGCACCAGCGTTATGACCGGTATTGCAGCAAATTGTGTTTATGATAC

CCAGATTCTGACCGCAATTGCAATGGGTGTTCATGCACTGGATATTCAGGCACTGAATGG

TACAAATCAGAGCTTTCATCCGTTTATCCATAACAGCAAACCGCATCCGGGTCAGCTGTG

GGCAGCAGATCAGATGATTAGCCTGCTGGCCAATAGCCAGCTGGTTCGTGATGAACTGG

ATGGTAAACATGATTATCGTGATCATGAACTGATCCAGGATCGTTATAGCCTGCGTTGTC

TGCCGCAGTATCTGGGTCCGATTGTTGATGGTATTAGCCAGATTGCCAAACAAATCGAAA

TTGAGATTAACAGCGTTACCGATAACCCGCTGATTGATGTTGATAATCAGGCAAGCTATC

ATGGTGGTAATTTTCTGGGTCAGTATGTTGGTATGGGTATGGATCATCTGCGCTATTATAT
```

-continued

```
CGGTCTGCTGGCAAAACATCTGGATGTTCAGATTGCACTGCTGGCATCACCGGAATTTAG

CAATGGTCTGCCTCCGAGTCTGCTGGGTAATCGTGAACGTAAAGTTAATATGGGTCTGAA

AGGTCTGCAGATTTGCGGTAATAGCATTATGCCGCTGCTGACCTTTTATGGTAATAGTAT

TGCAGATCGTTTTCCGACCCATGCCGAACAGTTTAACCAGAATATTAACAGCCAGGGTTA

TACCAGCGCAACCCTGGCACGTCGTAGCGTTGATATTTTTCAGAATTATGTTGCCATTGC

CCTGATGTTTGGTGTTCAGGCAGTTGATCTGCGTACCTACAAAAAAACCGGTCATTATGA

TGCACGTGCCTGTCTGTCACCGGCAACCGAACGTCTGTATAGCGCAGTTCGTCATGTTGT

TGGTCAGAAACCGACCTCAGATCGTCCGTATATTTGGAATGATAATGAACAGGGTCTGG

ATGAACATATTGCACGTATTAGTGCAGATATTGCAGCCGGTGGTGTTATTGTTCAGGCCG

TTCAGGACATTCTGCCGTGTCTGCAT
```

Polypeptide Sequence of WT AvPAL (SEQ ID NO: 2):

(SEQ ID NO: 2)

```
MKTLSQAQSKTSSQQFSFTGNSSANVIIGNQKLTINDVARVARNGTLVSLTNNTDILQGIQAS

CDYINNAVESGEPIYGVTSGFGGMANVAISREQASELQTNLVWFLKTGAGNKLPLADVRAA

MLLRANSHMRGASGIRLELIKRMEIFLNAGVTPYVYEFGSIGASGDLVPLSYITGSLIGLDPSF

KVDFNGKEMDAPTALRQLNISPLTLLPKEGLAMMNGTSVMTGIAANCVYDTQILTAIAMGV

HALDIQALNGTNQSFHPFIHNSKPHPGQLWAADQMISLLANSQLVRDELDGKHDYRDHELIQ

DRYSLRCLPQYLGPIVDGISQIAKQIEIEINSVTDNPLIDVDNQASYHGGNFLGQYVGMGMDH

LRYYIGLLAKHLDVQIALLASPEFSNGLPPSLLGNRERKVNMGLKGLQICGNSIMPLLTFYGN

SIADRFPTHAEQFNQNINSQGYTSATLARRSVDIFQNYVAIALMFGVQAVDLRTYKKTGHYD

ARACLSPATERLYSAVRHVVGQKPTSDRPYIWNDNEQGLDEHIARISADIAAGGVIVQAVQDI

LPCLH
```

Polynucleotide Sequence of Variant #1 (SEQ ID NO: 3)

(SEQ ID NO: 3)

```
ATGAAAACCCTGAGTCAGGCACAGAGCAAAACCAGCAGCCAGCAGTTTAGCCATACCGGCA

ATAGCAGCGCAAATGTGATTATTGGTAATCAGAAACTGACCATCAATGATGTTGTACGTGTTG

CCCGTAATGGCACCGCGGTTAGCCTGACCAATAATAAAGATATTCTGCAGCGTATTCAGGCC

AGCTGTGATTATATCAATAATGCAGTTGAAAAAGGTGAACCGATTTATGGTGTTACCAGCGG

TTTTGGTGGTATGGCAAATGTTGTAATTAGCCGTGAACAGGCAAGCGAACTGCAGACCAATC

TGGTTTGGTTTCTGAAAACCGGTGCAGGTAATAAACTGCCGCTGGCAGATGTTCGTGCAGCA

ATGCTGCTGCGTGCAAATAGCCACATGCGTGGTGCAAGCGGTATTCGTCTGGAACTGATTAA

ACGCATGGAAATCTTTCTGAATGCCGGTGTTACCCCGTATGTTTATGAATTTGGTAGCATTGG

TGCCAGCGGTGATCTGGTTCCGCTGAGCTATATTACCGGTAGCCTGATTGGCCTGGACCCGAG

CTTTAAAGTTGATTTTAATGGCAAAGAAATGGACGCACCGACCGCACTGCGTCAGCTGAATC

TGAGTCCGCTGACCCTGCAGCCGAAAGAAGGTCTGGCAATGATGAATGGCACCAGCGTTATG

ACCGGTATTGCAGCAAATTGTGTTTATGATACCCAGATTCTGACCGCAATTGCAATGGGTGTT

CATGCACTGGATATTCAGGCACTGAATGGTACAAATCAGAGCTTTCATCCGTTTATCCATAAC

AGCAAACCGCATCCGGGTCAGCTGTGGGCAGCAGATCAGATGATTAGCCTGCTGGCCGGTAG

CCAGCTGGTTCGTGATGAACTGGATGGTAAACATGATTATATGGATGGTGAACTGATCCAGG

ATCGTTATAGCCTGCGTTGTCTGCCGCAGTATCTGGGTCCGATTGTTGATGGTATTAGCCAGA

TTGCCAAACAAATCGAAATTGAGATTAACAGCGTTACCGATAACCCGCTGATTGATGTTGAT

AATCAGGCAAGCTATCATGGTGGTAATTTTCTGGGTCAGTATGTTGGTATGGGTATGGATCAT

CTGCGCTATTATATCGGTCTGCTGGCAAAACATCTGGATGTTCAGATTGCACTGCTGGCATCA
```

-continued

```
CCGGAATTTAGCAATGGTCTGCCTCCGAGTCTGGTGGGTAATCGTGAACGTAAAGTTAATATG

GGTCTGAAAGGTCTGCAGATTTGCGGTAATAGCATTATGCCGCTGCTGACCTTTTATGGTAAT

AGTATTGCAGATCGTTTTCCGACCCATGCCGAACAGTTTAACCAGAATATTAACAGCCAGGGT

TATACCAGCGCAACCCTGGCACGTCGTAGCGTTGATATTTTTCAGAATTATGTTGCCATTGCC

CTGATGTTTGGTGTTCAGGCAGTTGATCTGCGTACCTACAAAAAAACCGGTCATTATGATGCA

CGTGCCCAGCTGTCACCGGCAACCGAACGTCTGTATAGCGCAGTTCGTCATGTTGTTGGTAAA

AAACCGAGCTCAGATCGTCCGTATATTTGGAATGATAATGAACAGGGTCTGGATGAACATAT

TGCACGTATTAGTGCAGATATTGCAGCCGGTGGTGTTATTGTTCAGGCCGTTCAGGACATTCT

GCCGCCGCTGCAT
```

Polypeptide Sequence of Variant #1 (SEQ ID NO: 4)

(SEQ ID NO: 4)

MKTLSQAQSKTSSQQFSHTGNSSANVIIGNQKLTINDVVRVARNGTAVSLTNNKDILQRI

QASCDYINNAVEKGEPIYGVTSGFGGMANVVISREQASELQTNLVWFLKTGAGNKLPLADV

RAAMLLRANSHMRGASGIRLELIKRMEIFLNAGVTPYVYEFGSIGASGDLVPLSYITGSLIGLD

PSFKVDFNGKEMDAPTALRQLNLSPLTLQPKEGLAMMNGTSVMTGIAANCVYDTQILTAIA

MGVHALDIQALNGTNQSFHPFIHNSKPHPGQLWAADQMISLLAGSQLVRDELDGKHDYMD

GELIQDRYSLRCLPQYLGPIVDGISQIAKQIEIEINSVTDNPLIDVDNQASYHGGNFLGQYVGM

GMDHLRYYIGLLAKHLDVQIALLASPEFSNGLPPSLVGNRERKVNMGLKGLQICGNSIMPLL

TFYGNSIADRFPTHAEQFNQNINSQGYTSATLARRSVDIFQNYVAIALMFGVQAVDLRTYKK

TGHYDARAQLSPATERLYSAVRHVVGKKPSSDRPYIWNDNEQGLDE

HIARISADIAAGGVIVQAVQDILPPLH

Example 1

PAL Gene Acquisition and Construction of Expression Vectors

The *Anabaena variabilis* phenylalanine ammonia lyase (AvPAL) gene sequence was designed with codons for optimized expression in *E. coli* and cloned into the *E. coli* expression vector pET16b to provide pET16b-AvPAL and subcloned as described in Example 1, of U.S. Pat. No. 9,611,468. The plasmid construct was transformed into an *E. coli* strain derived from W3110. Directed evolution techniques generally known by those skilled in the art were used to generate libraries of gene variants from this plasmid construct (See e.g., U.S. Pat. No. 8,383,346, and WO2010/144103) as well as AvPAL derivatives. In some embodiments, expression vectors lacking antimicrobial resistance markers find use.

Example 2

High-Throughput (HTP) Growth and Assays

High-Throughput (HTP) Growth of PAL and PAL Variants

Transformed *E. coli* cells were selected by plating onto LB agar plates containing 1% glucose and 30 µg/ml chloramphenicol. After overnight incubation at 37° C., colonies were placed into the wells of 96-well shallow flat bottom plates (NUNC™, Thermo-Scientific) filled with 180 µl/well LB supplemented with 1% glucose and 30 µg/ml chloramphenicol. The cultures were allowed to grow overnight for 18-20 hours in a shaker (200 rpm, 30° C., and 85% relative humidity; Kuhner).

Overnight growth samples (20 µL) were transferred into Costar 96-well deep plates filled with 380 µL of Terrific Broth supplemented with 30 µg/ml chloramphenicol. The plates were incubated for 135 minutes in a shaker (250 rpm, 30° C., and 85% relative humidity; Kuhner). The cells were then induced with 40 µL of 10 mM IPTG in sterile water and incubated overnight for 20-24 hours in a shaker (250 rpm, 30° C., and 85% relative humidity; Kuhner). The cells were pelleted (4000 rpm×20 min), the supernatants were discarded, and the cells were frozen at −80° C. prior to analysis.

Lysis of HTP Pellets

First, 500 µL of lysis buffer (20 mM sodium phosphate pH 8, 150 mM NaCl, 1 mg/ml lysozyme, and 0.5 mg/ml polymyxin B sulfate) were added to the cell pellets. The mixture was agitated for 1.5-2 h at room temperature, and centrifuged (4000 rpm×5 min) prior to use of the clarified lysates in the various HTP assays described herein. Analysis of these lysates by SDS-PAGE revealed the presence of an overexpressed protein at an apparent MW of ~60 kDa, consistent with the expected MW of PAL.

Analysis of Clarified Lysates

PAL variant activity was determined by measuring the formation of cinnamic acid by the change in absorbance at 290 nm over time. For this assay, 100 µL of either 200 mM Tris/50 mM phenylalanine, pH 7.5, or 200 mM sodium phosphate/50 mM phenylalanine pH 7.0, 80 µL of water, and 20 µL of clarified lysate were added to the wells of a poly-acrylate 96-well microtiter plate (Costar #3635, Corning). The reactions were mixed briefly and the activity was determined by tracking the absorbance at 290 nm over time (every 12-20 s over 5-20 min) using a SpectraMax® Plus 384 or a SpectraMax® 190 (Molecular Devices) absorbance microplate reader.

HTP-Analysis of Clarified Lysates Pretreated with Protease

The activity of PAL variants was determined after incubation with chymotrypsin and trypsin to simulate the environment of the intestinal tract (e.g., the upper intestine). First, 30 µL of protease mix (0.01-100 mg/ml chymotrypsin (C4129 Sigma Aldrich), 0.01-100 mg/ml trypsin (T7409 Sigma Aldrich), 1 mM $CaCl_2$, and 1 mM HCl), 0-30 µL of 20 mM sodium taurocholate in 500 mM sodium phosphate pH 7.0, and 90-120 µL of clarified lysate were added to the wells of a 96-well round bottom microtiter plate (Costar #3798, Corning). The plates were sealed and incubated at 37° C. with shaking (Thermotron® shaker HT Infors AJ185, 400 rpm, 1" throw) for 1 h prior to analysis. For the assay, 100 µL of either 200 mM Tris/50 mM phenylalanine pH 7.5 or 200 mM sodium phosphate/50 mM phenylalanine pH 7.0 and 100 µL of the protease treated lysate were added to the wells of a polyacrylate 96-well microtiter plate (Costar #3635, Corning). The reactions were mixed briefly and the activity was determined by tracking the absorbance at 290 nm over time (every 12-20 s over 5-20 min) using a SpectraMax® Plus 384 or a SpectraMax® 190 (Molecular Devices) absorbance microplate reader. The results are provided in the Tables below.

HTP-Analysis of PAL Variants after Storage at Elevated Temperatures

Lysates of PAL variants grown in high throughput were incubated at 65° C. for 1 hr and insoluble material was pelleted (4000 rpm×10 min). The supernatant was transferred to a new 96-well microtiter plate (NUNC™, ThermoScientific), frozen, and lyophilized to a dry powder. Lyophilized enzymes were incubated at 45° C. in a Thermotron® HT shaker (Infors AJ185) for up to 10 days. Subsequently the lyophilized enzymes were resuspended in 400 µL of dd$H_2O$ and mixed by agitation for 10 min. For the assay, 100 µL of 200 mM sodium phosphate/50 mM phenylalanine pH 7.0, 80 µL of dd$H_2O$ and 20 µL of the enzyme suspension were added to the wells of a poly-acrylate 96-well microtiter plate (Costar #3635, Corning). The reactions were mixed briefly and the activity was determined by following the absorbance at 290 nm over time (every 12-20 s over 5-20 min) using a SpectraMax® Plus 384 or a SpectraMax® 190 (Molecular Devices) absorbance microplate reader.

Example 3

Lyophilized Lysates from Shake Flask (SF) Cultures

Selected HTP cultures grown as described in Example 2 above, were plated onto LB-agar plates with 1% glucose and 30 µg/ml chloramphenicol and grown overnight at 37° C. A single colony from each culture was transferred to 50 ml Luria Bertani medium with 1% glucose and 30 µg/ml chloramphenicol. The cultures were grown for 18 h at 30° C., 250 rpm, and subcultured at a dilution of approximately 1:10 into 250 ml of Terrific Broth with 30 µg/ml of chloramphenicol, to a final OD600 of 0.2. The cultures were incubated for 135 minutes at 30° C., 250 rpm, to an OD600 of 0.6 and induced with 1 mM of IPTG. The induced cultures were incubated for 20 h at 30° C., 250 rpm. Following this incubation period, the cultures were centrifuged 4000 rpm×10 min. The supernatant was discarded, and the pellets were resuspended in 30 ml of 20 mM sodium phosphate pH 8, 150 mM NaCl. The cells were pelleted 2860*g for 10 min), resuspended in 12 ml of 50 mM sodium phosphate pH 7.5, and lysed using a One Shot Cell Disruption system (Constant Systems) at 17,000 psi. Lysate was pelleted (10,000 rpm×30 min) and the supernatant was frozen and lyophilized to generate an enzyme powder.

Purification of PAL From Shake Flask Cultures

Select variants were grown in shake flask cultures to saturation, as described above. Saturated cultures were pelleted by centrifugation (4000 rpm×20 min) and the cell pellets were stored at −80° C. prior to purification. The cell pellets were thawed at room temperature and resuspended in 20 mM sodium Phosphate pH 8, 150 mM NaCl at 5 mL of buffer per g of cells. The sample slurry was lysed using a microfluidizer with a pressure setting of 110 psi. The resulting lysate was clarified by centrifugation at 10,000 rpm for 1 hour, followed by filtration through a 0.2 µm PES filter (Millipore).

After filtration, the resulting lysate was heated at 55-65° C. for 1.5-2 hours in the presence or absence of 10 mM phenylalanine. The lysate was removed from the heat and clarified by centrifugation at 10,000 rpm at 4° C. for 1 hour. The supernatant containing soluble PAL was then filtered through a 0.2 µm PES filter.

Bulk crystallization was done with a particulate free solution. The filtered concentrate and anti-solvent (0.1M HEPES, 0.2M NaCl pH 7.5 25% (w/v) PEG 3350) were heated separately to 40° C. Anti-solvent was added slowly in small increments until a cloud point was sustained. Contact seeding was achieved by adding a small amount of existing crystals to the solution after it reached its cloud point (this step is not essential). The solution was cooled linearly from 40° C. to 4° C. over 6 hours. Periodically the suspension was gently mixed to resuspend solids. The suspension was held for 12 to 24 hours at 4° C. The liquid was decanted retaining the settled crystals. The crystalline solids were washed with water to remove residual PEG. Washed crystals were dried by lyophilization overnight.

Example 4

Characterization of Purified PAL and PAL Variants

In this Example, assays conducted to characterize wild-type and variant PALs are described.

Tolerance to Storage Conditions

Lyophilized enzyme variants were incubated in a Thermotron® HT shaker (Infors AJ185) at 45° C. for 1, 5, 7, or 10 days. The lyophilized enzyme was resuspended in 400 µL of dd$H_2O$ and solubilized by agitation for 10 min. For the assay, 100 µL of 200 mM sodium phosphate/50 mM phenylalanine pH 7.0, 80 µL of dd$H_2O$ and 20 µL of the resuspension were added to the wells of a polyacrylate 96-well microtiter plate (Costar #3635, Corning). The reactions were mixed briefly and the activity was determined by tracking the absorbance at 290 nm over time (every 12-20 s over 5-20 min) using a SpectraMax® Plus 384 or a SpectraMax® 190 (Molecular Devices) absorbance microplate reader.

Resistance to Intestinal Fluids

PAL variant samples prepared as described in Example 3, were dissolved at 2 g/L in simulated intestinal fluids. PAL variants were dissolved into each of four simulated intestinal fluids: fasted state simulated intestinal fluid (sodium taurocholate 3 mM, lecithin 0.2 mM, maleic Acid 19.12 mM, sodium hydroxide 34.8 mM, sodium chloride 68.62 mM, pH 6.5), early fed state simulated intestinal fluid (sodium taurocholate 10 mM, lecithin 3 mM, maleic acid 28.6 mM, sodium hydroxide 52.5 mM, sodium chloride 145.2 glyceryl monocholate 6.5 mM sodium oleate 40 mM pH, 6.5), middle fed state simulated intestinal fluid (sodium taurocholate 7.5 mM, lecithin 2 mM, maleic acid 44 mM, sodium hydroxide 65.3 mM, sodium chloride 122.8 mM glyceryl monocholate 5 mM sodium oleate 30 mM pH 5.8), late fed state simulated intestinal fluid (sodium taurocholate 4.5 mM, lecithin 0.5 mM, maleic acid 58.09 mM, sodium hydroxide 72 mM, sodium chloride 51 mM glyceryl monocholate 1 mM sodium oleate 0.8 mM, pH 5.4). Porcine trypsin and bovine chymotrypsin (100 mg each) were dissolved in 2 ml of 100 mM sodium phosphate pH 7.0, and diluted to 1.5 mg/mL in each simulated fluid. Enzyme activity was measured in each simulated fluid over time, with and without trypsin and chymotrypsin. The reaction mixtures were incubated at 37° C. for 1-24 h in a Thermotron® HT shaker (Infors AJ185) at 400 rpm (1" throw). Then, 20 μL of the reaction was mixed with 80 μL of water and 100 μL of 100 mM sodium phosphate, 50 mM phenylalanine pH 7.0. Each solution was mixed briefly, and the activity was determined by tracking the absorbance at 290 nm over time (every 12-20 s over 5-20 min) using a SpectraMax® Plus 384 or a SpectraMax® 190 (Molecular Devices) absorbance microplate reader.

Example 5

Production of PAL Variants by Fermentation and Crystallization

Fermentation batch media ((NH$_4$)$_2$SO$_4$ 0.52 g/L, sodium citrate dihydrate 0.59 g/L, K$_2$HPO$_4$.3H$_2$O 7.5 g/L, KH$_2$PO$_4$ 3.7 g/L, yeast extract (Biospringer) 2.0 g/L, polypropylene glycol (PPG 2000) 0.3 ml/L, ammonium iron (III) citrate 0.05 g/L, Trace element stock solution 5.0 ml/L (CaCl$_2$.2H$_2$O 2.0 g/L. ZnSO$_4$.7H$_2$O 2.2 g/L, MnSO$_4$.H$_2$O 0.5 g/L, CuSO$_4$.5H$_2$O 1.0 g/L, (NH$_4$)$_6$ Mo$_7$O$_{24}$.4H$_2$O 0.1 g/L, Na$_2$B$_4$O$_7$.10H$_2$O 0.02 g/L, Adjust to pH 2-3 with H$_2$SO$_4$)) was supplemented with glucose at an initial concentration of approximately 10 g/L. After inoculation, the culture was controlled at 37° C. and a dissolved oxygen level not less than 45%. Fed-batch feeding (glucose monohydrate 500 g/L and magnesium sulfate, anhydrous 5.1 g/L) was initialized after depletion of the batch glucose as indicated by the spike in pH from set point of 7.00 to 7.05. The glucose feed was started at a rate of 0.41 ml/min and was increased to a final feed rate of 2.42 ml/min using an exponential profile over 12 hours. The feed was then kept at a constant rate of 2.42 ml/min for the remainder of the fermentation.

When a cumulative volume of 0.94 L of feed solution had been fed into the fermenter, the temperature was reduced to 30° C., and expression of the PAL variant was induced by addition of IPTG to a concentration of 1 mM. The expression phase ended when a total feed volume of 3.84 L was delivered to the fermenter. The total induction time was approximately 20 hours.

The cells were harvested by centrifugation (3752×g) for 10 min and the pellet used directly or stored frozen. Cold buffer (4° C.) consisting of 20 mM sodium phosphate, 150 mM NaCl pH 8.0 was used to resuspend the pellet to the original harvest volume. During the resuspension process, the pH was adjusted to 8.0±0.2 with NaOH. The suspension was cooled to 6° C. prior to homogenization. The intracellular enzyme was released from the cell using a high-pressure homogenizer (APV 1000) fitted with the appropriate cell disruption valve at 11,500±500 psig. Immediately after cell disruption, the homogenate was cooled to 15±2° C. and the pH of the homogenate was adjusted to 8.0±0.2 using NaOH. 10% w/v SuperFloc C581 was added to the cell homogenate. During the addition, the homogenate and C581 mixture was agitated to ensure complete blending. The suspension was incubated with agitation at 10±2° C. for 30 minutes, then heated to 55° C.±2° C. and held at 55° C. for 1 hour. The heat-treated suspension was cooled to 10±2° C. Separation of the solids from the liquid fraction was achieved by centrifugation. The homogenate was centrifuged at 5050×g for 35 min. A concentration step was performed in order to bring the protein concentration between 30 g/L and 40 g/L. The concentrated clarified lysate was dia-filtered with two volumes of 20 mM sodium phosphate/I50 mM NaCl pH 8.0. The concentration and buffer exchange of the solution was achieved with TangenX 30 kD PES NovaSet™-LS cassettes. The concentrate was filter-sterilized through a 0.2 μm Nalgene™ Rapid-Flow™ disposable filter unit with PES membrane.

Filtered concentrate and anti-solvent (0.1 M HEPES, 0.2 M NaCl pH 7.5 25% (w/v) PEG 3350) were heated separately to 40° C. Anti-solvent was added slowly to the PAL variant concentrate until a cloud point was sustained. Contact seeding was achieved by adding a small amount of crystals to the solution after it reached the cloud point. The solution was cooled linearly from 40° C. to 4° C. over 6 hours with periodical gentle mixing. The suspension was held for 12 to 24 hours at 4° C. The liquid was decanted and the crystalline solids washed with water to remove residual PEG. The washed crystalline solids were then lyophilized overnight to dryness.

Example 6

Screening Results

Variants of SEQ ID NO:4 ("Variant #1) were produced, including Variant #2 (SEQ ID NO:6), which has an additional F450A mutation incorporated into the sequence of Variant #1. Variants were also produced using Variant #2 as a starting backbone. These variants were tested for PAL activity after incubation in lyophilized form at 45° C. for 0 or 10 days as described in Example 2. In addition, variants with mutations of phenylalanine residues were tested at day 0 only. Retest data of active variants with corresponding fold-improvement over positive control (FIOP) are shown in Table 6.1, below. In this data set the positive control is Variant #2.

TABLE 6.1

Screening of Variants Derived From SEQ ID NO: 6 (Variant #2) for PAL Activity

| Variant # | Amino Acid Changes Relative to Variant #2 (SEQ ID NO: 6) | FIOP (T = 0) | FIOP (T = 10 days) |
|---|---|---|---|
| 3 | T102Q/D470E | + | ++ |
| 4 | I285R/D470E/T495A | ++ | ++ |
| 5 | T102Q | + | ++ |
| 6 | N44H/T239A/I285R/V469I/T495A | + | + |

TABLE 6.1-continued

Screening of Variants Derived From SEQ ID NO: 6 (Variant #2) for PAL Activity

| Variant # | Amino Acid Changes Relative to Variant #2 (SEQ ID NO: 6) | FIOP (T = 0) | FIOP (T = 10 days) |
|---|---|---|---|
| 7 | T239A/I285R | ++ | + |
| 8 | N44H/I56V | ++ | ++ |
| 9 | I285L/D470E | ++ | +++ |
| 10 | N44H/T239A/V469I/D470E | ++ | +++ |
| 11 | N44H/I56V/T102Q/T239A/I285L/V469I/D470E/T495A | + | ++ |
| 12 | N44H/T239A/I285L/D470E | ++ | ++ |
| 13 | I285L/V469I/D470E/T495A | + | + |
| 14 | N44C/T239A/T495A | + | ++ |
| 15 | N44H/T239A/T495A/S546A | + | + |
| 16 | N44H/V469I/D470E | ++ | + |
| 17 | N44H/T239A/D470E/S546A | ++ | + |
| 18 | T239A/I285L/V469I | + | ++ |
| 19 | T239A/V469I/D470E/T495A | ++ | + |
| 20 | V469I/D470E | ++ | + |
| 21 | N44H/T239A/I285R/D470E | ++ | + |
| 22 | N44H/T239A | + | + |
| 23 | F16S | ++++ | |
| 24 | F472A | +++ | |
| 25 | F16W | ++ | |
| 26 | F16A | ++ | |
| 27 | F16E | +++ | |
| 28 | F162W | ++ | |
| 29 | F482N | ++ | |
| 30 | F16V | +++ | |
| 31 | F16T | +++ | |
| 32 | F162Q | + | |
| 33 | F16W | ++ | |
| 34 | F16R | ++ | |
| 35 | F267V | ++ | |
| 36 | F267G | ++ | |
| 37 | F188I | ++ | |
| 38 | F16T | ++ | |
| 39 | F482C | ++ | |
| 40 | F264H | +++ | |
| 41 | F16N | +++ | |
| 42 | F16K/F150A | ++ | |
| 43 | L364E | + | +++ |
| 44 | N455S | ++ | + |
| 45 | L364S | + | ++++ |
| 46 | L364T | + | + |
| 47 | L364H | +++ | ++++ |
| 48 | I165L | ++ | ++ |

In the above Table, the activity fold improvement (FIOP) is compared to the backbone SEQ ID NO: 6 (Variant #2), and defined as follows: "−" = less than 0.2-fold activity; "+" = greater than 0.2-fold, but less than 1-fold activity; "++" = greater than 1-fold, but less than 1.25-fold increased activity; "+++" = greater than 1.25- fold, but less than 1.5-fold increased activity; and "++++" = greater than 1.5-fold activity.

Example 7

Confirmation of Hits

Based on the results shown in Table 6.1 above, the activities of the variants listed in Table 7.1 (below) were confirmed for enzyme samples prepared per the description in Example 3.

TABLE 7.1

Confirmation of Activity of Selected Variants Derived From Variant #2 (SEQ ID NO: 6)

| Variant # | Amino Acid Changes Relative to Variant #2 (SEQ ID NO: 6) | FIOP (T = 0) | FIOP (T = 10 days) |
|---|---|---|---|
| 2 | | + | + |
| 24 | F472A | ++ | +++ |
| 29 | F482N | ++ | + |
| 47 | L364H | ++ | + |

TABLE 7.1-continued

Confirmation of Activity of Selected Variants
Derived From Variant #2 (SEQ ID NO: 6)

| Variant # | Amino Acid Changes Relative to Variant #2 (SEQ ID NO: 6) | FIOP (T = 0) | FIOP (T = 10 days) |
|---|---|---|---|
| 23 | F16S | +++ | +++ |
| 40 | F264H | + | + |

In the above Table, the activity fold improvement (FIOP) is compared to the backbone SEQ ID NO: 6 (Variant #2), and defined as follows: "+" = greater than 0.95-fold, but less than 1-fold increased activity; "++" = greater than 1 fold, but less than 1.25-fold increased activity; and "+++" = greater than 1.25-fold increased activity.

Example 8

Screening Results for Additional Variants

Beneficial mutations identified as described in Example 6 were recombined into SEQ ID NO:8 (Variant No. 23) (shown in Tables 6.1 and 7.1), and the new variants were tested for PAL activity after incubation in lyophilized form at 45° C. for 0 and 10 days. Retest data of active variants with corresponding fold improvement over positive control (FIOP) are shown in Table 8.1, with Variant #23 as the positive control. In the following Table, some of the variants contain the same substitutions (i.e., are duplicates, such as variants 52 and 61), as these assay test results were obtained before sequencing data were obtained for the variants.

TABLE 8.1

Screening Results for Variants Derived from SEQ ID NO: 8 (Variant #23)

| Variant # | Amino Acid Changes Relative to Variant #23 (SEQ ID NO: 8) | FIOP (Primary T = 0) | FIOP (Primary T = 10 days) |
|---|---|---|---|
| 49 | S209P/I285R/L364H/D470E/T495A | ++++ | +++ |
| 50 | R204K/S209P/L364H | +++ | +++ |
| 51 | S209P/I285L/L364H/D470E | +++ | ++ |
| 52 | A47K/T239A/I285R/L364H | +++ | ++ |
| 53 | L364H | ++ | +++ |
| 54 | R204K/L364H | +++ | + |
| 55 | N44H/R204K/I285R/L364H/D470E/T495A | +++ | ++++ |
| 56 | A47K/R204K/I285R/L364H/T495A | +++ | +++ |
| 57 | L364H/D470E | +++ | ++ |
| 58 | R204K/S209P/L364H/T495A | +++ | ++ |
| 59 | A47K/S209P/T239A/L364H | ++ | ++ |
| 60 | S209P/L364H/T495A | +++ | ++ |
| 61 | A47K/T239A/I285R/L364H | +++ | ++ |
| 62 | N44H/A47K/L364H/D470E/T495A | +++ | ++ |
| 63 | A47K/D470E | +++ | ++ |
| 64 | I56V | +++ | ++ |
| 65 | T239A/L364H | +++ | +++ |
| 66 | K54E/I56V/R204K/S209P/D470E | +++ | +++ |
| 67 | R204K | +++ | ++ |
| 68 | N44H/K54P/I285R/D470E | +++ | +++ |
| 69 | R204K/D470E | +++ | +++ |
| 70 | S209P/L364H | +++ | ++ |
| 71 | R204K/S209P/T239A/I285R/D470E/T495A | ++ | +++ |
| 72 | A47K/K54P/S209P | +++ | +++ |
| 73 | K54E/I285R/D470E | +++ | +++ |
| 74 | D470E | ++ | ++ |
| 75 | R204K/T239A | +++ | ++ |
| 76 | K54P/D470E | +++ | +++ |
| 77 | S209P/D470E | ++ | ++ |
| 78 | N44H/S209P/I285R/T460G/T495A | ++++ | ++ |
| 79 | R204K/T239A/I285R | ++++ | +++ |
| 80 | K54E/I56V/R204K/S209P/T495A | +++ | +++ |
| 81 | R204K/T239A/I285R | +++ | ++ |
| 82 | R204K/T239A/I285R | ++ | ++ |
| 83 | N44H/K54P/I56V/R204K/T239A/D470E/T495A | +++ | ++ |
| 84 | A47K/R204K/S209P/T239A/I285R/T495A | ++ | ++ |
| 85 | N44H/R204K/S209P/I285R | ++ | ++ |
| 86 | K54E | ++ | ++ |
| 87 | K54P/I285L/D470E | ++ | ++ |
| 88 | K54P/I56V/R204K/T495A | +++ | ++ |
| 89 | K54P/I56V/I285L/D470E | +++ | +++ |
| 90 | N44H/A47K/R204K/S209P/I285R | ++ | ++ |
| 91 | K54P/I56V | ++++ | ++ |
| 92 | K54E/I56V/I285R/L364S/D470E | ++ | +++ |
| 93 | K54P/I56V/S209P/I562N | ++ | ++ |

TABLE 8.1-continued

Screening Results for Variants Derived from SEQ ID NO: 8 (Variant #23)

| Variant # | Amino Acid Changes Relative to Variant #23 (SEQ ID NO: 8) | FIOP (Primary T = 0) | FIOP (Primary T = 10 days) |
|---|---|---|---|
| 94 | K54P/T239A/T495A | ++ | ++ |
| 95 | I165L | ++ | ++ |
| 96 | N44H/K54P/I56V/R204K/T239A/I285R/L364S/T495A | ++++ | ++ |
| 97 | R204K/T239A/I285R | ++++ | +++ |
| 98 | S209P/I285R/L364E/D470E | ++ | ++ |
| 99 | K54P/I165L/R204K/S209P/T239A/I285R/D470E/T495A | ++ | ++ |
| 100 | S209P/I285R/L364E/D470E/T495A | +++ | ++ |
| 101 | R204K/S209P/L364E/T495A | ++ | ++ |
| 102 | N44C/I285R/L364E | ++++ | + |
| 103 | I285R/L364H | ++++ | +++ |
| 104 | I285R/L364H/T495A | +++ | +++ |
| 105 | L364H | +++ | ++ |
| 106 | N44C/T102Q/I285R/L364H | +++ | +++ |
| 107 | T495A | +++ | + |

In the above Table, the activity fold improvement (FIOP) is compared to the backbone (SEQ ID NO: 8 (Variant #23); and defined as follows: "−" = smaller than 0.2-fold activity; "+" = greater than 0.2-fold, but less than 1-fold activity; "++" = greater than 1-fold, but less than 1.25-fold increased activity; "+++" = greater than 1.25- fold activity, but less than 1.5-fold increased activity; and "++++" = greater than 1.5-fold activity.

Example 9

Removal of Phenylalanine Residues

Activity results for variants of SEQ ID NO:6 (Variant #2), in which phenylalanine residues were changed without resulting in a loss of activity (i.e., phenylalanine mutations that are either neutral or beneficial for activity) are shown in Table 9.1. As in Table 8.1, in the following Table, some of the variants contain the same substitutions, as these assay test results were obtained before sequencing data were obtained for the variants.

TABLE 9.1

Mutations of Phenylalanine Residues in SEQ ID NO: 6 (Variant #2) That Can be Replaced Without Loss of Function

| Variant # | Amino Acid Changes Relative to SEQ ID NO: 6 (Variant #2) | FIOP Primary (T = 0) |
|---|---|---|
| 108 | F162M | + |
| 32 | F162Q | + |
| 28 | F162W | + |
| 26 | F16A | + |
| 109 | F16A | + |
| 27 | F16E | + |
| 110 | F16K | + |
| 42 | F16K/F150A | + |
| 111 | F16L | + |
| 112 | F16M | + |
| 41 | F16N | + |
| 113 | F16P | + |
| 34 | F16R | + |
| 23 | F16S | + |
| 31 | F16T | + |
| 38 | F16T | + |
| 30 | F16V | + |
| 114 | F16V | + |
| 25 | F16W | + |
| 33 | F16W | + |
| 115 | F188A | + |
| 37 | F188I | + |
| 116 | F188N | + |
| 40 | F264H | + |
| 36 | F267G | + |
| 117 | F267L | + |
| 118 | F267Q | + |
| 119 | F267S | + |
| 35 | F267V | + |
| 120 | F398H | + |
| 121 | F434V | + |
| 24 | F472A | + |
| 122 | F472A | + |
| 123 | F472L | + |
| 124 | F472V | + |
| 39 | F482C | + |
| 29 | F482N | + |
| 125 | F482S | + |

In the above Table, the activity fold improvement (FIOP) is compared to the backbone SEQ ID NO: 6 (Variant #2), and defined as follows: "+" = similar activity to SEQ ID NO: 6 (variant #2) or SEQ ID NO: 8 (variant #23)

Example 10

Round 9 Screening Results

A combinatorial library was designed based on analysis of the previous results, using SEQ ID NO:12 (Variant #126) as the backbone, as Variant #126 showed improved storage stability as well as protease resistance in high throughput screening. The polynucleotide sequence encoding Variant #126 (SEQ ID NO:11) contains an a21t mutation compared to Variant #51 (SEQ ID NO:9). This variant was compared to wild-type AvPAL in various simulated intestinal fluids as described in Example 4. Active mutations with corresponding fold improvement in activity at T=0 and at T=10 days after incubation of lyophilized enzyme at 45° C. over Variant #126 are shown in Table 10.1, below. As in other Tables in the Examples, in the following Table, some of the variants contain the same substitutions, as these assay test results were obtained before sequencing data were obtained for the variants.

TABLE 10.1

Screening of Variants Derived From Variant #126 for PAL Activity

| Variant # | Amino Acid Changes Relative to SEQ ID NO: 12 | FIOP (T = 0) | FIOP (T = 10) |
|---|---|---|---|
| 127 | I56V/F162W/F398H | ++ | ++ |
| 128 | K54E/I56V/F162W/R204K/L285I | +++ | +++ |
| 129 | I56V/R204K/F398H/F472L | ++ | + |
| 130 | K54P/I56V/R204K/F398H/F472L | ++ | ++ |
| 131 | I56V/L285I | +++ | ++ |
| 132 | I56V/R204K/F398H | ++ | + |
| 133 | K54P/I56V/R204K/F398H | ++ | ++ |
| 134 | K54P/R204K/L285I/F398H/F472L | ++ | + |
| 135 | I56V/F398H | ++ | + |
| 136 | K54E/I56V/F398H/F472L | ++ | + |
| 137 | I56V/L285I/F398H/F472L | ++ | + |
| 138 | K54P/I56V/F398H | ++ | + |
| 139 | I56V/F398H | ++ | ++ |
| 140 | K54P/L285I/F398H | ++ | + |
| 141 | K54P/I56V/F162W/R204K/F398H | ++ | ++ |
| 142 | K54P/I56V/L285I | ++ | ++ |
| 143 | K54P/I56V/R204K/L285I | ++ | + |
| 144 | I56V/F398H/F472L | ++ | ++ |
| 145 | K54E/R204K/F398H | ++ | + |
| 146 | I56V/R204K/L285I | ++ | ++ |
| 147 | T201A/R204K/F398H | ++ | ++ |
| 148 | I56V/L285H | ++ | + |
| 149 | K54E/F162W/F398H | ++ | + |
| 150 | K54P/F162W/F398H | ++ | ++ |
| 151 | K54E/F162W/R204K/F398H | ++ | ++ |
| 152 | K54P/L285I/F398H/F472L | ++ | + |
| 153 | I56V/R204K/F398H/T460G | ++ | + |

In this Table, the activity fold improvement (FIOP) is compared to the backbone SEQ ID NO: 12 (Variant #126), and are defined as follows: "−" = less than 0.2-fold activity; "+" = greater than 0.2-fold, but less than 1-fold activity; "++" = greater than 1-fold, but less than 1.25-fold increased activity; and "+++" = greater than 1.25- fold activity.

Example 11

Plasma Phenylalanine Levels

Plasma samples were analyzed for phenylalanine and cinnamic acid. Internal standards were generated by dissolving phenylalanine or cinnamic acid in 50/50 acetonitrile:DMSO, and then diluted to working concentrations of 10-40,000 ng/ml in 50% acetonitrile. These samples were diluted into blank dog plasma (10 µL:90 µL) and then diluted with 300 µL of internal standard ($d_8$-Phe or $d_7$-CA at 250 ng/ml in acetonitrile) Animal plasma samples (20 µL) were diluted with acetonitrile (80 µL), and then diluted with 300 µL of internal standard. For analysis of phenylalanine concentrations, 30 µL of samples were injected using a Shimadzu HPLC/CTC Autosampler with Luna C18 column (2.1×100 mm, 5 µm). Samples were eluted using a gradient of 0.5% Formic acid, 5 mM ammonium acetate in water and 90% Acetonitrile and 10% water with 0.5% formic acid over 2.5 minutes, with phenylalanine eluting at 1.3 min.

For analysis of cinnamic acid, 30 µL of sample was injected using a Shimadzu HPLC/CTC Autosampler with Thermo Silica column (2.1×100 mm, 5 µm). Samples were eluted using a gradient of 5 mM ammonium acetate in water and 90% Acetonitrile/I0% water over 3.5 minutes, with cinnamic acid eluting at 2.3 min. Analytes were detected using an API-4000Q-trap Mass Spectrometer, performing MRM scans in ESI positive mode (phenylalanine) or negative mode (cinnamic acid). Transitions for isotopically labeled phenylalanine derivatives were 166.2/120.0, 171.2/125.1, and 174.2/128.2. Transitions for isotopically labeled cinnamic acid were 146.8/102.9, 151.9/107.9, and 153.9/110.1.

Example 12

Intestinal Activity of Variant #126 in a Dog Model

To assess the stability and activity of PAL variants as they transit through the gastrointestinal tract, beagle dogs were gavaged with purified enzyme variants. The effect of these variants on concentrations of phenylalanine and cinnamic acid in the dogs' blood was measured. Dogs were fasted overnight (12-16 hours) and through the study until 8 hours after enzyme dosing. All dogs were administered an oral dose of famotidine (40 mg/dog) 2 hours before study start the and again at +3 hours to minimize gastric acidification. Pre-study plasma samples (~2 mL) were taken at −2 hours (just prior to first famotidine dose), −30 min, and −10 min (the average of these 3 measurements was used to normalize post-dose values). Exactly 5 minutes after the dose of vehicle or Variant #126, at t=0, all dogs received a 900 mg/kg PO dose of powdered Goat Milk Esbilac (PetAg) protein in suspension (4 mL/kg). Additional plasma samples were taken at +15 min, +30 min, and +1, +2, +4, +6, +8, and +24 h post-treatment dose. Plasma samples were analyzed for Phe and CA as described in Example 11.

Figure 3:
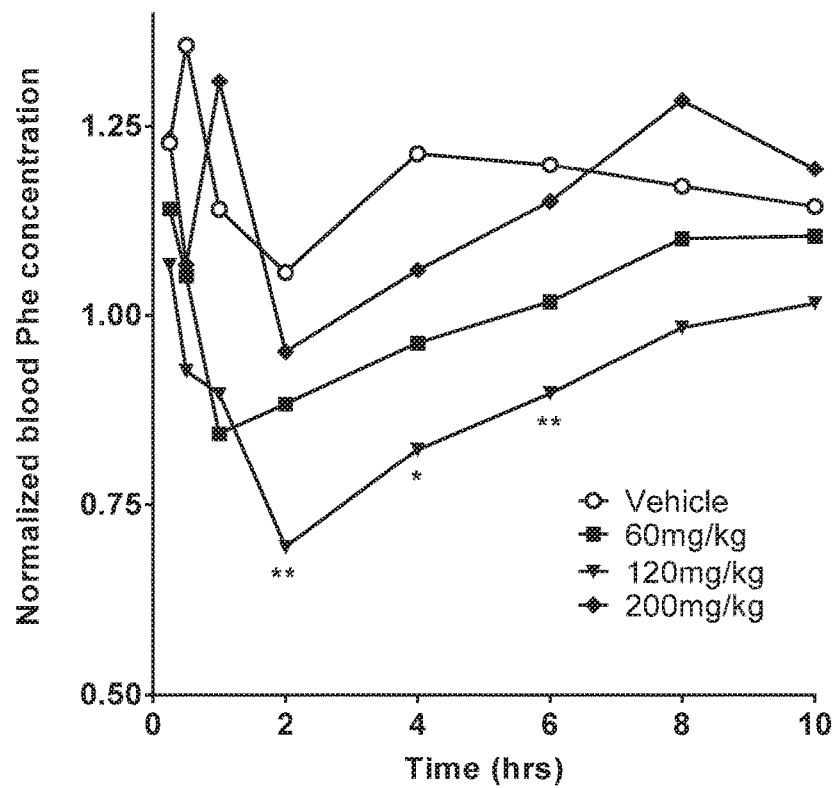
FIG. 3 is a graph showing the relative plasma phenylalanine levels in beagles for groups treated with various doses of Variant #126. Error bars are omitted for clarity (*: $p<0.05$, **: $p<0.01$).
Figure 4:
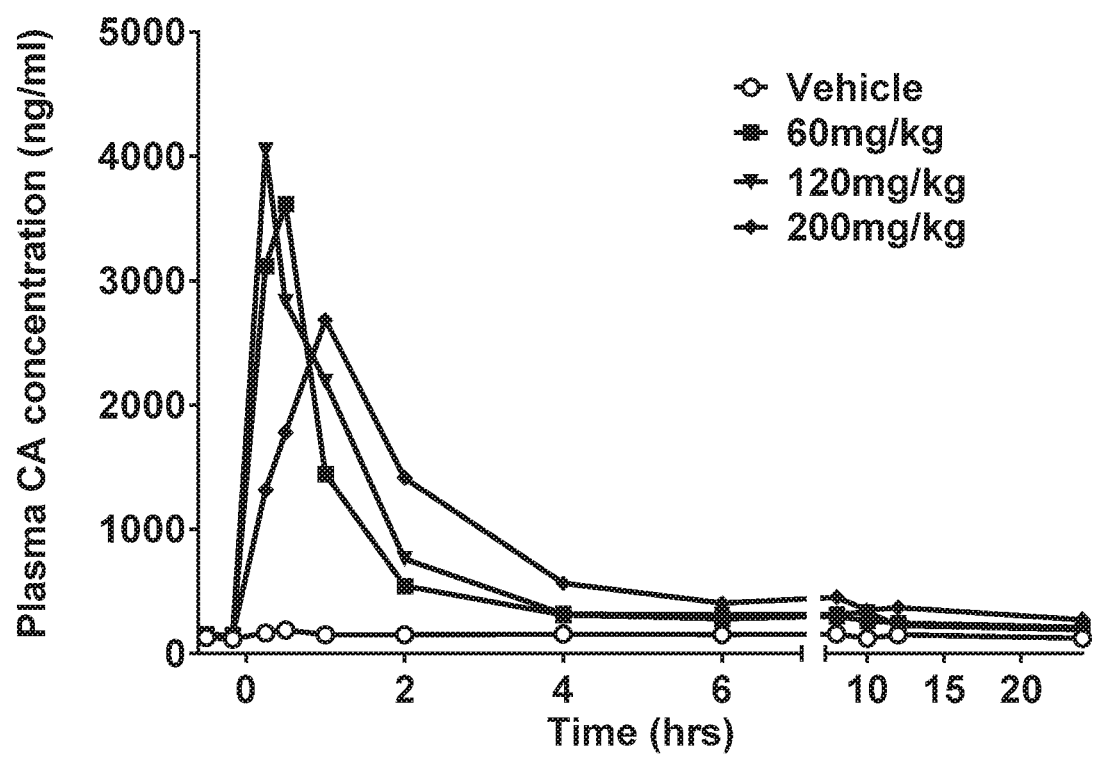
FIG. 4 is a graph showing the plasma CA levels in beagles for groups treated with various doses of Variant 126.
Figure 5:
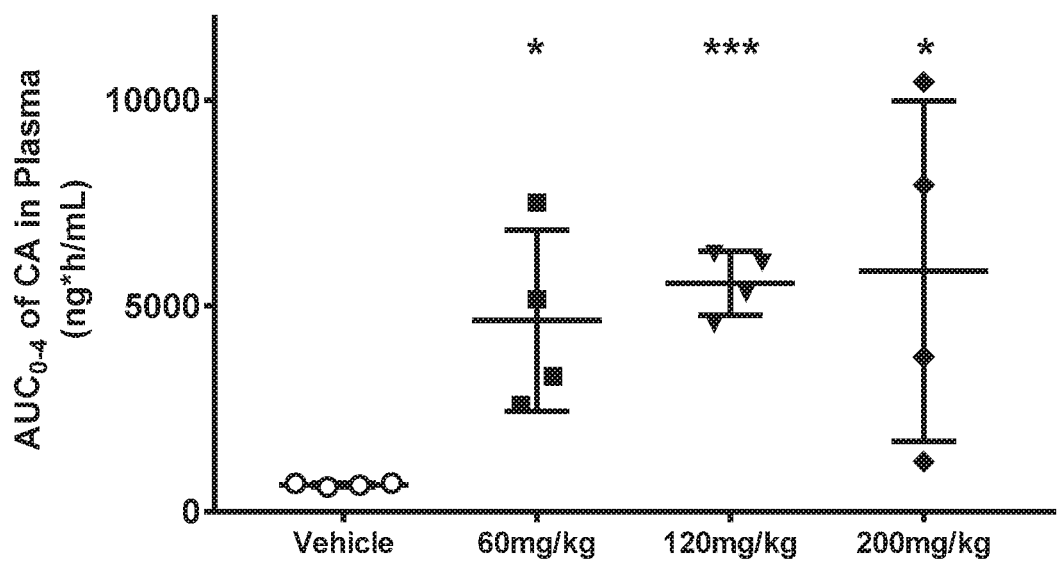
FIG. 5 is a graph showing the AUC for cinnamic acid in beagles in plasma levels for groups treated with various doses of Variant 126. Statistical significance provided for each group vs. vehicle (*: $p<0.05$, : $p<0.01$, *: $p<0.001$).

Results are shown in FIGS. 3, 4, and 5. In FIG. 3, the relative blood phenylalanine levels for the different groups are shown. Upon administration of vehicle a 1.35-fold increase in phenylalanine level was observed. Administration of all doses of Variant #126 suppress this immediate phenylalanine spike and led to a reduction in blood phenylalanine at t=1 hr, except for the 200 mg/kg group. At the 2 hr time point, the 120 mg/kg group showed a 34% reduction in blood phenylalanine.

FIG. 5 shows the cinnamic acid levels for the different groups. All groups except for vehicle showed rapid appearance of cinnamic acid upon administration of Variant #126 administration. The rapid onset of cinnamic acid formation leads to a $C_{max}$ at 15 minutes for the 120 mg/kg dose, at 30 min for PAL—the 60 mg/kg dose, and 1 hr for the 200 mg/kg dose Cinnamic acid is detected in plasma for 10 hrs in all dose groups. In the 200 mg/kg dose group, cinnamic acid continues to be above baseline for 24 hrs.

In FIG. 5 the amount of cinnamic acid formed during the first 4 hrs after Variant #126 administration was quantified as the AUC. The AUC for the 60, 120, and 200 mg/kg groups is statistically significantly different from the vehicle response.

Example 13

Intestinal Activity of Variant #126 in the Cynomolgus Monkey

Cynomolgus monkeys were used to assess the efficacy of Variant #126 to convert phenylalanine to cinnamic acid, by measuring plasma phenylalanine and cinnamic acid levels. Some of the animals received a dose of famotidine (20 mg per monkey) two hours prior to administration of Variant #126. Enzyme was administered by gavage and followed 5 minutes later with 900 mg/kg Goat Milk Esbilac (PetAg) protein to start the study (t=0). Plasma samples were analyzed for Phe and CA as described in Example 11.

Figure 6:
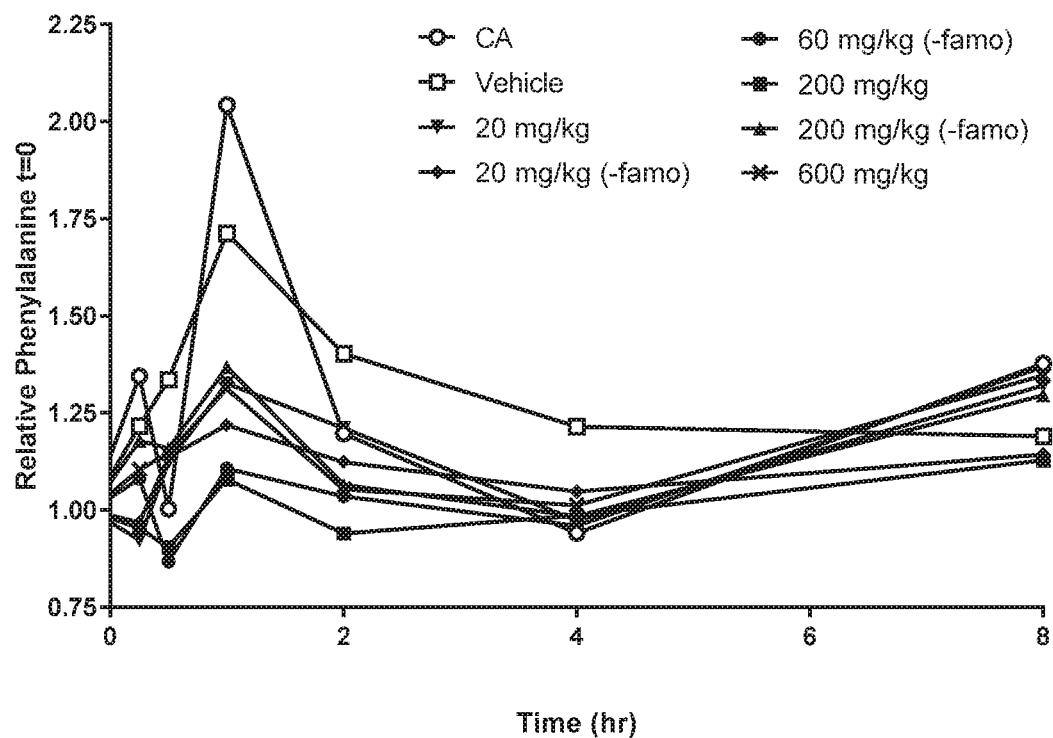
FIG. 6 is a graph showing the relative plasma phenylalanine (Phe) levels in cynomolgus monkeys for groups treated with various doses of Variant 126. Some groups were not pretreated with famotidine (-famo).

In FIG. 6, the relative plasma phenylalanine levels for the different groups are plotted over the first 8 hrs. after administration of Variant #126. Administration of vehicle led to a 1.7-fold increase in phenylalanine levels at 1 hr. Administration of all doses of Variant #126 suppressed this phenylalanine spike and led to a reduction in blood phenylalanine after 1 to 2 hrs. All groups treated with Variant #126, showed reduction of plasma phenylalanine between 20% and 38% at the 1 hour compared to vehicle.

Figure 7:
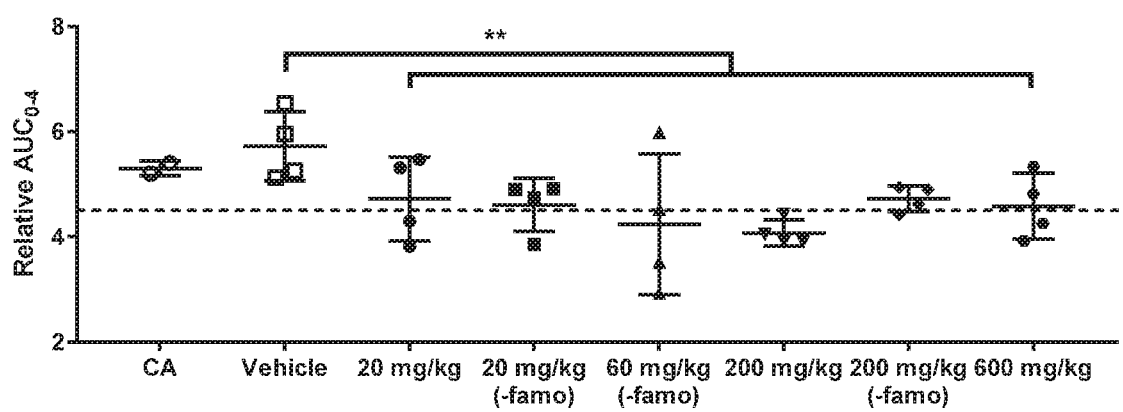
FIG. 7 is a graph showing the AUC of relative phenylalanine (Phe) in plasma of cynomolgus monkeys for groups treated with various doses of Variant 126. The dashed line represents the average AUC for all doses Variant 126 (**: $p<0.01$ for t-test between vehicle and all doses combined).

As shown in FIG. 7, the relative reduction of phenylalanine was quantified as the AUC for the 0 to 4 hrs time period. All groups dosed with Variant #126 had on average, a 22% lower AUC for phenylalanine compared to vehicle control.

Figure 8A:
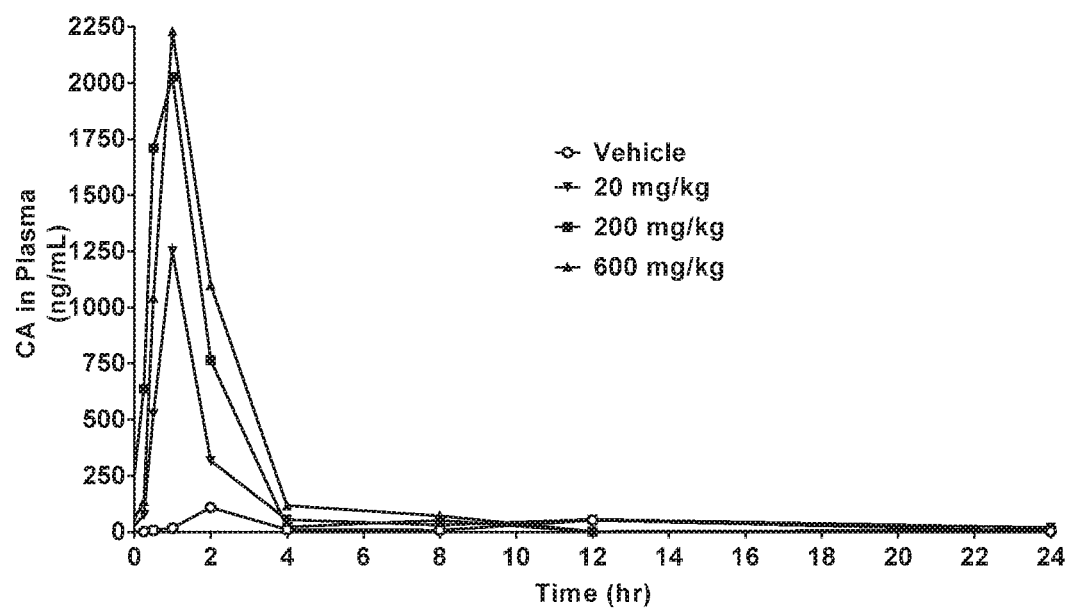
FIG. 8A is a graph showing the plasma cinnamic acid (CA) levels in cynomolgus monkeys for groups pre-treated with famotidine and who received various doses of Variant 126.
Figure 8B:
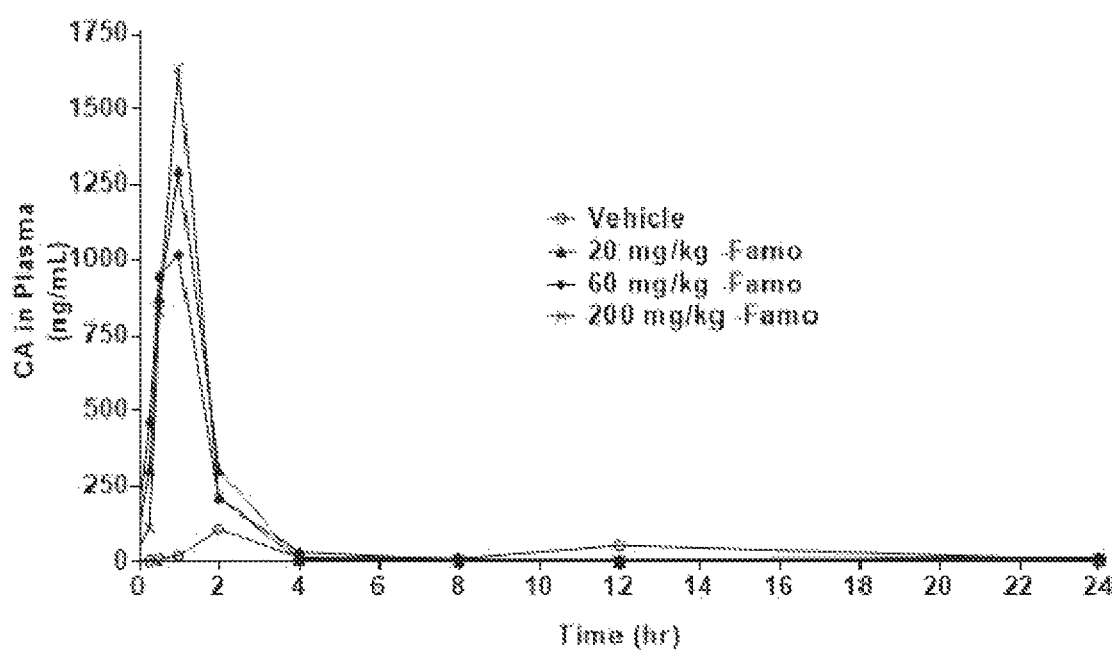
FIG. 8B is a graph showing the plasma cinnamic acid (CA) levels in cynomolgus monkeys for groups not pre-treated with famotidine and who received various doses of Variant 126.

As shown in FIG. 8, the time dependent cinnamic acid concentrations in plasma for the different dose groups are shown. FIG. 8 (top) shows cinnamic acid formation for groups that were pretreated with famotidine; FIG. 8 (bottom) shows such data for groups that were not treated with famotidine prior to dosing Cinnamic acid levels rose rapidly to reach $C_{max}$ at 1 hr, and then receded to close to baseline by 4 hrs. No cinnamic acid was detected in the vehicle control group.

Figure 9A:
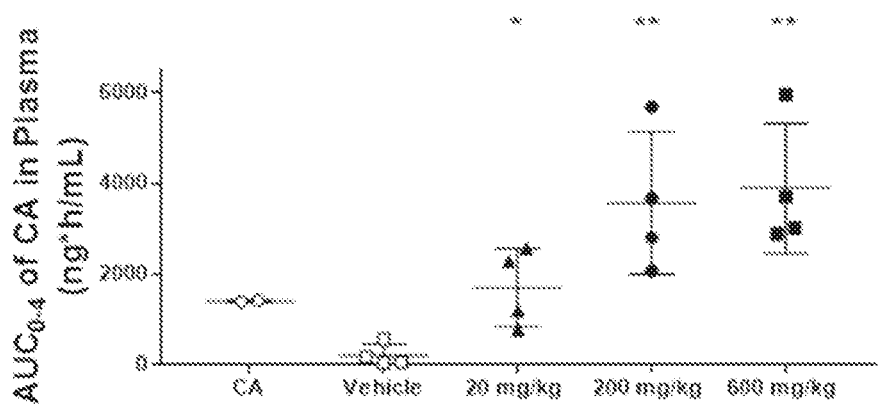
FIG. 9A is a graph showing the plasma cinnamic acid (CA) AUC over 0-4 hrs for groups of cynomolgus monkeys treated with various doses of Variant 126 in cynomolgus monkeys pre-treated with famotidine (top) or not (middle).
Figure 9B:
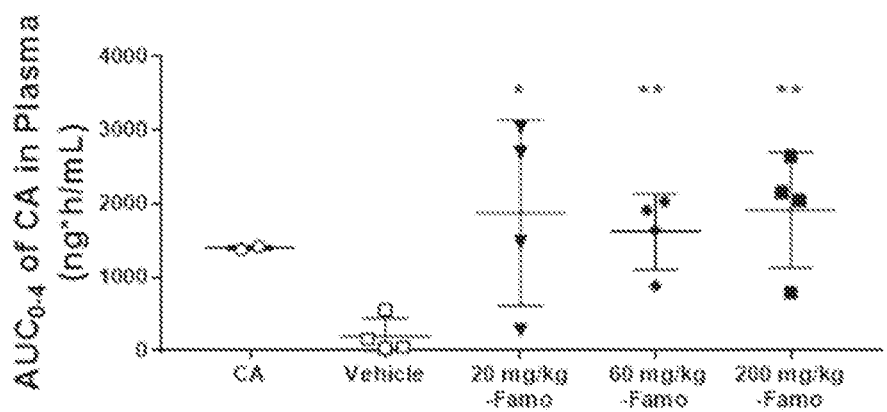
FIG. 9B is a graph showing the plasma cinnamic acid (CA) AUC over 0-4 hrs for groups of cynomolgus monkeys treated with various doses of Variant 126 in cynomolgus monkeys not pre-treated with famotidine.
Figure 9C:
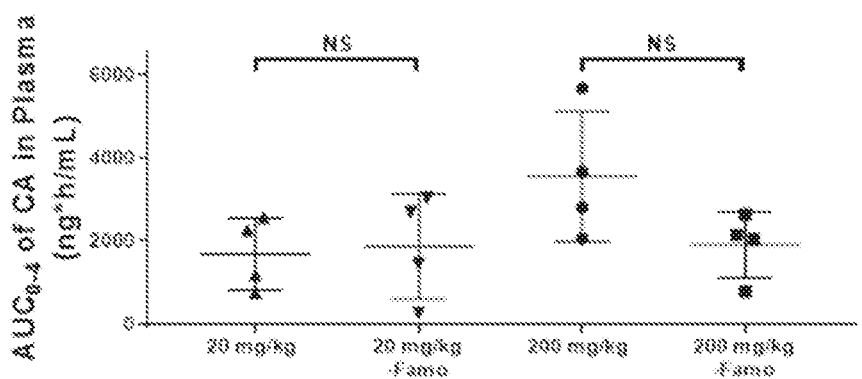
FIG. 9C is a graph providing a direct comparison of the 20 and 200 mg/kg groups that were not pre-treated with famotidine or received famotidine 2 hrs prior to dosing (bottom) (*: $p<0.05$, **: $p<0.01$).

As shown in FIG. 9, the formation of cinnamic acid during the initial 0 to 4 hrs after administration was quantified as the AUC. FIG. 9 (top) shows the AUC of groups pretreated with famotidine. A 10-fold increase in dose resulted in a less than 2-fold increase in cinnamic acid production. FIG. 9 (middle) shows the AUC of groups not pre-treated with famotidine and all groups showed a similar level of cinnamic acid formation. FIG. 9 (bottom) shows a direct comparison for groups that were dosed with the same amount of Variant #126 but either had been pretreated with famotidine or not. Famotidine treatment showed no statistically significant effect.

The results provided in FIGS. 6 through 9, show that oral administration of Variant #126 to healthy cynomolgus monkeys has a statistically significant effect on phenylalanine levels in plasma. In addition, upon oral administration of Variant #126 to cynomolgus monkeys, an amount of cinnamic acid is formed that corresponds to removal of approximately 9 mg/kg of phenylalanine. This amount is relevant in the context of phenylalanine intake by healthy individuals and PKU patients.

Example 14

Screening Results for Individual Mutation Variants

All amino acid mutations were individually made into Variant No. 126 (SEQ ID NO:12) and tested for PAL activity after incubation in lyophilized form at 45° C. for 0 (T=0) or 10 (T=10) days, and for protease stability, each was tested in triplicate. In the following Table, the mutations and assay results are provided.

TABLE 14.1

Screening of Variants Derived From Variant #126 (SEQ ID NO: 12) for PAL Activity

| Variant # | Amino Acid Changes (Relative to SEQ ID NO: 12) | FIOP (T = 0) | FIOP Protease | FIOP (T = 10) |
|---|---|---|---|---|
| 154 | S16E | +++ | +++ | + |
| 155 | S16I | +++ | +++ | + |
| 156 | S16L | ++ | ++ | + |
| 157 | S16D | ++ | ++ | + |
| 158 | S16K | ++ | ++ | + |
| 159 | S16H | ++ | ++ | + |
| 160 | S16M | ++ | ++ | + |
| 161 | Q214N | ++ | ++ | +++ |
| 162 | S16C | ++ | ++ | + |
| 163 | S16T | ++ | ++ | + |
| 164 | S16A | ++ | ++ | + |
| 165 | H364M | ++ | ++ | + |
| 166 | G307I | ++ | ++ | + |
| 167 | S16Q | ++ | ++ | + |
| 168 | V39Y | ++ | + | ++ |
| 169 | S16F | ++ | ++ | + |
| 170 | Q214C | ++ | ++ | ++ |
| 171 | S16N | ++ | + | + |
| 172 | S16R | ++ | ++ | + |
| 173 | S16P | ++ | + | + |
| 174 | R59F | ++ | + | ++ |
| 175 | Q503E | ++ | ++ | ++ |
| 176 | H364Y | ++ | ++ | + |
| 177 | S16V | ++ | + | + |
| 178 | L285N | ++ | + | + |
| 179 | K521Y | ++ | ++ | ++ |
| 180 | Q214D | + | ++ | + |
| 181 | S16W | + | ++ | + |
| 182 | H364E | + | + | + |
| 183 | H364L | + | + | + |
| 184 | L285C | + | + | + |
| 185 | G307Q | + | + | + |
| 186 | L285A | + | + | + |
| 187 | V39H | + | + | + |
| 188 | G307A | + | + | + |
| 189 | H364K | + | + | + |
| 190 | L285H | + | + | + |
| 191 | G307L | + | + | + |
| 192 | Q214W | + | + | + |
| 193 | G307H | + | + | + |
| 194 | R59N | + | + | + |
| 195 | A47D | + | + | + |
| 196 | V39N | + | + | + |
| 197 | G307E | + | + | + |
| 198 | V39Q | + | + | + |
| 199 | L285E | + | + | + |
| 200 | G307C | + | + | + |
| 201 | L285G | + | + | + |
| 202 | K54Q | + | + | + |
| 203 | H364N | + | + | + |
| 204 | K521G | + | + | + |
| 205 | H364T | + | + | + |
| 206 | V39R | + | + | + |
| 207 | Q214E | + | + | + |
| 208 | L285V | + | + | + |
| 209 | K54I | + | + | + |
| 210 | Q214G | + | + | + |
| 211 | H18V | + | + | + |
| 212 | L285M | + | + | + |
| 213 | K521P | + | + | + |
| 214 | A47E | + | + | + |
| 215 | H18P | + | + | + |
| 216 | Q503G | + | + | + |
| 217 | H364Q | + | + | + |
| 218 | K73I | + | + | + |
| 219 | G290D | + | ++ | + |
| 220 | Q503A | + | + | + |
| 221 | Q503V | + | + | + |
| 222 | Q503I | + | + | + |
| 223 | K521M | + | + | + |
| 224 | V407I | + | + | + |
| 225 | H364I | + | + | + |
| 226 | K54D | + | + | + |
| 227 | V39E | + | + | + |
| 228 | V39K | + | + | + |
| 229 | G307F | + | + | + |
| 230 | G307V | + | + | + |
| 231 | V39T | + | + | + |
| 232 | G307S | + | + | + |
| 233 | K73R | + | + | + |
| 234 | K521V | + | + | + |
| 235 | V39G | + | + | + |
| 236 | V407R | + | + | + |
| 237 | Q503Y | + | + | + |
| 238 | G307T | + | + | + |
| 239 | K521C | + | + | + |
| 240 | M305A | + | ++ | + |

TABLE 14.1-continued

Screening of Variants Derived From Variant #126 (SEQ ID NO: 12) for PAL Activity

| Variant # | Amino Acid Changes (Relative to SEQ ID NO: 12) | FIOP (T = 0) | FIOP Protease | FIOP (T = 10) |
|---|---|---|---|---|
| 241 | V407K | + | + | + |
| 242 | P565E | + | + | + |
| 243 | V39F | + | + | + |
| 244 | L285Q | + | + | + |
| 245 | M305N | + | + | + |
| 246 | K521L | + | + | + |
| 247 | H18N | + | + | + |
| 248 | V91T | + | + | + |
| 249 | K54C | + | + | + |
| 250 | P209S | + | + | + |
| 251 | K521A | + | + | + |
| 252 | L285T | + | + | + |
| 253 | A47S | + | + | + |
| 254 | K54A | + | + | + |
| 255 | P209N | + | + | + |
| 256 | G307M | + | + | + |
| 257 | L285K | + | + | + |
| 258 | V39W | + | + | + |
| 259 | K521H | + | + | + |
| 260 | K73V | + | + | + |
| 261 | K73Y | + | + | + |
| 262 | L285F | + | + | + |
| 263 | K521W | + | + | + |
| 264 | K54L | + | + | + |
| 265 | P565V | + | + | + |
| 266 | H18Q | + | + | + |
| 267 | Q503D | + | + | + |
| 268 | M305L | + | + | + |
| 269 | M305S | + | + | + |
| 270 | M305K | + | + | + |
| 271 | G290P | + | − | + |
| 272 | S524L | + | + | + |
| 273 | H18Y | + | + | + |
| 274 | G307R | + | + | + |
| 275 | K73L | + | + | + |
| 276 | V407C | + | + | + |
| 277 | K54M | + | + | + |
| 278 | G290S | + | ++ | + |
| 279 | H364V | + | + | + |
| 280 | P565D | + | + | + |
| 281 | V407M | + | + | + |
| 282 | G290Q | + | + | + |
| 283 | E470M | + | + | + |
| 284 | V91S | + | + | + |
| 285 | Q503S | + | + | + |
| 286 | H18D | + | + | + |
| 287 | K54T | + | + | + |
| 288 | K73E | + | + | + |
| 289 | E470T | + | + | + |
| 290 | P565G | + | + | + |
| 291 | K521E | + | + | + |
| 292 | G307Y | + | + | + |
| 293 | V407A | + | + | + |
| 294 | K54S | + | + | + |
| 295 | L285R | + | + | + |
| 296 | S524H | + | + | + |
| 297 | A47G | + | + | + |
| 298 | P565K | + | + | + |
| 299 | K54V | + | + | + |
| 300 | P209A | + | + | + |
| 301 | V39L | + | + | + |
| 302 | A47I | + | + | + |
| 303 | Q503T | + | + | + |
| 304 | S524W | + | + | + |
| 305 | Q214S | + | + | + |
| 306 | K73T | + | + | + |
| 307 | K521S | + | + | + |
| 308 | P565R | + | + | + |
| 309 | E470Q | + | + | + |
| 310 | Q503C | + | + | + |
| 311 | E470W | + | + | + |
| 312 | V39S | + | + | + |
| 313 | R59L | + | + | + |
| 314 | V39D | + | + | + |
| 315 | S524E | + | + | + |
| 316 | Q214T | + | + | + |
| 317 | A47K | + | + | + |
| 318 | K54E | + | + | + |
| 319 | V39M | + | + | + |
| 320 | L285S | + | + | + |
| 321 | K73A | + | + | + |
| 322 | K521D | + | + | + |
| 323 | S524R | + | + | + |
| 324 | Q503F | + | + | + |
| 325 | K521I | + | + | + |
| 326 | A47T | + | + | + |
| 327 | Q214A | + | + | + |
| 328 | Q214F | + | + | + |
| 329 | P565F | + | + | + |
| 330 | V39I | + | + | + |
| 331 | G290N | + | ++ | + |
| 332 | K73M | + | + | + |
| 333 | V407L | + | + | + |
| 334 | M305D | + | + | + |
| 335 | K73S | + | + | + |
| 336 | M305C | + | + | + |
| 337 | E470D | + | + | + |
| 338 | K54R | + | + | + |
| 339 | S524K | + | + | + |
| 340 | A47H | + | + | + |
| 341 | R59C | + | + | + |
| 342 | H364A | + | + | + |
| 343 | R59S | + | + | + |
| 344 | V91A | + | + | + |
| 345 | V407T | + | + | + |
| 346 | E470K | + | + | + |
| 347 | S524C | + | + | + |
| 348 | E470A | + | + | + |
| 349 | K54P | + | + | + |
| 350 | P565H | + | + | + |
| 351 | Q214H | + | + | + |
| 352 | A47Q | + | + | + |
| 353 | A47V | + | + | + |
| 354 | A47M | + | + | + |
| 355 | K54H | + | + | + |
| 356 | P209D | + | + | + |
| 357 | G307D | + | + | + |
| 358 | V407H | + | + | + |
| 359 | Q503M | + | + | + |
| 360 | K73G | + | + | + |
| 361 | M305E | + | + | + |
| 362 | E470I | + | + | + |
| 363 | K521F | + | + | + |
| 364 | Q503L | + | + | + |
| 365 | P565Q | + | + | + |
| 366 | G290K | + | + | + |
| 367 | P209Y | + | + | + |
| 368 | P565Y | + | + | + |
| 369 | P209G | + | + | + |
| 370 | A47R | + | + | + |
| 371 | Q214Y | + | + | + |
| 372 | A47W | + | + | + |
| 373 | Q503K | + | + | + |
| 374 | V407N | + | + | + |
| 375 | G307W | + | + | + |
| 376 | P209C | + | + | + |
| 377 | K73Q | + | + | + |
| 378 | E470H | + | + | + |
| 379 | E470R | + | + | + |
| 380 | R59G | + | + | + |
| 381 | K521N | + | + | + |
| 382 | P565S | + | + | + |
| 383 | P209E | + | + | + |
| 384 | G290T | + | ++ | + |
| 385 | V39C | + | + | + |
| 386 | E470V | + | + | + |
| 387 | K73C | + | + | + |
| 388 | S524G | + | + | + |

TABLE 14.1-continued

Screening of Variants Derived From Variant #126 (SEQ ID NO: 12) for PAL Activity

| Variant # | Amino Acid Changes (Relative to SEQ ID NO: 12) | FIOP (T = 0) | FIOP Protease | FIOP (T = 10) |
|---|---|---|---|---|
| 389 | L285W | + | + | + |
| 390 | K54N | + | + | + |
| 391 | E470G | + | + | + |
| 392 | V91C | + | + | + |
| 393 | L285D | + | + | + |
| 394 | K521R | + | + | + |
| 395 | K521T | + | + | + |
| 396 | P565N | + | + | + |
| 397 | R59A | + | + | + |
| 398 | K54Y | + | + | + |
| 399 | E470F | + | + | + |
| 400 | P565I | + | + | + |
| 401 | P209K | + | + | + |
| 402 | H18W | + | + | + |
| 403 | E470C | + | + | + |
| 404 | M305T | + | + | + |
| 405 | S524T | + | + | + |
| 406 | P209R | + | + | + |
| 407 | R59D | + | + | + |
| 408 | K521Q | + | + | + |
| 409 | Q503R | + | + | + |
| 410 | A47P | + | + | + |
| 411 | A47Y | + | + | + |
| 412 | S524V | + | + | + |
| 413 | R59H | + | + | + |
| 414 | V407Q | + | + | + |
| 415 | P565L | + | + | + |
| 416 | S524D | + | + | + |
| 417 | L285I | + | + | + |
| 418 | V39P | + | + | + |
| 419 | P209W | + | + | + |
| 420 | K54F | + | + | + |
| 421 | P209Q | + | + | + |
| 422 | Q214M | + | + | + |
| 423 | K73W | + | + | + |
| 424 | K73N | + | + | + |
| 425 | A47C | + | + | + |
| 426 | P209V | + | + | + |
| 427 | K73D | + | + | + |
| 428 | A47F | + | + | + |
| 429 | Q503N | + | + | + |
| 430 | P209I | + | + | + |
| 431 | R59K | + | + | + |
| 432 | Q214L | + | + | + |
| 433 | Q503H | + | + | + |
| 434 | M305Q | + | + | + |
| 435 | E470Y | + | + | + |
| 436 | S524M | + | + | + |
| 437 | V91P | + | + | + |
| 438 | K73H | + | + | + |
| 439 | S524A | + | + | + |
| 440 | R59E | + | + | + |
| 441 | P565M | + | + | + |
| 442 | S16G | + | + | + |
| 443 | P209H | + | + | + |
| 444 | S524I | + | + | + |
| 445 | P209F | + | + | + |
| 446 | P565T | + | + | + |
| 447 | R59P | + | + | + |
| 448 | K54W | + | + | + |
| 449 | H18R | + | + | + |
| 450 | K73F | + | + | + |
| 451 | G290H | + | + | + |
| 452 | M305H | + | + | + |
| 453 | R59Y | + | ++ | + |
| 454 | P209L | + | + | + |
| 455 | A47L | + | + | + |
| 456 | P565C | + | + | + |
| 457 | M305I | + | + | + |
| 458 | H18K | + | + | + |
| 459 | E470L | + | + | + |
| 460 | E470N | + | + | + |
| 461 | E470S | + | + | + |
| 462 | P209M | + | + | + |
| 463 | S524Y | + | + | + |
| 464 | S524Q | + | + | + |
| 465 | E470P | + | + | + |
| 466 | S524P | + | + | + |
| 467 | S524N | + | + | + |
| 468 | G290R | + | + | + |
| 469 | R59M | + | + | + |
| 470 | M305V | + | + | + |
| 471 | S524F | + | + | + |
| 472 | G290A | + | + | + |
| 473 | M305W | + | + | + |
| 474 | V39A | + | + | + |
| 475 | M305G | + | + | + |
| 476 | R59Q | + | + | + |
| 477 | G290C | + | + | + |
| 478 | R59W | + | + | + |
| 479 | A450R | + | + | + |
| 480 | V91G | + | + | + |
| 481 | V407Y | + | + | + |
| 482 | H18A | + | + | + |
| 483 | R59V | + | + | + |
| 484 | R59I | + | + | + |
| 485 | M305F | + | + | + |
| 486 | H18F | + | + | + |
| 487 | V407F | + | + | + |
| 488 | V91I | + | + | + |
| 489 | A450G | + | + | + |
| 490 | H364C | + | + | + |
| 491 | P565W | + | + | + |
| 492 | A450S | + | + | + |
| 493 | P209T | + | + | + |
| 494 | H18S | + | + | + |
| 495 | G290E | + | + | + |
| 496 | R59T | + | − | + |
| 497 | H18I | + | + | + |
| 498 | A450T | + | + | + |
| 499 | P565A | + | + | + |
| 500 | M305Y | + | + | + |
| 501 | H18E | + | + | + |
| 502 | G307N | + | + | + |
| 503 | A450V | + | + | + |
| 504 | Q214I | + | + | + |
| 505 | V91N | + | + | + |
| 506 | H18G | + | + | + |
| 507 | M305P | + | + | + |
| 508 | A450K | + | + | + |
| 509 | K73P | + | − | + |
| 510 | G290M | + | + | + |
| 511 | V407S | + | + | + |
| 512 | G290Y | + | + | + |
| 513 | Q214V | + | + | + |
| 514 | H18T | + | + | + |
| 515 | Q214P | + | − | + |
| 516 | H18C | + | + | + |
| 517 | Q214K | + | + | + |
| 518 | G290F | + | + | + |
| 519 | A450M | + | + | + |
| 520 | A450N | + | + | + |
| 521 | A450Q | + | + | + |
| 522 | Q503P | + | + | + |
| 523 | V91F | + | − | + |
| 524 | V91L | + | + | + |
| 525 | V91D | + | + | + |
| 526 | H18M | + | + | + |
| 527 | Q214R | + | + | + |
| 528 | A450C | + | + | + |
| 529 | L285Y | + | + | + |
| 530 | L285P | + | + | − |
| 531 | A450H | + | + | + |
| 532 | H364S | + | + | + |
| 533 | A450F | + | + | + |
| 534 | G290L | + | + | + |
| 535 | G290V | + | + | + |
| 536 | A450I | + | + | + |

TABLE 14.1-continued

Screening of Variants Derived From Variant #126 (SEQ ID NO: 12) for PAL Activity

| Variant # | Amino Acid Changes (Relative to SEQ ID NO: 12) | FIOP (T = 0) | FIOP Protease | FIOP (T = 10) |
|---|---|---|---|---|
| 537 | V407G | + | + | − |
| 538 | V91M | + | + | + |
| 539 | A450E | + | + | + |
| 540 | V91H | + | + | + |
| 541 | V91Y | + | − | + |
| 542 | G307K | + | + | + |
| 543 | A450Y | + | + | + |
| 544 | G290I | + | + | + |
| 545 | H18L | + | + | + |
| 546 | V91Q | + | + | + |
| 547 | V407P | + | + | + |
| 548 | G290W | + | + | + |
| 549 | H364F | + | + | − |
| 550 | V91E | + | + | + |
| 551 | V91K | + | + | − |
| 552 | A450W | + | + | + |
| 553 | M305R | + | + | + |
| 554 | V91R | + | − | + |
| 555 | A450D | − | + | − |
| 556 | K54G | − | + | + |
| 557 | V91W | − | − | − |
| 558 | V407E | − | − | − |
| 559 | G307P | − | − | − |
| 560 | H364G | − | − | − |
| 561 | V407D | − | − | − |
| 562 | V407W | − | − | − |
| 563 | H364D | − | − | − |
| 564 | S16Y | − | − | − |
| 565 | H364P | − | − | − |
| 566 | A450P | − | − | − |
| 567 | Q503W | − | − | − |
| 568 | A47N | − | − | − |
| 569 | H364R | − | − | − |
| 570 | H364W | − | − | − |
| 571 | A450L | − | − | − |

In the above Table, the activity fold improvement (FIOP) is compared to SEQ ID NO: 12 (Variant #126), and defined as follows: "−" = less than 0.2-fold activity; "+" = greater than 0.2-fold, but less than 1-fold activity; "++" = greater than 1-fold, but less than 1.25-fold increased activity; and "+++" = greater than 1.25- fold activity.

Example 15

Combinatorial Screening Results for Additional Variants

Mutations identified in Variant No. 126 (SEQ ID NO:12) were added combinatorially in SEQ ID NO:2. The new variants were tested for PAL activity after incubation in lyophilized form at 45° C. for 0 (T=0) or 7 days (T=7), as well as stability in the presence of protease. Data of variants with corresponding fold improvement over positive control (FIOP) are shown in Table 15.1, with SEQ ID NO:12 (Variant #126) as the positive control.

TABLE 15.1

Screening of Variants for PAL Activity

| Variant # | Amino Acid Sequence Changes (Relative to SEQ ID NO: 2) | FIOP (T = 0) | FIOP Protease | FIOP (T = 7) |
|---|---|---|---|---|
| 572 | A39V/G59R/A202T/L407V/T524S/C565P | − | − | − |
| 573 | A39V/G59R/L364H/F450A/D470E/C565P | − | − | − |
| 574 | A39V/G59R/S73K/S209P/I285L/N290G/R305M/H307G/ L364H/L407V/F450A/D470E/C503Q/Q521K/T524S/C565P | + | + | + |
| 575 | A39V/L214Q/H307G/C503Q/T524S | − | + | − |
| 576 | A39V/L214Q/I285L/N290G/R305M/H307G/L364H/C503Q/ Q521K/T524S | + | − | + |
| 577 | A39V/L47A/A91V/L214Q | − | − | − |
| 578 | A39V/L47A/A91V/S209P/L214Q/I285L/N290G/R305M/ H307G/L364H/L407V/F450A/D470E/C503Q/Q521K/T524S/ C565P | + | + | + |
| 579 | A39V/L47A/G59R/A91V/S209P/L214Q/I285L/N290G/R305M/ H307G/L364H/F450A/D470E/C503Q/Q521K/T524S | + | − | + |
| 580 | A39V/L47A/G59R/A91V/S98G/S209P/L214Q/I285L/N290G/ R305M/H307G/L364H/P403T/L407V/F450A/D470E/ C503Q/T524S/C565P | + | + | + |
| 581 | A39V/L47A/G59R/S73K/A91V/S209P/L214Q/I285L/N290G/ R305M/H307G/L364H/L407V/F450A/D470E/C503Q/ Q521K/T524S | + | + | + |
| 582 | A39V/L47A/I285L/C503Q | − | − | − |
| 583 | A39V/L47A/S73K/A91V/L214Q/I285L/N290G/R305M/ H307G/L364H/L407V/F450A/D470E/C503Q/Q521K/T524S/ C565P | + | − | ++ |
| 584 | A39V/L47A/S73K/A91V/L214Q/I285L/N290G/R305M/ L364H/L407V/F450A/C503Q/Q521K/T524S | + | + | + |
| 585 | A39V/L47A/T54K/A91V/L214Q/I285L/N290G/H307G/ L364H/D470E/C503Q/Q521K/T524S | + | + | + |
| 586 | A39V/L47A/T54K/A91V/S209P/I285L/N290G/H307G/L364H/ L407V/F450A/D470E/C503Q/Q521K/T524S/C565P | + | − | + |
| 587 | A39V/L47A/T54K/A91V/S209P/L214Q/I285L/R305M/ H307G/L407V/C503Q/Q521K/C565P | + | + | + |
| 588 | A39V/L47A/T54K/G59R/A91V/S98G/S209P/L214Q/I285L/ N290G/R305M/H307G/L364H/L407V/F450A/D470E/C503Q/ T524S | + | − | + |
| 589 | A39V/L47A/T54K/G59R/S73K/A91V/I285L/N290G/R305M/ H307G/F450A/D470E/C503Q/Q521K/T524S | + | − | + |

TABLE 15.1-continued

Screening of Variants for PAL Activity

| Variant # | Amino Acid Sequence Changes (Relative to SEQ ID NO: 2) | FIOP (T = 0) | FIOP Protease | FIOP (T = 7) |
|---|---|---|---|---|
| 590 | A39V/L47A/T54K/G59R/S73K/A91V/I285L/N290G/R305M/H307G/L364H/F450A/D470E/C503Q/Q521K/C565P | + | + | + |
| 591 | A39V/L47A/T54K/G59R/S73K/A91V/I285L/N290G/R305M/H307G/L364H/L407V/D470E/C503Q/Q521K/T524S/C565P | + | + | + |
| 592 | A39V/L47A/T54K/G59R/S73K/A91V/I285L/N290G/R305M/H307G/L364H/L407V/F450A/D470E/C503Q/Q521K/T524S/C565P | + | + | + |
| 593 | A39V/L47A/T54K/G59R/S73K/A91V/I285L/N290G/R305M/H307G/L407V/F450A/D470E/C503Q/Q521K/T524S/C565P | + | − | + |
| 594 | A39V/L47A/T54K/G59R/S73K/A91V/L214Q/I285L/N290G/L364H/F450A/D470E/C503Q/Q521K/T524S/C565P | + | − | + |
| 595 | A39V/L47A/T54K/G59R/S73K/A91V/L214Q/I285L/N290G/R305M/H307G/L407V/F450A/D470E/C503Q/Q521K/T524S/C565P | + | − | + |
| 596 | A39V/L47A/T54K/G59R/S73K/A91V/L214Q/I285L/N290G/R305M/H307G/L407V/R412H/F450A/D470E/C503Q/Q521K/T524S/C565P | + | + | + |
| 597 | A39V/L47A/T54K/G59R/S73K/A91V/S209P/I285L/N290G/H307G/L407V/F450A/D470E/C503Q/Q521K/C565P | + | + | + |
| 598 | A39V/L47A/T54K/G59R/S73K/A91V/S209P/I285L/N290G/L364H/F450A/D470E/C503Q/Q521K/T524S | + | − | + |
| 599 | A39V/L47A/T54K/G59R/S73K/A91V/S209P/I285L/N290G/R305M/L364H/L407V/F450A/D470E/C503Q/Q521K/T524S/C565P | + | + | + |
| 600 | A39V/L47A/T54K/G59R/S73K/A91V/S209P/L214Q/I285L/N290G/R305M/L364H/L407V/C503Q/Q521K/T524S/C565P | + | + | + |
| 601 | A39V/L47A/T54K/G59R/S73K/A91V/S209P/L214Q/N290G/R305M/H307G/L364H/L407V/D470E/C503Q/Q521K/T524S/C565P | + | + | + |
| 602 | A39V/L47A/T54K/G59R/S73K/A91V/S209P/L214Q/N290G/R305M/H307G/L364H/L407V/F450A/D470E/C503Q | + | − | + |
| 603 | A39V/L47A/T54K/G59R/S73K/S209P/I285L/N290G/R305M/H307G/L364H/F450A/D470E/C503Q/Q521K/T524S | + | + | + |
| 604 | A39V/L47A/T54K/G59R/S73K/S209P/L214Q/I285L/N290G/H307G/L407V/F450A/C503Q/Q521K/T524S | + | + | + |
| 605 | A39V/L47A/T54K/S73K/A91V/I285L/N290G/R305M/H307G/L364H/L407V/F450A/D470E/C503Q/Q521K/T524S/C565P | + | − | + |
| 606 | A39V/L47A/T54K/S73K/A91V/L214Q/I285L/N290G/R305M/L364H/L407V/F450A/C503Q/T524S | + | + | + |
| 607 | A39V/L47A/T54K/S73K/A91V/S209P/I285L/N290G/R305M/H307G/L364H/L407V/D470E/C503Q/Q521K/T524S | + | + | + |
| 608 | A39V/L47A/T54K/S73K/A91V/S209P/I285L/N290G/R305M/L364H/F450A/D470E/C503Q/Q521K/T524S | + | + | + |
| 609 | A39V/L47A/T54K/S73K/A91V/S209P/L214Q/I285L/N290G/R305M/H307G/L407V/D470E/C503Q/Q521K/T524S/C565P | + | + | + |
| 610 | A39V/S209P/F450A/L407V/D470E/C503Q | − | − | − |
| 611 | A39V/S209P/L214Q/L407V/F450A/D470E/C503Q/Q521K | − | − | − |
| 612 | A39V/S73K/N290G/H307G/L364H/L407V/F450A/T524S/C565P | − | + | − |
| 613 | A39V/T54K/G59R/A91V/S209P/L214Q/I285L/N290G/R305M/H307G/L364H/L407V/D470E/C503Q/T524S/C565P | + | − | + |
| 614 | A39V/T54K/G59R/A91V/S98G/I285L/N290G/C503Q/Q521K/T524S/C565P | − | − | − |
| 615 | A39V/T54K/G59R/A91V/S98G/S209P/L287Q/N290V/S291G/H307G/L364H/L407V/F450A/C503Q/Q521K/T524S | − | ++ | − |
| 616 | A39V/T54K/G59R/S73K/A91V/I285L/N290G/H307G/L364H/L407V/F450A/C503Q/T524S | + | + | + |
| 617 | A39V/T54K/G59R/S73K/A91V/S209P/I285L/N290G/R305M/L364H/L407V/F450A/D470E/C503Q/Q521K/T524S/C565P | + | + | + |
| 618 | A39V/T54K/G59R/S73K/A91V/S209P/L214Q/I285L/N290G/L364H/L407V/D470E/C503Q/T524S/C565P | + | + | + |
| 619 | A39V/T54K/G59R/S73K/A91V/S209P/L214Q/I285L/N290G/R305M/H307G/L364H/L407V/D470E/C503Q | + | + | + |
| 620 | A39V/T54K/G59R/S73K/A91V/S209P/L214Q/I285L/N290G/R305M/H307G/L364H/L407V/F450A/D470E/C503Q/Q521K/T524S/C565P | + | + | + |
| 621 | A39V/T54K/G59R/S73K/A91V/S209P/L214Q/N290G/R305M/H307G/L407V/C503Q/Q521K/T524S/C565P | + | + | + |
| 622 | A39V/T54K/G59R/S73K/A91V/S209P/L214Q/N290G/R305M/L407V/F450A/C503Q/T524S/C565P | + | + | + |
| 623 | A39V/T54K/G59R/S73K/N290G/R305M/H307G/L364H/L407V/D470E/C503Q/Q521K/T524S/C565P | + | + | + |
| 624 | A39V/T54K/G59R/S73K/S209P/L214Q/I285L/N290G/R305M/H307G/L364H/L407V/F450A/C503Q/Q521K/C565P | + | + | + |
| 625 | A39V/T54K/G59R/S73K/S98G/S209P/L214Q/I285L/N290G/R305M/H307G/L364H/F450A/D470E/C503Q | + | + | + |

TABLE 15.1-continued

Screening of Variants for PAL Activity

| Variant # | Amino Acid Sequence Changes (Relative to SEQ ID NO: 2) | FIOP (T = 0) | FIOP Protease | FIOP (T = 7) |
|---|---|---|---|---|
| 626 | A39V/T54K/S73K/A91V/S209P/L214Q/I285L/N290G/R305M/L364H/C503Q/T524S/C565P | + | + | + |
| 627 | A91V/A97T/S209P/I285L | − | − | − |
| 628 | A91V/S209P/L214Q/D470E/C565P | − | − | − |
| 629 | A91V/S209P/L214Q/F450A/Q521K/T524S/C565P | − | − | − |
| 630 | A91V/S209P/L214Q/L364H/L407V/F450A/D470E/C565P | − | − | − |
| 631 | A91V/S209P/L214Q/L407V/C503Q/C565P | − | − | − |
| 632 | A91V/S209P/L214Q/Q255L/I285L/N290G/H307G/F450A | − | − | − |
| 633 | A91V/S209P/L407V | − | − | − |
| 634 | C503Q | − | − | + |
| 635 | D55H/N290G/R305M/L364H/F450A/C503Q | − | − | − |
| 636 | F16S/A39V/D55E/G59R/C503Q/C565P | − | − | − |
| 637 | F16S/A39V/L214Q/L407V/C503Q/C565P | − | − | − |
| 638 | F16S/A39V/L214Q/Q255R/L407V/C565P | − | − | − |
| 639 | F16S/A39V/L214Q/T524S | − | − | − |
| 640 | F16S/A39V/L407V/F450A/D470E/Y475F | − | − | − |
| 641 | F16S/A39V/L47A/G59R/S73K/S209P/L214Q/I285L/N290G/R305M/H307G/L364H/L407V/F450A/D470E/C503Q/T524S/C565P | ++ | + | ++ |
| 642 | F16S/A39V/L47A/S73K/A91V/I285L/N290G/H307G/L364H/F450A/D470E/C503Q/Q521K/T524S/C565P | + | + | + |
| 643 | F16S/A39V/L47A/S73K/S209P/L214Q/I285L/N290G/R305M/H307G/L364H/L407V/F450A/D470E/C503Q/Q521K/T524S | ++ | − | ++ |
| 644 | F16S/A39V/L47A/T54K/A91V/S209P/L214Q/I285L/N290G/R305M/H307G/L364H/L407V/F450A/D470E/C503Q/Q521K/T524S | ++ | + | ++ |
| 645 | F16S/A39V/L47A/T54K/G59R/L214Q/L364H/F450A/D470E/C503Q/Q521K/T524S | + | − | + |
| 646 | F16S/A39V/L47A/T54K/G59R/S73K/A91V/L214Q/I285L/N290G/H307G/L364H/L407V/F450A/C503Q/Q521K/T524S/C565P | + | − | + |
| 647 | F16S/A39V/L47A/T54K/G59R/S73K/A91V/L214Q/I285L/N290G/R305M/H307G/F450A/D470E/C503Q/Q521K/T524S/C565P | + | + | + |
| 648 | F16S/A39V/L47A/T54K/G59R/S73K/A91V/L214Q/I285L/N290G/R305M/L364H/L407V/F450A/C503Q/T524S/C565P | + | ++ | + |
| 649 | F16S/A39V/L47A/T54K/G59R/S73K/A91V/L214Q/N290G/L364H/L407V/F450A/D470E/T524S/C565P | + | − | + |
| 650 | F16S/A39V/L47A/T54K/G59R/S73K/A91V/S209P/I285L/N290G/R305M/H307G/L364H/L407V/D470E/C503Q/Q521K/T524S | + | ++ | + |
| 651 | F16S/A39V/L47A/T54K/G59R/S73K/A91V/S209P/L214Q/I285L/N290G/H307G/F450A/D470E/C503Q/Q521K/T524S/C565P | + | + | + |
| 652 | F16S/A39V/L47A/T54K/G59R/S73K/A91V/S209P/L214Q/I285L/N290G/R305M/H307G/L364H/L407V/D470E/C503Q/Q521K/T524S/C565P | + | + | + |
| 653 | F16S/A39V/L47A/T54K/G59R/S73K/A91V/S209P/L214Q/I285L/N290G/R305M/H307G/L364H/L407V/F450A/C503Q/Q521K/T524S/C565P | + | ++ | + |
| 654 | F16S/A39V/L47A/T54K/G59R/S73K/A91V/S209P/L214Q/I285L/N290G/R305M/H307G/L364H/L407V/F450A/D470E/C503Q/Q521K/T524S | ++ | ++ | + |
| 655 | F16S/A39V/L47A/T54K/G59R/S73K/A91V/S209P/L214Q/I285L/N290G/R305M/H307G/L364H/L407V/F450A/D470E/C503Q/Q521K/T524S/C565P | ++ | + | + |
| 656 | F16S/A39V/L47A/T54K/G59R/S73K/A91V/S209P/L214Q/I285L/N290G/R305M/L364H/L407V/C503Q/Q521K/T524S/C565P | + | + | + |
| 657 | F16S/A39V/L47A/T54K/G59R/S73K/A91V/S209P/L214Q/I285L/N290G/R305M/L364H/L407V/F450A/C503Q/Q521K | ++ | + | ++ |
| 658 | F16S/A39V/L47A/T54K/G59R/S73K/A91V/S209P/L214Q/I285L/N290G/R305M/L364H/L407V/F450A/D470E/C503Q/Q521K/T524S | + | + | ++ |
| 659 | F16S/A39V/L47A/T54K/G59R/S73K/A91V/S209P/L214Q/N290G/R305M/H307G/L364H/L407V/F450A/D470E/C503Q/Q521K/T524S/C565P | + | + | + |
| 660 | F16S/A39V/L47A/T54K/G59R/S73K/A91V/S209P/L214Q/N290G/R305M/L407V/F450A/D470E/C503Q/Q521K/T524S/C565P | + | + | + |
| 661 | F16S/A39V/L47A/T54K/G59R/S73K/A91V/S98G/S209P/L214Q/I285L/N290G/H307G/L364H/L407V/F450A/D470E/Q521K/T524S/C565P | + | − | + |

TABLE 15.1-continued

Screening of Variants for PAL Activity

| Variant # | Amino Acid Sequence Changes (Relative to SEQ ID NO: 2) | FIOP (T = 0) | FIOP Protease | FIOP (T = 7) |
|---|---|---|---|---|
| 662 | F16S/A39V/L47A/T54K/G59R/S73K/A91V/S98G/S209P/L214Q/I285L/N290G/R305M/H307G/L364H/L407V/F450A/D470E/C503Q/Q521K/T524S/C565P | + | + | + |
| 663 | F16S/A39V/L47A/T54K/G59R/S73K/H307G/L364H/L407V/C503Q/Q521K/T524S | + | + | + |
| 664 | F16S/A39V/L47A/T54K/G59R/S73K/I285L/N290G/R305M/H307G/L364H/L407V/T524S | + | + | + |
| 665 | F16S/A39V/L47A/T54K/G59R/S73K/S98G/S209P/I285L/R305M/H307G/L407V/F450A/D470E/C503Q/T524S | + | + | + |
| 666 | F16S/A39V/L47A/T54K/S209P/H307G/C503Q | − | + | − |
| 667 | F16S/A39V/L47A/T54K/S209P/L214Q/I285L/N290G/R305M/H307G/L364H/D470E/C503Q/Q521K/T524S/C565P | + | + | + |
| 668 | F16S/A39V/L47A/T54K/S73K/A91V/S209P/H307G/L364H/L407V/D470E/C503Q/Q521K/T524S/C565P | + | + | + |
| 669 | F16S/A39V/L47A/T54K/S73K/A91V/S209P/L214Q/I285L/N290G/L407V/F450A/D470E/Q521K/T524S/C565P | + | + | + |
| 670 | F16S/A39V/Q521K/C565P | − | − | − |
| 671 | F16S/A39V/S73K/L364H | − | − | − |
| 672 | F16S/A39V/T54K/G59R/A91V/I285L/N290G/R305M/L364H/L407V/F450A/D470E/C503Q/Q521K/T524S/C565P | + | − | + |
| 673 | F16S/A39V/T54K/G59R/S73K/A91V/L214Q/I285L/N290G/R305M/H307G/L364H/L407V/D470E/C503Q/Q521K | + | + | + |
| 674 | F16S/A39V/T54K/G59R/S73K/A91V/L214Q/I285L/N290G/R305M/H307G/L364H/L407V/F450A/D470E/C503Q/Q521K/T524S/C565P | + | + | + |
| 675 | F16S/A39V/T54K/G59R/S73K/A91V/L214Q/N290G/R305M/H307G/L407V/D470E/C503Q/Q521K/T524S/C565P | + | ++ | + |
| 676 | F16S/A39V/T54K/G59R/S73K/A91V/S209P/L214Q/I285L/N290G/R305M/H307G/L364H/D470E/C503Q/Q521K/T524S/C565P | + | + | + |
| 677 | F16S/A91V/I285L/N290G/L364H/L407V | − | − | − |
| 678 | F16S/A91V/L214Q/L407V/C503Q | − | − | − |
| 679 | F16S/A91V/S209P/L214Q | + | − | + |
| 680 | F16S/A91V/S209P/L214Q/L364H/F450A | − | − | − |
| 681 | F16S/C565P | − | − | − |
| 682 | F16S/F18H/A39V/A91V/C503Q/Q521K | − | − | − |
| 683 | F16S/F18H/A39V/G45D/L47A/T54K/G59R/S73K/S98G/S209P/L214Q/I285L/N290G/R305M/L364H/L407V/F450A/D470E/C503Q/Q521K/T524S/C565P | + | + | + |
| 684 | F16S/F18H/A39V/L47A/A91V/N290G/L407V/ | − | − | − |
| 685 | F16S/F18H/A39V/L47A/G59R/L214Q/C503Q/C565P | − | − | − |
| 686 | F16S/F18H/A39V/L47A/G59R/S73K/A91V/L214Q/N290G/R305M/H307G/L364H/L407V/F450A/D470E/C503Q/Q521K | + | + | + |
| 687 | F16S/F18H/A39V/L47A/S49I/T54K/G59R/S73K/S209P/I285L/N290G/R305M/H307G/L364H/F450A/D470E/C503Q/Q521K/T524S/C565P | + | + | + |
| 688 | F16S/F18H/A39V/L47A/T54K/A91V/L214Q/I285L/N290G/L364H/L407V/F450A/D470E/C503Q/Q521K | + | − | + |
| 689 | F16S/F18H/A39V/L47A/T54K/G59R/A91V/I285L/N290G/R305M/H307G/L364H/L407V/F450A/C503Q/Q521K/T524S | + | − | + |
| 690 | F16S/F18H/A39V/L47A/T54K/G59R/A91V/L214Q/I285L/N290G/R305M/H307G/L364H/F450A/C503Q/Q521K/T524S | + | + | + |
| 691 | F16S/F18H/A39V/L47A/T54K/G59R/A91V/L214Q/I285L/N290G/R305M/H307G/L364H/L407V/F450A/D470E/C503Q/Q521K/T524S/C565P | + | + | + |
| 692 | F16S/F18H/A39V/L47A/T54K/G59R/A91V/S209P/L214Q/I285L/N290G/R305M/H307G/L364H/F450A/D470E/C503Q/Q521K/T524S/C565P | + | + | + |
| 693 | F16S/F18H/A39V/L47A/T54K/G59R/A91V/S98G/S209P/I285L/N290G/R305M/H307G/L364H/L407V/F450A/D470E/C503Q/Q521K/T524S | + | + | + |
| 694 | F16S/F18H/A39V/L47A/T54K/G59R/S73K/A91V/I285L/N290G/R305M/H307G/L364H/L407V/F450A/D470E/C503Q/Q521K | + | + | + |
| 695 | F16S/F18H/A39V/L47A/T54K/G59R/S73K/A91V/I285L/N290G/R305M/H307G/L364H/L407V/F450A/D470E/C503Q/Q521K/T524S/C565P | + | + | + |
| 696 | F16S/F18H/A39V/L47A/T54K/G59R/S73K/A91V/I285L/N290G/R305M/L364H/L407V/D470E/C503Q/Q521K/T524S | + | + | + |
| 697 | F16S/F18H/A39V/L47A/T54K/G59R/S73K/A91V/L214Q/I285L/N290G/R305M/H307G/L364H/L407V/C503Q | + | − | + |
| 698 | F16S/F18H/A39V/L47A/T54K/G59R/S73K/A91V/S209P/I285L/N290G/H307G/L364H/L407V/D470E/C503Q/Q521K/T524S/C565P | + | + | + |

TABLE 15.1-continued

Screening of Variants for PAL Activity

| Variant # | Amino Acid Sequence Changes (Relative to SEQ ID NO: 2) | FIOP (T = 0) | FIOP Protease | FIOP (T = 7) |
|---|---|---|---|---|
| 699 | F16S/F18H/A39V/L47A/T54K/G59R/S73K/A91V/S209P/ I285L/N290G/R305M/H307G/L407V/F450A/C503Q/Q521K/ T524S/C565P | + | − | + |
| 700 | F16S/F18H/A39V/L47A/T54K/G59R/S73K/A91V/S209P/ L214Q/I285L/N290G/H307G/L364H/L407V/F450A/D470E/ C503Q/T524S/C565P | + | + | + |
| 701 | F16S/F18H/A39V/L47A/T54K/G59R/S73K/A91V/S209P/ L214Q/I285L/N290G/R305M/H307G/L364H/F450A/D470E/ Q521K/T524S/C565P | + | − | + |
| 702 | F16S/F18H/A39V/L47A/T54K/G59R/S73K/A91V/S209P/ L214Q/I285L/N290G/R305M/H307G/L364H/L407V/F450A/ C503Q/Q521K/T524S | ++ | ++ | + |
| 703 | F16S/F18H/A39V/L47A/T54K/G59R/S73K/A91V/S209P/ L214Q/I285L/N290G/R305M/H307G/L364H/L407V/F450A/ D470E/C503Q/Q521K/T524S | ++ | ++ | + |
| 704 | F16S/F18H/A39V/L47A/T54K/G59R/S73K/A91V/S209P/ L214Q/I285L/N290G/R305M/H307G/L364H/L407V/F450A/ D470E/C503Q/Q521K/T524S/C565P | ++ | + | ++ |
| 705 | F16S/F18H/A39V/L47A/T54K/G59R/S73K/A91V/S209P/ L214Q/I285L/N290G/R305M/H307G/L364H/L407V/F450A/ D470E/Q521K/T524S/C565P | + | ++ | + |
| 706 | F16S/F18H/A39V/L47A/T54K/G59R/S73K/A91V/S209P/ L214Q/I285L/N290G/R305M/H307G/R313H/L364H/F450A/ C503Q/Q521K/T524S/C565P | − | − | − |
| 707 | F16S/F18H/A39V/L47A/T54K/G59R/S73K/A91V/S209P/ L214Q/I285L/N290G/R305M/L364H/L407V/D470E/C503Q/ Q521K/T524S | + | + | + |
| 708 | F16S/F18H/A39V/L47A/T54K/G59R/S73K/A91V/S209P/ L214Q/I285L/N290G/R305M/L364H/L407V/F450A/C503Q/ Q521K/T524S/C565P | + | + | + |
| 709 | F16S/F18H/A39V/L47A/T54K/G59R/S73K/A91V/S98G/ I285L/N290G/R305M/H307G/L364H/F450A/D470E/C503Q/ T524S/C565P | + | + | + |
| 710 | F16S/F18H/A39V/L47A/T54K/G59R/S73K/I285L/N290G/ R305M/H307G/L364H/L407V/F450A/D470E/C503Q/Q521K/ T524S/C565P | + | + | + |
| 711 | F16S/F18H/A39V/L47A/T54K/S209P/L214Q/L407V/C503Q/ T524S/C565P | − | − | − |
| 712 | F16S/F18H/A39V/L47A/T54K/S73K/A91V/S209P/I285L/ N290G/R305M/H307G/L364H/L407V/F450A/D470E/C503Q/ Q521K/T524S | + | + | + |
| 713 | F16S/F18H/A39V/L47A/T54K/S73K/A91V/S209P/L214Q/ I285L/N290G/R305M/H307G/L364H/L407V/D470E/C503Q/ Q521K/C565P | + | + | + |
| 714 | F16S/F18H/A39V/L47A/T54K/S73K/S209P/L214Q/I285L/ N290G/R305M/H307G/L364H/F450A/D470E/C503Q/Q521K/ T524S/C565P | ++ | + | ++ |
| 715 | F16S/F18H/A39V/R43G/N44K/G59R/S209P/C503Q/C565P | − | − | − |
| 716 | F16S/F18H/A39V/T54K/A91V/L214Q/I285L/N290G/L364H/ F450A/D470E/C503Q/Q521K/T524S | + | − | + |
| 717 | F16S/F18H/A39V/T54K/G59R/S73K/A91V/S209P/L214Q/ I285L/N290G/R305M/H307G/L364H/L407V/F450A/D470E/ C503Q/Q521K/T524S | + | + | + |
| 718 | F16S/F18H/A39V/T54K/G59R/S73K/L214Q/I285L/N290G/ R305M/L364H/L407V/F450A/Q521K/T524S/C565P | + | − | + |
| 719 | F16S/F18H/A39V/T54K/G59R/S73K/S209P/L214Q/I285L/ N290G/L364H/L407V/F450A/D470E/C503Q/Q521K/T524S/C565P | + | − | + |
| 720 | F16S/F18H/A39V/T54K/S73K/A91V/S209P/L214Q/I285L/ N290G/R305M/H307G/L364H/L407V/F450A/D470E/C503Q/ Q521K/T524S | + | + | + |
| 721 | F16S/F18H/A39V/T54K/S73K/A91V/S209P/P210S/I285L/ N290G/H307G/L364H/L407V/F450A/D470E/C503Q/Q521K/ T524S/C565P | + | + | + |
| 722 | F16S/F18H/A39V/T54K/S73K/S209P/I285L/N290G/R305M/ H307G/L364H/L407V/D470E/C503Q/Q521K/T524S/C565P | + | + | + |
| 723 | F16S/F18H/A39V/T54K/S73K/S98G/L214Q/I285L/N290G/ R305M/H307G/L364H/L407V/D470E/C503Q/Q521K/T524S/ C565P | + | + | + |
| 724 | F16S/F18H/A91V/L214Q/L407V/Q521K/T524S/C565P | − | − | − |
| 725 | F16S/F18H/A91V/S209P/L407V/C503Q | − | − | − |
| 726 | F16S/F18H/C503Q | + | − | − |
| 727 | F16S/F18H/D55H/S209P/I285L/R305M | − | − | − |
| 728 | F16S/F18H/G59R/S209P/F450A/C503Q/T524S | − | − | − |
| 729 | F16S/F18H/I285L/N290G/D470E | − | − | − |
| 730 | F16S/F18H/L214Q/L407V/F450A/C503Q | − | − | − |

TABLE 15.1-continued

Screening of Variants for PAL Activity

| Variant # | Amino Acid Sequence Changes (Relative to SEQ ID NO: 2) | FIOP (T = 0) | FIOP Protease | FIOP (T = 7) |
|---|---|---|---|---|
| 731 | F16S/F18H/L47A/G59R/I285L/L407V/F450A/C565P | − | − | − |
| 732 | F16S/F18H/L47A/I285L/L364H/C503Q/Q521K | − | − | − |
| 733 | F16S/F18H/L47A/L364H/L407V | − | − | + |
| 734 | F16S/F18H/L47A/S209P | − | − | − |
| 735 | F16S/F18H/L47A/S73K/A91V/S209P/I285L/N290G/F450A/D470E/C503Q/Q521K/T524S | + | + | + |
| 736 | F16S/F18H/L47A/S73K/L214Q/H307G/C503Q | − | − | − |
| 737 | F16S/F18H/L47A/S73K/N290G/L407V/F450A | − | − | − |
| 738 | F16S/F18H/L47A/T54K/G59R/S73K/A91V/S98G/I285L/N290G/L364H/L407V/F450A/D470E/C503Q/Q521K/T524S/C565P | + | − | + |
| 739 | F16S/F18H/L47A/T54K/G59R/S73K/S209P/I285L/N290G/R305M/H307G/L364H/F450A/D470E/C503Q/Q521K/T524S/C565P | + | + | + |
| 740 | F16S/F18H/L47A/T54K/G59R/S73K/S98G/S209P/N290G/R305M/H307G/L364H/F450A/D470E/C503Q/Q521K/T524S/C565P | + | − | + |
| 741 | F16S/F18H/L47A/T54K/S73K/A91V/S209P/L214Q/I285L/N290G/R305M/H307G/L364H/L407V/F450A/D470E/C503Q/Q521K/T524S/C565P | + | + | + |
| 742 | F16S/F18H/S209P/F450A/C503Q | − | − | − |
| 743 | F16S/F18H/S23G/L47A/T54K/G59R/S73K/A91V/S209P/L214Q/I285L/N290G/R305M/H307G/L364H/L407V/F450A/D470E/C503Q/Q521K/T524S/C565P | ++ | ++ | + |
| 744 | F16S/F18H/S73K/S209P/L214Q/F450A | + | − | − |
| 745 | F16S/F18H/T19I/L214Q/L407V | − | − | − |
| 746 | F16S/F18H/T54K/A91V/S209P/L214Q/I285L/N290G/H307G/L364H/L407V/F450A/C503Q/Q521K/T524S/C565P | + | − | + |
| 747 | F16S/F18H/T54K/G59R/N290G/L407V/F450A/C503Q/T524S | + | − | − |
| 748 | F16S/F18H/T54K/G59R/S73K/A91V/S209P/I285L/N290G/R305M/H307G/L364H/L407V/F450A/C503Q/Q521K | + | + | + |
| 749 | F16S/F18H/T54K/L407V | − | − | − |
| 750 | F16S/F18H/T54K/S73K/A91V/L214Q/I285L/N290G/L407V/D561G | − | − | − |
| 751 | F16S/F450A/D470E/T524S | + | − | − |
| 752 | F16S/G59R/L364H/L407V/F450A/T524S | − | − | − |
| 753 | F16S/G59R/S73K/A91V/M370Q/C503Q/T524S | − | − | − |
| 754 | F16S/G59R/S73K/C503Q/C565P | − | − | − |
| 755 | F16S/G59R/S73K/L407V/F450A/C503Q/C565P | − | − | − |
| 756 | F16S/L214Q/D470E | − | − | − |
| 757 | F16S/L214Q/L364H/D470E | + | − | + |
| 758 | F16S/L214Q/L407V/C565P | − | − | − |
| 759 | F16S/L364H/C503Q/C565F | − | − | − |
| 760 | F16S/L407V/D470E | − | − | − |
| 761 | F16S/L407V/T524S/C565P | − | − | − |
| 762 | F16S/L47A/A91V/L214Q/H307G/L407V/D470E/C503Q/C565P | − | − | − |
| 763 | F16S/L47A/F450A/D470E/C565P | − | − | − |
| 764 | F16S/L47A/F450A/Q521K | − | − | − |
| 765 | F16S/L47A/G59R/L364H/L407V/P523T | − | − | − |
| 766 | F16S/L47A/G59R/T524S | − | − | − |
| 767 | F16S/L47A/L407V/F450A/T524S | − | − | − |
| 768 | F16S/L47A/S209P/L214Q/L364H/L407V/D470E/C503Q/Q521K/C565P | − | − | − |
| 769 | F16S/L47A/S209P/L407V | − | − | − |
| 770 | F16S/L47A/S73K/A91V/L214Q/I285L/L407V/C565P | − | − | − |
| 771 | F16S/L47A/S73K/A91V/S209P/L214Q/I285L/N290G/R305M/H307G/L364H/F450A/D470E/C503Q/Q521K/T524S/C565P | + | + | + |
| 772 | F16S/L47A/S73K/L214Q/R305M/L407V/C565P | − | − | − |
| 773 | F16S/L47A/T54K/A91V/I285L/N290G/R305M/H307G/L407V/F450A/C503Q/Q521K/T524S/C565P | + | ++ | + |
| 774 | F16S/L47A/T54K/A91V/S209P/D470E/T524S/C565P | − | − | − |
| 775 | F16S/L47A/T54K/G59R/A91V/N290G/R305M/H307G/L364H/L407V/F450A/D470E/C503Q/Q521K/T524S/C565P | − | − | − |
| 776 | F16S/L47A/T54K/G59R/S73K/A91V/S209P/I285L/N290G/H307G/F450A/D470E/C503Q/Q521K/T524S/C565P | + | + | + |
| 777 | F16S/L47A/T54K/G59R/S73K/A91V/S209P/L214Q/I285L/N290G/R305M/F450A/D470E/C503Q/T524S/C565P | + | + | + |
| 778 | F16S/L47A/T54K/G59R/S73K/A91V/S209P/L214Q/I285L/N290G/R305M/L364H/F450A/D470E/C503Q/Q521K/T524S/C565P | + | + | + |
| 779 | F16S/L47A/T54K/L214Q/N290G/L364H/L407V/C503Q/Q521K/T524S | + | − | + |
| 780 | F16S/L47A/T54K/S73K/A91V/S209P/I285L/N290G/R305M/H307G/L364H/F450A/D470E/C503Q/Q521K/T524S/C565P | + | + | + |

TABLE 15.1-continued

Screening of Variants for PAL Activity

| Variant # | Amino Acid Sequence Changes (Relative to SEQ ID NO: 2) | FIOP (T = 0) | FIOP Protease | FIOP (T = 7) |
|---|---|---|---|---|
| 781 | F16S/N290G/R305M/L364H/L407V/D470E/A479T | − | − | − |
| 782 | F16S/S209P/L214Q/L407V/C503Q/T524S | − | − | + |
| 783 | F16S/S22G/L214Q/C503Q/T524S/C565P | − | + | − |
| 784 | F16S/S73K/A91V/S209P/D470E | − | − | − |
| 785 | F16S/S73K/L214Q/T524S | + | − | − |
| 786 | F16S/T54K/G59R/A91V/S209P/L364H/L407V/F450A/Q521K | − | − | − |
| 787 | F16S/T54K/G59R/L214Q/C565P | − | − | − |
| 788 | F16S/T54K/G59R/S209P/L214Q/I285L/F450A | − | − | − |
| 789 | F16S/T54K/G59R/S73K/A91V/N290G/H307G/L364H/F450A/ D470E/C503Q/Q521K/T524S/C565P | + | − | + |
| 790 | F16S/T54K/G59R/S73K/A91V/S209P/L214Q/I285L/N290G/ H307G/F450A/D470E/C503Q/T524S | + | + | + |
| 791 | F16S/T54K/S73K/A91V/I285L/N290G/R305M/H307G/ L407V/F450A/D470E/T524S | + | + | + |
| 792 | F16S/T54K/S73K/L407V/F450A/D470E/C503Q | + | − | − |
| 793 | F18H | − | − | − |
| 794 | F18H/A39V/D55N/L407V/D470E/C503Q | − | − | − |
| 795 | F18H/A39V/L214Q/L364H/F450A/D470E/Q521K/T524S | + | − | − |
| 796 | F18H/A39V/L214Q/L364H/L407V/D470E/C503Q | + | − | − |
| 797 | F18H/A39V/L47A/G59R/S73K/A91V/L214Q/I285L/H307G/ L364H/F450A/D470E/C503Q/Q521K/T524S/C565P | + | + | + |
| 798 | F18H/A39V/L47A/G59R/S73K/A91V/S209P/L214Q/I285L/ N290G/R305M/H307G/L364H/F450A/D470E/C503Q/Q521K/ T524S/C565P | + | − | + |
| 799 | F18H/A39V/L47A/G59R/S73K/S98G/S209P/L214Q/I285L/ N290G/R305M/H307G/L364H/L407V/F450A/D470E/C503Q/ T524S | + | + | + |
| 800 | F18H/A39V/L47A/S209P/L214Q/N290G/C565P | − | − | − |
| 801 | F18H/A39V/L47A/S73K/A91V/S209P/L214Q/N290G/R305M/ H307G/L364H/F450A/D470E/C503Q | + | + | + |
| 802 | F18H/A39V/L47A/T54K/A91V/L214Q/I285L/N290G/R305M/ H307G/L407V/F450A/C503Q/Q521K/T524S | + | ++ | + |
| 803 | F18H/A39V/L47A/T54K/G59R/A91V/S209P/I285L/N290G/ R305M/H307G/L364H/L407V/F450A/D470E/C503Q/Q521K/ T524S | + | + | + |
| 804 | F18H/A39V/L47A/T54K/G59R/A91V/S209P/L214Q/I285L/ N290G/R305M/H307G/L364H/L407V/F450A/D470E/C503Q/ Q521K/T524S/C565P | + | + | + |
| 805 | F18H/A39V/L47A/T54K/G59R/A91V/S209P/L214Q/N290G/ R305M/H307G/L364H/L407V/D470E/C503Q/Q521K/ T524S/C565P | + | ++ | + |
| 806 | F18H/A39V/L47A/T54K/G59R/A91V/S98G/S209P/I285L/ N290G/R305M/H307G/L364H/L407V/F450A/D470E/C503Q/ Q521K/T524S | + | + | + |
| 807 | F18H/A39V/L47A/T54K/G59R/L214Q/D470E/C503Q/Q521K/ T524S | − | − | − |
| 808 | F18H/A39V/L47A/T54K/G59R/S209P/I285L/N290G/R305M/ H307G/L407V/F450A/C503Q/Q521K/T524S | + | − | + |
| 809 | F18H/A39V/L47A/T54K/G59R/S209P/L214Q/I285L/N290G/ R305M/H307G/L364H/L407V/F450A/D470E/C503Q/ Q521K/C565P | + | + | + |
| 810 | F18H/A39V/L47A/T54K/G59R/S73K/A91V/I285L/N290G/ H307G/L364H/F450A/D470E/T524S | + | − | + |
| 811 | F18H/A39V/L47A/T54K/G59R/S73K/A91V/I285L/N290G/ R305M/H307G/L364H/L407V/F450A/C503Q/Q521K/T524S | + | + | + |
| 812 | F18H/A39V/L47A/T54K/G59R/S73K/A91V/I285L/N290G/ R305M/H307G/L364H/L407V/F450A/D470E/C503Q/Q521K/ T524S/C565P | + | + | + |
| 813 | F18H/A39V/L47A/T54K/G59R/S73K/A91V/I285L/N290G/ R305M/H307G/L364H/L407V/F450A/D470E/C503Q/T524S/ C565P | + | ++ | + |
| 814 | F18H/A39V/L47A/T54K/G59R/S73K/A91V/S209P/I285L/ N290G/R305M/H307G/L364H/L407V/F450A/D470E/C503Q | + | + | + |
| 815 | F18H/A39V/L47A/T54K/G59R/S73K/A91V/S209P/L214Q/ I285L/N290G/H307G/L364H/L407V/F450A/D470E/C503Q/ Q521K/T524S/C565P | + | − | + |
| 816 | F18H/A39V/L47A/T54K/G59R/S73K/A91V/S209P/L214Q/ I285L/N290G/R305M/H307G/L364H/L407V/C503Q/Q521K/ T524S | + | ++ | + |
| 817 | F18H/A39V/L47A/T54K/G59R/S73K/A91V/S209P/L214Q/ I285L/N290G/R305M/H307G/L364H/L407V/D470E/C503Q/ Q521K/T524S | + | ++ | ++ |
| 818 | F18H/A39V/L47A/T54K/G59R/S73K/A91V/S209P/L214Q/ I285L/N290G/R305M/H307G/L364H/L407V/F450A/C503Q/ Q521K/T524S/C565P | + | − | + |

TABLE 15.1-continued

Screening of Variants for PAL Activity

| Variant # | Amino Acid Sequence Changes (Relative to SEQ ID NO: 2) | FIOP (T = 0) | FIOP Protease | FIOP (T = 7) |
|---|---|---|---|---|
| 819 | F18H/A39V/L47A/T54K/G59R/S73K/A91V/S209P/L214Q/ I285L/N290G/R305M/H307G/L364H/L407V/F450A/D470E/ C503Q/Q521K/T524S | + | + | + |
| 820 | F18H/A39V/L47A/T54K/G59R/S73K/A91V/S209P/L214Q/ I285L/N290G/R305M/H307G/L364H/L407V/F450A/D470E/ C503Q/T524S/C565P | + | + | + |
| 821 | F18H/A39V/L47A/T54K/G59R/S73K/A91V/S209P/L214Q/ I285L/N290G/R305M/H307G/L364H/L407V/F450A/D470E/ Q521K/T524S/C565P | + | + | + |
| 822 | F18H/A39V/L47A/T54K/G59R/S73K/A91V/S209P/L214Q/ I285L/N290G/R305M/L364H/L407V/F450A/D470E/C503Q/ Q521K/T524S | ++ | − | + |
| 823 | F18H/A39V/L47A/T54K/G59R/S73K/A91V/S209P/L214Q/ N290G/H307G/L364H/L407V/F450A/D470E/C503Q/Q521K/ T524S/C565P | + | + | + |
| 824 | F18H/A39V/L47A/T54K/G59R/S73K/A91V/S209P/L214Q/ N290G/R305M/H307G/L407V/C503Q/T524S/C565P | + | ++ | + |
| 825 | F18H/A39V/L47A/T54K/G59R/S73K/A91V/S209P/N290G/ H307G/L364H/L407V/D470E/C503Q/Q521K/C565P | + | − | + |
| 826 | F18H/A39V/L47A/T54K/G59R/S73K/A91V/S98G/L214Q/ I285L/N290G/R305M/H307G/L364H/F450A/D470E/C503Q/ T524S | + | − | + |
| 827 | F18H/A39V/L47A/T54K/G59R/S73K/A91V/S98G/S209P/ L214Q/I285L/N290G/R305M/H307G/L364H/L407V/F450A/ D470E/C503Q/Q521K/T524S/C565P | + | + | + |
| 828 | F18H/A39V/L47A/T54K/G59R/S73K/A91V/S98G/S209P/ L214Q/I285L/N290G/R305M/H307G/L364H/L407V/F450A/ D470E/C503Q/T524S | + | + | + |
| 829 | F18H/A39V/L47A/T54K/G59R/S73K/L214Q/I285L/N290G/ R305M/L364H/L407V/F450A/D470E/C503Q/T524S | ++ | − | ++ |
| 830 | F18H/A39V/L47A/T54K/G59R/S73K/S209P/L214Q/I285L/ N290G/R305M/H307G/L364H/L407V/F450A/C503Q/Q521K/ C565P | + | + | + |
| 831 | F18H/A39V/L47A/T54K/S73K/A91V/G154S/S209P/N290G/ R305M/H307G/L364H/L407V/F450A/D470E/C503Q/Q521K/ T524S/C565P | + | + | + |
| 832 | F18H/A39V/L47A/T54K/S73K/A91V/I285L/N290G/R305M/ H307G/L364H/L407V/F450A/C503Q/Q521K/T524S | + | + | + |
| 833 | F18H/A39V/L47A/T54K/S73K/A91V/S209P/I285L/N290G/ R305M/H307G/L364H/L407V/D470E/Q521K/T524S/C565P | + | + | + |
| 834 | F18H/A39V/L47A/T54K/S73K/A91V/S209P/L214Q/I285L/ N290G/H307G/L364H/L407V/F450A/C503Q/C565P | + | − | + |
| 835 | F18H/A39V/L47A/T54K/S73K/A91V/S209P/L214Q/I285L/ N290G/H307G/L364H/L407V/F450A/D470E/C503Q/Q521K/ T524S/C565P | + | + | + |
| 836 | F18H/A39V/L47A/T54K/S73K/A91V/S209P/L214Q/I285L/ N290G/R305M/H307G/F450A/C503Q/Q521K/T524S/C565P | + | ++ | + |
| 837 | F18H/A39V/L47A/T54K/S73K/A91V/S209P/L214Q/I285L/ N290G/R305M/H307G/L364H/L407V/F450A/D470E/C503Q/ Q521K/T524S | ++ | + | + |
| 838 | F18H/A39V/L47A/T54K/S73K/A91V/S209P/R305M/L364H/ L407V/F450A/D470E/C503Q/Q521K | + | − | + |
| 839 | F18H/A39V/L47A/T54K/S73K/A91V/S98G/I285L/N290G/ R305M/F450A/C503Q/Q521K/T524S/C565P | + | + | + |
| 840 | F18H/A39V/L47A/T54K/S73K/A91V/S98G/L214Q/I285L/ N290G/R305M/H307G/L364H/L407V/F450A/D470E/C503Q/ Q521K/T524S/C565P | + | + | + |
| 841 | F18H/A39V/L47A/T54K/S73K/A91V/S98G/N290G/R305M/ H307G/L364H/F450A/D470E/C503Q/Q521K/T524S | + | + | + |
| 842 | F18H/A39V/S73K/A91V/L214Q/I285L/N290G/R305M/ L364H/L407V/F450A/D470E/C503Q/Q521K/T524S | + | + | ++ |
| 843 | F18H/A39V/S73K/A91V/S209P/L214Q/I285L/N290G/H307G/ L364H/L407V/F450A/D470E/C503Q/Q521K/T524S/C565P | + | + | + |
| 844 | F18H/A39V/T54K/G59R/A91V/S209P/L214Q/I285L/N290G/ R305M/H307G/L364H/L407V/F450A/D470E/C503Q/ Q521K/T524S/C565P | + | + | + |
| 845 | F18H/A39V/T54K/G59R/I285L/N290G/R305M/H307G/ L364H/L407V/F450A/D470E/C503Q/T524S | + | − | + |
| 846 | F18H/A39V/T54K/G59R/S73K/A91V/I285L/N290G/H307G/ L364H/L407V/F450A/D470E/C503Q/Q521K/T524S/C565P | + | + | + |
| 847 | F18H/A39V/T54K/G59R/S73K/A91V/I285L/N290G/R305M/ H307G/L364H/L407V/F450A/D470E/C503Q/Q521K/T524S/ C565P | + | + | + |
| 848 | F18H/A39V/T54K/G59R/S73K/A91V/L214Q/I285L/N290G/ H307G/L407V/F450A/D470E/C503Q/Q521K/T524S/C565P | + | + | + |

TABLE 15.1-continued

Screening of Variants for PAL Activity

| Variant # | Amino Acid Sequence Changes (Relative to SEQ ID NO: 2) | FIOP (T = 0) | FIOP Protease | FIOP (T = 7) |
|---|---|---|---|---|
| 849 | F18H/A39V/T54K/G59R/S73K/A91V/S209P/L214Q/I285L/ N290G/H307G/L364H/L407V/D470E/C503Q/Q521K | + | + | + |
| 850 | F18H/A39V/T54K/G59R/S73K/A91V/S209P/L214Q/I285L/ N290G/H307G/L364H/L407V/F450A/D470E/C503Q/Q521K/ T524S/C565P | + | + | + |
| 851 | F18H/A39V/T54K/G59R/S73K/A91V/S209P/L214Q/I285L/ N290G/R305M/H307G/L364H/L407V/F450A/C503Q/Q521K/ T524S | + | − | + |
| 852 | F18H/A39V/T54K/G59R/S73K/A91V/S209P/L214Q/I285L/ N290G/R305M/H307G/L364H/L407V/F450A/D470E/C503Q/ Q521K | + | + | + |
| 853 | F18H/A39V/T54K/G59R/S73K/A91V/S209P/L214Q/I285L/ N290G/R305M/H307G/L364H/L407V/F450A/D470E/C503Q/ Q521K/T524S | + | + | + |
| 854 | F18H/A39V/T54K/G59R/S73K/A91V/S209P/L214Q/I285L/ R305M/H307G/L364H/L407V/F450A/D470E/C503Q/Q521K/ T524S/C565P | + | + | + |
| 855 | F18H/A39V/T54K/G59R/S73K/A91V/S98G/S209P/L214Q/ I285L/N290G/R305M/H307G/L364H/D470E/C503Q/Q521K/ T524S/C565P | + | + | + |
| 856 | F18H/A39V/T54K/G59R/S73K/A91V/S98G/S209P/L214Q/ I285L/N290G/R305M/H307G/L364H/L407V/Q521K/T524S | − | − | − |
| 857 | F18H/A39V/T54K/G59R/S73K/I285L/N290G/H307G/L364H/ D470E/C503Q/Q521K/T524S/C565P | + | + | + |
| 858 | F18H/A39V/T54K/S73K/A91V/S209P/I285L/N290G/R305M/ H307G/L364H/L407V/F450A/D470E/C503Q | + | + | + |
| 859 | F18H/A39V/T54K/S73K/A91V/S98G/I285L/N290G/R305M/ L407V/F450A/D470E/C503Q/Q521K/T524S/C565P | + | + | + |
| 860 | F18H/A39V/T54K/S73K/S209P/L214Q/I285L/N290G/R305M/ H307G/L364H/L407V/C503Q/Q521K/T524S | + | ++ | + |
| 861 | F18H/A91V/L214Q | − | − | − |
| 862 | F18H/A91V/L214Q/L407V/T524S/C565P | − | − | − |
| 863 | F18H/A91V/L364H/F450A/C565P | − | − | − |
| 864 | F18H/A91V/L364H/L407V | − | − | − |
| 865 | F18H/A91V/L364H/L407V/F450A | − | − | − |
| 866 | F18H/A91V/L407V/C503Q | − | − | − |
| 867 | F18H/A91V/L407V/D470E/Q521K/T524S | − | − | − |
| 868 | F18H/A91V/S209P/L364H/L407V | − | − | − |
| 869 | F18H/F450A/C503Q | − | − | − |
| 870 | F18H/G59R/A91V/C565P | − | − | − |
| 871 | F18H/G59R/A91V/S209P/L214Q/L364H | − | − | − |
| 872 | F18H/G59R/C503Q/T524S | − | − | − |
| 873 | F18H/G59R/L407V/F450A | − | − | − |
| 874 | F18H/G59R/R305M/L364H/D470E/C565P | − | − | − |
| 875 | F18H/G59R/S209P | − | − | − |
| 876 | F18H/L214Q/L364H/L407V/D470E/C503Q/T524S | + | − | − |
| 877 | F18H/L214Q/L407V | + | − | + |
| 878 | F18H/L364H/C503Q | − | − | − |
| 879 | F18H/L364H/F450A/Q521K/T524S/C565P | + | − | − |
| 880 | F18H/L407V/F450A/C503Q/C565P | − | − | − |
| 881 | F18H/L47A/A97T/S98G/I182F/S209P/L364H/L407V/C503Q | − | − | − |
| 882 | F18H/L47A/F450A/D470E | − | − | − |
| 883 | F18H/L47A/G59R/A97T/S98G/L407V/C503Q | − | − | − |
| 884 | F18H/L47A/G59R/L214Q/F450A/Q521K | + | − | − |
| 885 | F18H/L47A/G59R/L214Q/I285L/C565P | − | − | − |
| 886 | F18H/L47A/G59R/L214Q/N362Y/L407V | − | − | − |
| 887 | F18H/L47A/L214Q/I285L/L287Q/N290G/D470E/C503Q | + | − | + |
| 888 | F18H/L47A/L214Q/L407V/T524S/C565P | − | − | − |
| 889 | F18H/L47A/L364H/C503Q | − | − | − |
| 890 | F18H/L47A/L364H/C503Q/C565P | − | − | − |
| 891 | F18H/L47A/L364H/D470E | − | − | − |
| 892 | F18H/L47A/Q521K/C565P | − | − | − |
| 893 | F18H/L47A/S209P/L407V/F450A/C503Q | − | − | − |
| 894 | F18H/L47A/S209P/L407V/F450A/D470E/C503Q/Q521K | + | − | − |
| 895 | F18H/L47A/S209P/N290G/L364H/D470E | − | − | − |
| 896 | F18H/L47A/S73K/A91V/L364H/L407V/C503Q | − | − | − |
| 897 | F18H/L47A/T54K/G59R/S73K/A91V/L214Q/I285L/N290G/ H307G/L364H/L407V/Q485H/C503Q/T524S/C565P | + | + | + |
| 898 | F18H/L47A/T54K/G59R/S73K/A91V/L214Q/I285L/N290G/ R305M/H307G/L364H/L407V/F450A/D470E/C503Q/Q521K/ T524S | + | + | + |
| 899 | F18H/L47A/T54K/G59R/S73K/A91V/S209P/L214Q/N290G/ R305M/L364H/L407V/F450A/C503Q/T524S | + | + | + |
| 900 | F18H/L47A/T54K/S73K/A91V/S209P/I285L/N290G/L364H/ L407V/F450A/D470E/C503Q/Q521K/T524S/C565P | + | − | + |

TABLE 15.1-continued

Screening of Variants for PAL Activity

| Variant # | Amino Acid Sequence Changes (Relative to SEQ ID NO: 2) | FIOP (T = 0) | FIOP Protease | FIOP (T = 7) |
|---|---|---|---|---|
| 901 | F18H/L47A/T54K/S73K/A91V/S209P/L214Q/I285L/N290G/R305M/H307G/L407V/D470E/C503Q/Q521K/T524S | + | + | + |
| 902 | F18H/N290G/C565P | − | − | + |
| 903 | F18H/R43S/R305M/L364H/M416I/F450A | − | − | − |
| 904 | F18H/S209P | − | − | − |
| 905 | F18H/S209P/L364H/L407V/Q521K/C565P | − | − | − |
| 906 | F18H/S22G/A39V/A91V/L214Q/I285L/F450A/D470E/C503Q | − | − | − |
| 907 | F18H/S73K/A91V/I182F/L287P/L407V/F450A/C503Q | − | − | − |
| 908 | F18H/S73K/I285L/L364H/L407V/D470E | − | − | − |
| 909 | F18H/S73K/I285L/Q521K/T524S | − | − | − |
| 910 | F18H/S73K/L364H/F450A/C565P | − | − | − |
| 911 | F18H/S73K/L407V | − | − | − |
| 912 | F18H/T54K/G59R/S73K/A91V/I285L/N290G/R305M/H307G/L364H/L407V/D470E/C503Q/Q521K/T524S | + | + | + |
| 913 | F18H/T54K/S73K/L214Q/H307G | − | + | − |
| 914 | F18I | − | − | − |
| 915 | F450A/C503Q | − | − | − |
| 916 | F450A/T524S | + | − | + |
| 917 | G59R/A91V/L407V/F450A | − | − | − |
| 918 | G59R/C565P | − | − | − |
| 919 | G59R/F450A/C503Q | − | − | − |
| 920 | G59R/L214Q | − | − | − |
| 921 | G59R/L214Q/F450A/C503Q | + | − | − |
| 922 | G59R/L214Q/L364H/L407V/Q452R/C503Q | − | − | − |
| 923 | G59R/L407V/C503Q/Q521K/T524S | − | − | − |
| 924 | G59R/S209P/L364H/D470E/C503Q | − | − | − |
| 925 | G59R/S73K/N290G/L407V/C503Q/V554I | − | − | − |
| 926 | G59R/S73K/R305M/H307G/C503Q | − | − | − |
| 927 | L214Q/D470E/C503Q | − | − | − |
| 928 | L214Q/D470E/Q521K | − | − | − |
| 929 | L214Q/I285L/H307G/C503Q/C565P | − | − | − |
| 930 | L214Q/L407V/C503Q/C565P | − | − | − |
| 931 | L364H | − | − | − |
| 932 | L364H/D470E/C503Q/Q521K/T524S | + | − | − |
| 933 | L364H/L407V/C565P | − | − | − |
| 934 | L364H/L407V/K419N/F450A/D470E/Q521K/C565P | − | − | − |
| 935 | L407V | − | − | − |
| 936 | L407V/C503Q | − | − | − |
| 937 | L407V/F450A/C565P | − | − | − |
| 938 | L47A | − | − | − |
| 939 | L47A/D55N | − | − | − |
| 940 | L47A/G59R/A91V/C503Q/Q521K | − | − | − |
| 941 | L47A/G59R/A91V/L407V/D470E/C503Q/C565P | − | − | − |
| 942 | L47A/G59R/F450A/D470E/C503Q | − | − | − |
| 943 | L47A/G59R/S209P | − | − | − |
| 944 | L47A/I285L/N290G/L364H/C503Q/C565P | − | − | − |
| 945 | L47A/L214Q/L364H/C503Q | + | − | − |
| 946 | L47A/L214Q/L407V | − | − | − |
| 947 | L47A/L364H/L407V/D470E/Q521K/T524S | + | − | − |
| 948 | L47A/L364H/T524S/C565P | − | − | − |
| 949 | L47A/L407V | − | − | − |
| 950 | L47A/L407V/C565P | − | − | − |
| 951 | L47A/L407V/F450A/Q521K/T524S | − | − | − |
| 952 | L47A/R305M | − | − | − |
| 953 | L47A/S209P/C503Q/T524S/C565P | − | − | − |
| 954 | L47A/S209P/L214Q/R305M/H307G/L364H/C503Q/Q521K/T524S | − | + | − |
| 955 | L47A/S73K | − | − | − |
| 956 | L47A/S73K/A91V/I285L/N290G/R305M/H307G/L364H/F450A/D470E/C503Q/Q521K/T524S | + | + | + |
| 957 | L47A/S73K/A91V/L214Q | − | − | − |
| 958 | L47A/S73K/A91V/N290G/L407V/M416I/F450A/C503Q/Q521K/T524S | − | − | − |
| 959 | L47A/S73K/L214Q/L364H/L407V | + | − | + |
| 960 | L47A/S73K/L214Q/R305M/H307G/L364H/C503Q/C565P | − | + | − |
| 961 | L47A/S73K/L214Q/R305M/L407V/C503Q/C565P | − | + | − |
| 962 | L47A/S73K/L407V/D470E/C503Q | + | − | + |
| 963 | L47A/S73K/S209P/L364H/F450A/Q521K | − | − | − |
| 964 | L47A/T524S/C565P | − | − | − |
| 965 | L47A/T54K/A91V/A97T/S209P/L364H/C503Q/C565P | − | − | − |
| 966 | L47A/T54K/G59R/S73K/A91V/I285L/N290G/Q311R/L364H/L407V/C503Q/Q521K/T524S/C565P | − | + | − |
| 967 | L47A/T54K/G59R/S73K/A91V/I285L/R305M/H307G/L407V/D470E/Q521K/T524S | + | ++ | + |
| 968 | L47A/T54K/G59R/S73K/A91V/S209P/I285L/N290G/R305M/H307G/L364H/L407V/F450A/C503Q/T524S/C565P | + | − | + |

TABLE 15.1-continued

Screening of Variants for PAL Activity

| Variant # | Amino Acid Sequence Changes (Relative to SEQ ID NO: 2) | FIOP (T = 0) | FIOP Protease | FIOP (T = 7) |
|---|---|---|---|---|
| 969 | L47A/T54K/G59R/S73K/A91V/S209P/I285L/N290G/R305M/H307G/L364H/L407V/F450A/D470E/C503Q/Q521K/T524S | + | + | + |
| 970 | L47A/T54K/G59R/S73K/A91V/S209P/L214Q/I285L/N290G/R305M/H307G/L364H/L407V/F450A/D470E/C503Q/Q521K/T524S/C565P | + | + | + |
| 971 | L47A/T54K/G59R/S73K/S209P/I285L/N290G/L364H/L407V/L432P/F450A/D470E/C503Q/Q521K/T524S/C565P | − | + | − |
| 972 | L47A/T54K/G59R/S73K/S98G/S209P/L214Q/I285L/N290G/R305M/H307G/L364H/L407V/F450A/D470E/C503Q/Q521K/T524S | + | − | + |
| 973 | L47A/T54K/S73K/A91V/I285L/N290G/H307G/L364H/F450A/D470E/C503Q/Q521K/T524S/C565P | + | − | + |
| 974 | L47A/T54K/S73K/A91V/S209P/L214Q/I285L/N290G/R305M/H307G/L364H/L407V/F450A/D470E/C503Q/Q521K/T524S/C565P | + | + | + |
| 975 | N290G/D470E | − | − | − |
| 976 | Q15H/F18H/A39V/L47A/T54K/G59R/S73K/A91V/S209P/L214Q/I285L/N290G/H307G/L364H/L407V/F450A/D470E/C503Q/Q521K/T524S/C565P | + | + | + |
| 977 | R305M/L407V/Q521K | − | − | − |
| 978 | S209P | − | − | − |
| 979 | S209P/D470E | + | − | − |
| 980 | S209P/L214Q/H307G/L407V/F450A/C503Q | − | − | − |
| 981 | S209P/L214Q/L407V/F450A/D470E/C503Q | − | − | − |
| 982 | S209P/L214Q/R305M | − | − | − |
| 983 | S73K/A91V/L214Q/T524S/C565P | − | − | − |
| 984 | S73K/A91V/Q521K | − | − | − |
| 985 | T51I/L407V/D470E/C503Q/T524S | − | − | − |
| 986 | T524S | − | − | − |
| 987 | T54K/C503Q | − | − | − |
| 988 | T54K/F450A | − | − | − |
| 989 | T54K/G59R/A91V/S209P/L407V | − | − | − |
| 990 | T54K/G59R/S73K/A91V/L214Q/I285L/N290G/L364H/L407V/D470E/C503Q/T524S/C565P | + | + | + |
| 991 | T54K/S209P/D470E/C503Q/T524S/C565P | − | − | − |
| 992 | T54K/S209P/I285L/N290G/R305M/H307G/L364H/L407V/F450A/D470E/C503Q/C565P | + | + | + |
| 993 | T54K/S209P/L407V/F450A/D470E/C565P | − | − | − |
| 994 | T54K/S73K/A91V/L214Q/F450A/C503Q/Q521K/T524S | − | − | − |
| 995 | T54K/S73K/A91V/R305M/L364H/L407V/F450A/D470E/C503Q/Q521K | − | − | − |
| 996 | T54K/S73K/F450A | + | − | − |
| 997 | A39V/L47A/T54K/G59R/S73K/A91V/S209P/L214Q/I285L/N290G/R305M/H307G/L364H/L407V/F450A/D470E/C503Q/Q521K/T524S/C565P | + | + | + |
| 998 | A39V/L47A/T54K/S73K/A91V/S209P/L214Q/I285L/N290G/R305M/H307G/L364H/L407V/F450A/D470E/C503Q/Q521K/T524S/C565P | + | ++ | + |
| 999 | A91V/L214Q | − | − | − |
| 1000 | F16S/A39V/L47A/T54K/G59R/S73K/A91V/L214Q/I285L/N290G/R305M/H307G/L364H/F450A/D470E/C503Q/Q521K/T524S | + | + | + |

In the above Table, the activity fold improvement (FIOP) is compared to that of SEQ ID NO: 12 (Variant #126), and defined as follows: "−" = less than 0.2-fold; "+" = greater than 0.2-fold, but less than 1-fold; "++" = greater than 1-fold, but less than 1.25-fold increased activity; and "+++" = greater than 1.25-fold activity.

While the invention has been described with reference to the specific embodiments, various changes can be made and equivalents can be substituted to adapt to a particular situation, material, composition of matter, process, process step or steps, thereby achieving benefits of the invention without departing from the scope of what is claimed.

For all purposes in the United States of America, each and every publication and patent document cited in this disclosure is incorporated herein by reference as if each such publication or document was specifically and individually indicated to be incorporated herein by reference. Citation of publications and patent documents is not intended as an indication that any such document is pertinent prior art, nor does it constitute an admission as to its contents or date.

We claim:

1. An engineered phenylalanine ammonia lyase polypeptide comprising an amino acid sequence having at least 95% sequence identity to SEQ ID NO: 6, wherein said amino acid sequence of said engineered polypeptide comprises an amino acid residue difference at position 16, wherein the amino acid positions of said amino acid sequence of said engineered polypeptide are numbered with reference to the amino acid sequence of SEQ ID NO: 2.

2. The engineered phenylalanine ammonia lyase polypeptide of claim 1, wherein the amino acid sequence of said engineered polypeptide further comprises at least one substitution or substitution set at one or more amino acid positions selected from 150, 44/56, 44/56/102/239/285/469/470/495, 44/239, 44/239/285/469/495, 44/239/285/470, 44/239/469/470, 44/239/470/546, 44/239/495, 44/239/495/546, 44/469/470, 102, 102/470, 162, 165, 188, 239/285, 239/285/469, 239/469/470/495, 264, 267, 285/469/470/495, 285/470, 285/470/495, 364, 455, 469/470, 472, and 482, wherein the amino acid positions are numbered with reference to SEQ ID NO:6.

3. The engineered phenylalanine ammonia lyase polypeptide of claim 1, wherein the amino acid sequence of said engineered polypeptide further comprises at least one substitution at one or more amino acid positions selected from 264, 364, 472, 482, and/or any combinations thereof, wherein the amino acid positions are numbered with reference to SEQ ID NO:6.

4. The engineered phenylalanine ammonia lyase polypeptide of claim 1, wherein the amino acid sequence of said engineered polypeptide further comprises at least one substitution at one or more amino acid positions selected from 150, 162, 188, 264, 267, 398, 434, 472, and 482, and/or any combinations thereof, wherein the amino acid positions are numbered with reference to SEQ ID NO:6.

5. The engineered phenylalanine ammonia lyase polypeptide of claim 1, wherein said engineered polypeptide is an *Anabaena variabilis* variant enzyme.

6. The engineered phenylalanine ammonia lyase polypeptide of claim 1, wherein said engineered polypeptide is more thermostable than wild-type *Anabaena variabilis* phenylalanine ammonia lyase.

7. The engineered phenylalanine ammonia lyase polypeptide of claim 1, wherein said engineered polypeptide more resistant to proteolysis than wild-type *Anabaena variabilis* phenylalanine ammonia lyase.

8. The engineered phenylalanine ammonia lyase polypeptide of claim 7, wherein said engineered phenylalanine ammonia lyase polypeptide is resistant to proteolysis by at least one digestive tract enzyme, than wild-type *Anabaena variabilis* phenylalanine ammonia lyase.

9. The engineered phenylalanine ammonia lyase polypeptide of claim 7, wherein said engineered phenylalanine ammonia lyase polypeptide is more resistant to proteolysis by chymotrypsin, trypsin, carboxypeptidases, and/or elastases than wild-type *Anabaena variabilis* phenylalanine ammonia lyase.

10. The engineered phenylalanine ammonia lyase polypeptide of claim 1, wherein said engineered polypeptide is more acid stable than wild-type *Anabaena variabilis* phenylalanine ammonia lyase.

11. The engineered phenylalanine ammonia lyase polypeptide of claim 1, wherein said polypeptide is purified.

12. A composition comprising at least one engineered phenylalanine ammonia lyase polypeptide of claim 1.

13. The composition of claim 12, wherein said composition is a pharmaceutical composition.

14. The composition of claim 13, further comprising at least one pharmaceutically acceptable excipient and/or carrier.

15. The composition of claim 13, wherein said composition is suitable for the treatment of phenylketonuria.

16. The composition of claim 13, wherein said composition is suitable for the treatment of elevated blood phenylalanine.

17. The composition of claim 13, wherein said composition is suitable for the treatment of tyrosinemia.

18. The composition of claim 13, wherein said composition is suitable for the treatment of elevated blood tyrosine.

19. The composition of claim 13, wherein said composition is in the form of a pill, tablet, capsule, gelcap, liquid, or emulsion.

20. The composition of claim 19, wherein said pill, tablet, capsule, or gelcap further comprises an enteric coating.

21. The composition of claim 13, wherein said composition is suitable for parenteral injection into a human.

22. The composition of claim 13, wherein said composition is coadministered with at least one additional therapeutically effective compound.

23. The composition of claim 22, wherein said composition comprises at least one additional therapeutically effective compound.

24. A method for treating the symptoms of phenylketonuria in a subject, comprising providing a subject having phenylketonuria, and providing the composition of claim 13, to said subject.

25. The method of claim 24, wherein the phenylalanine concentration in the blood of said subject is reduced upon providing said composition to said subject.

26. The method of claim 24, wherein the cinnamic acid concentration in the blood of said subject is increased upon providing said composition to said subject.

27. A method for treating the symptoms of phenylketonuria in a subject, comprising providing a subject having phenylketonuria, and providing the composition of claim 13, wherein said subject is able to eat a diet that is less restricted in its phenylalanine content than diets required by subjects who have not been provided said composition.

28. The method of claim 27, wherein said subject is an infant, child, young adult, or adult.

* * * * *